(12) United States Patent
Lau et al.

(10) Patent No.: US 11,308,441 B2
(45) Date of Patent: *Apr. 19, 2022

(54) METHOD AND SYSTEM FOR TRACKING AND MONITORING ASSETS

(71) Applicant: IpVenture, Inc., San Jose, CA (US)

(72) Inventors: Chung Lau, Sunnyvale, CA (US); C. Douglass Thomas, Saratoga, CA (US); Peter P. Tong, Mountain View, CA (US)

(73) Assignee: IpVenture, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/952,170

(22) Filed: Nov. 19, 2020

(65) Prior Publication Data

US 2021/0142272 A1  May 13, 2021

Related U.S. Application Data

(63) Continuation of application No. 16/830,666, filed on Mar. 26, 2020, which is a continuation of application
(Continued)

(51) Int. Cl.
*G06Q 10/08* (2012.01)
*G06Q 10/10* (2012.01)
(Continued)

(52) U.S. Cl.
CPC ....... *G06Q 10/0833* (2013.01); *A61B 5/0002* (2013.01); *A61B 5/0022* (2013.01);
(Continued)

(58) Field of Classification Search
None
See application file for complete search history.

(56) References Cited

U.S. PATENT DOCUMENTS 3,975,941 A  8/1976  Smith
4,719,920 A  1/1988  Alt et al.
(Continued)

FOREIGN PATENT DOCUMENTS

EP  0 874 529 A2  10/1998
EP  1 037 447 A2   9/2000
(Continued)

OTHER PUBLICATIONS

Notice of Allowance for U.S. Appl. No. 16/830,666, dated Jan. 28, 2021.
(Continued)

*Primary Examiner* — Quynh H Nguyen

(57) ABSTRACT

Improved approaches for tracking and monitoring status of articles are disclosed. The monitoring can produce notifications to interested parties. The notifications typically contain status information pertaining to the articles being tracked. Alternatively, interested parties can gain access to status information pertaining to the articles being tracked via a website. According to one embodiment, the status information includes at least position (location) information and shipping conditions information. Also disclosed are improved approaches for monitoring real time status information impacting inventory management of a company and/or its partners. Adverse changes in the status information of specific items can be identified in real time, and changes implemented as needed.

25 Claims, 42 Drawing Sheets

Related U.S. Application Data

No. 15/933,578, filed on Mar. 23, 2018, now Pat. No. 10,614,408, which is a continuation of application No. 13/802,641, filed on Mar. 13, 2013, now Pat. No. 10,628,783, which is a continuation of application No. 12/924,470, filed on Sep. 27, 2010, now Pat. No. 8,725,165, which is a continuation of application No. 11/732,581, filed on Apr. 3, 2007, now Pat. No. 7,809,377, which is a continuation of application No. 10/397,637, filed on Mar. 26, 2003, now Pat. No. 7,212,829.

(60) Provisional application No. 60/444,198, filed on Jan. 30, 2003, provisional application No. 60/418,491, filed on Oct. 15, 2002, provisional application No. 60/404,645, filed on Aug. 19, 2002, provisional application No. 60/375,998, filed on Apr. 24, 2002.

(51) Int. Cl.

| | | |
|---|---|---|
| *G06F 11/30* | (2006.01) | |
| *G16H 50/20* | (2018.01) | |
| *G16H 40/67* | (2018.01) | |
| *G16H 10/60* | (2018.01) | |
| *G16H 20/10* | (2018.01) | |
| *A61B 5/00* | (2006.01) | |
| *A61B 5/11* | (2006.01) | |
| *A61B 5/0205* | (2006.01) | |
| *H04W 4/029* | (2018.01) | |
| *G06Q 10/00* | (2012.01) | |
| *H04L 67/04* | (2022.01) | |
| *H04L 67/52* | (2022.01) | |
| *H04W 4/02* | (2018.01) | |
| *H04W 4/20* | (2018.01) | |
| *A61B 5/24* | (2021.01) | |
| *A61B 5/02* | (2006.01) | |
| *H04W 64/00* | (2009.01) | |

(52) U.S. Cl.
CPC ........ *A61B 5/0024* (2013.01); *A61B 5/02055* (2013.01); *A61B 5/1112* (2013.01); *A61B 5/1123* (2013.01); *A61B 5/6801* (2013.01); *A61B 5/7282* (2013.01); *A61B 5/742* (2013.01); *G06F 11/3013* (2013.01); *G06F 11/3055* (2013.01); *G06F 11/3058* (2013.01); *G06Q 10/00* (2013.01); *G06Q 10/0832* (2013.01); *G06Q 10/107* (2013.01); *G16H 10/60* (2018.01); *G16H 20/10* (2018.01); *G16H 40/67* (2018.01); *G16H 50/20* (2018.01); *H04L 67/04* (2013.01); *H04L 67/18* (2013.01); *H04W 4/02* (2013.01); *H04W 4/029* (2018.02); *H04W 4/20* (2013.01); *A61B 5/02* (2013.01); *A61B 5/1116* (2013.01); *A61B 5/1118* (2013.01); *A61B 5/24* (2021.01); *H04W 4/027* (2013.01); *H04W 64/00* (2013.01); *Y10S 128/92* (2013.01)

(56) References Cited

U.S. PATENT DOCUMENTS

| | | |
|---|---|---|
| 5,115,223 A | 5/1992 | Moody |
| 5,337,579 A | 8/1994 | Saia, III et al. |
| 5,347,274 A | 9/1994 | Hassett |
| 5,353,034 A | 10/1994 | Sato et al. |
| 5,384,824 A | 1/1995 | Alvesalo |
| 5,389,934 A | 2/1995 | Kass |
| 5,394,333 A | 2/1995 | Kao |
| 5,400,020 A | 3/1995 | Jones et al. |
| 5,422,814 A | 6/1995 | Sprague et al. |
| 5,422,816 A | 6/1995 | Sprague et al. |
| 5,448,773 A | 9/1995 | McBurney et al. |
| 5,461,365 A | 10/1995 | Schlager et al. |
| 5,470,233 A | 11/1995 | Fruchterman et al. |
| 5,491,486 A | 2/1996 | Welles, II et al. |
| 5,512,902 A | 4/1996 | Guthrie et al. |
| 5,515,858 A | 5/1996 | Myllymaki |
| 5,517,199 A | 5/1996 | DiMattei |
| 5,528,247 A | 6/1996 | Nonami |
| 5,528,518 A | 6/1996 | Bradshaw et al. |
| 5,532,690 A | 7/1996 | Hertel |
| 5,539,748 A | 7/1996 | Raith |
| 5,541,845 A | 7/1996 | Klein |
| 5,543,789 A | 8/1996 | Behr et al. |
| 5,550,551 A | 8/1996 | Alesio |
| 5,563,606 A | 10/1996 | Wang |
| 5,568,119 A | 10/1996 | Schipper et al. |
| 5,570,412 A | 10/1996 | LeBlanc |
| 5,576,716 A | 11/1996 | Sadler |
| 5,592,173 A | 1/1997 | Lau et al. |
| 5,598,460 A | 1/1997 | Tendler |
| 5,604,708 A | 2/1997 | Helms et al. |
| 5,608,909 A | 3/1997 | Atkinson et al. |
| 5,623,260 A | 4/1997 | Jones |
| 5,623,418 A | 4/1997 | Rostoker |
| 5,627,517 A | 5/1997 | Theimer et al. |
| 5,629,678 A | 5/1997 | Gargano et al. |
| 5,633,874 A | 5/1997 | Diachina et al. |
| 5,650,770 A | 7/1997 | Schlager et al. |
| 5,652,570 A | 7/1997 | Lepkofker |
| 5,673,692 A | 10/1997 | Schulze et al. |
| 5,686,888 A * | 11/1997 | Welles, II ............ B61L 25/025 340/3.31 |
| 5,710,551 A | 1/1998 | Ridgeway |
| 5,712,619 A | 1/1998 | Simkin |
| 5,731,757 A | 3/1998 | Layson, Jr. |
| 5,731,788 A | 3/1998 | Reeds |
| 5,742,233 A | 4/1998 | Hoffman et al. |
| 5,751,245 A | 5/1998 | Janky et al. |
| 5,771,001 A | 6/1998 | Cobb |
| 5,771,455 A | 6/1998 | Kennedy, III et al. |
| 5,774,876 A | 6/1998 | Woolley et al. |
| 5,786,789 A | 7/1998 | Janky |
| 5,797,091 A | 8/1998 | Clise et al. |
| 5,806,018 A | 9/1998 | Smith et al. |
| 5,808,565 A | 9/1998 | Matta et al. |
| RE35,920 E | 10/1998 | Sorden et al. |
| 5,825,283 A | 10/1998 | Camhi |
| 5,826,195 A | 10/1998 | Westerlage et al. |
| 5,828,953 A | 10/1998 | Kawase |
| 5,835,907 A | 11/1998 | Newman |
| 5,841,352 A | 11/1998 | Prakash |
| 5,844,862 A | 12/1998 | Cocatre-Zilgien |
| 5,850,196 A | 12/1998 | Mowers |
| 5,852,775 A | 12/1998 | Hidary |
| 5,861,841 A | 1/1999 | Gildea et al. |
| 5,864,315 A | 1/1999 | Welles, II et al. |
| 5,883,594 A | 3/1999 | Lau |
| 5,889,770 A | 3/1999 | Jokiaho et al. |
| 5,892,454 A | 4/1999 | Schipper et al. |
| 5,894,266 A | 4/1999 | Wood, Jr. et al. |
| 5,902,347 A | 5/1999 | Backman et al. |
| 5,905,461 A | 5/1999 | Neher |
| 5,910,799 A | 6/1999 | Carpenter et al. |
| 5,913,078 A | 6/1999 | Kimura et al. |
| 5,917,433 A * | 6/1999 | Keillor .................... G08G 1/20 340/989 |
| 5,918,180 A | 6/1999 | Dimino |
| 5,928,309 A | 7/1999 | Korver et al. |
| 5,938,721 A | 8/1999 | Dussell et al. |
| 5,940,004 A | 8/1999 | Fulton |
| 5,948,040 A | 9/1999 | DeLorme et al. |
| 5,948,043 A | 9/1999 | Mathis |
| 5,949,812 A | 9/1999 | Turney et al. |
| 5,950,125 A | 9/1999 | Buhrmann et al. |
| 5,959,575 A | 9/1999 | Abbott |
| 5,959,577 A | 9/1999 | Fan et al. |
| 5,963,130 A | 10/1999 | Schlager et al. |

(56) References Cited

U.S. PATENT DOCUMENTS

| | | |
|---|---|---|
| 5,982,285 A | 11/1999 | Bueche et al. |
| 5,982,807 A | 11/1999 | Snell |
| 5,983,108 A | 11/1999 | Kennedy, III et al. |
| 5,983,158 A | 11/1999 | Suzuki et al. |
| 5,991,690 A | 11/1999 | Murphy |
| 5,995,849 A | 11/1999 | Williams et al. |
| 6,002,363 A * | 12/1999 | Krasner ............... H01Q 21/28 342/357.77 |
| 6,002,982 A | 12/1999 | Fry |
| 6,009,319 A | 12/1999 | Khullar et al. |
| 6,013,007 A | 1/2000 | Root et al. |
| 6,014,080 A | 1/2000 | Layson, Jr. |
| 6,014,090 A | 1/2000 | Rosen et al. |
| 6,014,628 A | 1/2000 | Kovarik, Jr. |
| 6,018,704 A | 1/2000 | Kohli et al. |
| 6,023,241 A | 2/2000 | Clapper |
| 6,031,496 A | 2/2000 | Kuittinen et al. |
| 6,032,051 A | 2/2000 | Hall et al. |
| 6,034,622 A | 3/2000 | Levine |
| 6,052,646 A | 4/2000 | Kirkhart et al. |
| 6,052,696 A | 4/2000 | Euler et al. |
| 6,054,928 A | 4/2000 | Lemelson et al. |
| 6,064,336 A | 5/2000 | Krasner |
| 6,067,018 A | 5/2000 | Skelton et al. |
| 6,067,044 A | 5/2000 | Whelan et al. |
| 6,067,082 A | 5/2000 | Enmei |
| 6,072,396 A | 6/2000 | Gaukel |
| 6,075,987 A | 6/2000 | Camp, Jr. et al. |
| 6,078,290 A | 6/2000 | McBurney et al. |
| 6,083,248 A | 7/2000 | Thompson |
| 6,083,353 A | 7/2000 | Alexander, Jr. |
| 6,085,090 A | 7/2000 | Yee et al. |
| 6,094,168 A | 7/2000 | Duffett-Smith et al. |
| 6,094,642 A | 7/2000 | Stephenson et al. |
| 6,100,670 A | 8/2000 | Levesque |
| 6,100,806 A | 8/2000 | Gaukel |
| 6,101,710 A | 8/2000 | Selinger et al. |
| 6,104,334 A | 8/2000 | Allport |
| 6,111,538 A | 8/2000 | Schuchman et al. |
| 6,111,540 A | 8/2000 | Krasner |
| 6,115,595 A | 9/2000 | Rodal et al. |
| 6,121,921 A | 9/2000 | Ishigaki |
| 6,125,325 A | 9/2000 | Kohli et al. |
| 6,131,067 A | 10/2000 | Girerd et al. |
| 6,140,863 A | 10/2000 | Fujisawa |
| 6,140,957 A | 10/2000 | Wilson et al. |
| 6,141,570 A | 10/2000 | O'Neill, Jr. et al. |
| 6,144,303 A | 11/2000 | Federman |
| 6,148,280 A | 11/2000 | Kramer |
| 6,154,422 A | 11/2000 | Shinkawa et al. |
| 6,163,696 A | 12/2000 | Bi et al. |
| 6,169,902 B1 | 1/2001 | Kawamoto |
| 6,171,264 B1 | 1/2001 | Bader |
| 6,172,640 B1 | 1/2001 | Durst et al. |
| 6,175,616 B1 | 1/2001 | Light et al. |
| 6,198,390 B1 | 3/2001 | Schlager et al. |
| 6,198,431 B1 | 3/2001 | Gibson |
| 6,198,930 B1 | 3/2001 | Schipper |
| 6,199,045 B1 | 3/2001 | Giniger et al. |
| 6,204,807 B1 | 3/2001 | Odagiri et al. |
| 6,208,934 B1 | 3/2001 | Bechtolsheim et al. |
| 6,212,133 B1 | 4/2001 | McCoy et al. |
| 6,225,944 B1 | 5/2001 | Hayes |
| 6,226,622 B1 | 5/2001 | Dabbiere |
| 6,231,519 B1 | 5/2001 | Blants et al. |
| 6,232,916 B1 | 5/2001 | Grillo et al. |
| 6,236,358 B1 | 5/2001 | Durst et al. |
| 6,238,337 B1 | 5/2001 | Kambhatla et al. |
| 6,243,039 B1 | 6/2001 | Elliot |
| 6,243,660 B1 | 6/2001 | Hsu et al. |
| 6,246,376 B1 | 6/2001 | Bork et al. |
| 6,252,543 B1 | 6/2001 | Camp |
| 6,252,544 B1 | 6/2001 | Hoffberg |
| 6,259,944 B1 | 7/2001 | Margulis et al. |
| 6,263,280 B1 | 7/2001 | Stingone, Jr. |
| 6,266,612 B1 | 7/2001 | Dussell et al. |
| 6,272,457 B1 | 8/2001 | Ford et al. |
| 6,278,936 B1 | 8/2001 | Jones |
| 6,281,797 B1 | 8/2001 | Forster et al. |
| 6,282,362 B1 | 8/2001 | Murphy et al. |
| 6,282,495 B1 | 8/2001 | Kirkhart et al. |
| 6,285,314 B1 | 9/2001 | Nagatsuma et al. |
| 6,289,464 B1 | 9/2001 | Wecker et al. |
| 6,292,687 B1 | 9/2001 | Lowell et al. |
| 6,298,306 B1 | 10/2001 | Suarez et al. |
| 6,300,875 B1 | 10/2001 | Schafer |
| 6,302,844 B1 | 10/2001 | Walker et al. |
| 6,304,467 B1 | 10/2001 | Nebrigic |
| 6,314,308 B1 | 11/2001 | Sheynblat et al. |
| 6,315,719 B1 | 11/2001 | Rode et al. |
| 6,317,049 B1 | 11/2001 | Toubia et al. |
| 6,321,091 B1 | 11/2001 | Holland |
| 6,321,158 B1 | 11/2001 | DeLorme et al. |
| 6,323,807 B1 | 11/2001 | Golding et al. |
| 6,324,213 B1 | 11/2001 | Harrison |
| 6,327,533 B1 | 12/2001 | Chou |
| 6,330,149 B1 | 12/2001 | Burrell |
| 6,331,817 B1 | 12/2001 | Goldberg |
| 6,331,825 B1 | 12/2001 | Ladner et al. |
| 6,339,397 B1 | 1/2002 | Baker |
| 6,340,928 B1 | 1/2002 | McCurdy |
| 6,342,847 B1 | 1/2002 | Archuleta et al. |
| 6,349,257 B1 | 2/2002 | Liu et al. |
| 6,353,390 B1 | 3/2002 | Beri et al. |
| 6,353,798 B1 | 3/2002 | Green et al. |
| 6,356,836 B1 | 3/2002 | Adolph |
| 6,356,841 B1 | 3/2002 | Hamrick et al. |
| 6,362,778 B2 | 3/2002 | Neher |
| 6,363,254 B1 | 3/2002 | Jones et al. |
| 6,363,323 B1 | 3/2002 | Jones |
| 6,366,871 B1 | 4/2002 | Geva |
| 6,373,430 B1 | 4/2002 | Beason et al. |
| 6,377,810 B1 | 4/2002 | Geiger et al. |
| 6,384,724 B1 | 5/2002 | Landais |
| 6,388,612 B1 | 5/2002 | Neher |
| 6,393,346 B1 | 5/2002 | Keith et al. |
| 6,404,352 B1 | 6/2002 | Ichikawa et al. |
| 6,407,698 B1 | 6/2002 | Ayed |
| 6,411,892 B1 | 6/2002 | Van Diggelen |
| 6,411,899 B2 | 6/2002 | Dussell et al. |
| 6,421,538 B1 | 7/2002 | Byrne |
| 6,426,719 B1 | 7/2002 | Nagareda et al. |
| 6,427,120 B1 | 7/2002 | Garin et al. |
| 6,430,602 B1 | 8/2002 | Kay et al. |
| 6,433,732 B1 | 8/2002 | Dutta et al. |
| 6,434,396 B1 | 8/2002 | Rune |
| 6,437,692 B1 | 8/2002 | Petite et al. |
| 6,441,778 B1 | 8/2002 | Durst et al. |
| 6,442,380 B1 | 8/2002 | Mohindra |
| 6,442,391 B1 | 8/2002 | Johansson et al. |
| 6,443,890 B1 | 9/2002 | Schulze et al. |
| 6,445,937 B1 | 9/2002 | daSilva |
| 6,453,237 B1 | 9/2002 | Fuchs et al. |
| 6,463,272 B1 | 10/2002 | Wallace et al. |
| 6,466,821 B1 | 10/2002 | Pianca et al. |
| 6,469,639 B2 | 10/2002 | Tanenhaus |
| 6,478,736 B1 | 11/2002 | Mault |
| 6,484,034 B1 | 11/2002 | Tsunehara et al. |
| 6,496,775 B2 | 12/2002 | McDonald, Jr. et al. |
| 6,501,429 B2 | 12/2002 | Nakamura et al. |
| 6,505,048 B1 | 1/2003 | Moles et al. |
| 6,505,049 B1 | 1/2003 | Dorenbosch |
| 6,512,456 B1 | 1/2003 | Taylor, Jr. |
| 6,513,532 B2 | 2/2003 | Mault et al. |
| 6,522,871 B1 | 2/2003 | Patrick et al. |
| 6,522,889 B1 | 2/2003 | Aarnio |
| 6,529,164 B1 | 3/2003 | Carter |
| 6,529,822 B1 | 3/2003 | Millington et al. |
| 6,544,193 B2 | 4/2003 | Abreu |
| 6,552,652 B2 | 4/2003 | Beken |
| 6,553,310 B1 | 4/2003 | Lopke |
| 6,553,336 B1 | 4/2003 | Johnson et al. |
| 6,559,620 B2 | 5/2003 | Zhou et al. |
| 6,560,463 B1 | 5/2003 | Santhoff |

(56) References Cited

U.S. PATENT DOCUMENTS

| | | |
|---|---|---|
| 6,569,094 B2 | 5/2003 | Suzuki et al. |
| 6,571,193 B1 | 5/2003 | Unuma et al. |
| 6,579,231 B1 | 6/2003 | Phipps |
| 6,579,844 B1 | 6/2003 | Morrison et al. |
| 6,611,688 B1 | 8/2003 | Raith |
| 6,616,593 B1 | 9/2003 | Elliot et al. |
| 6,625,437 B1 | 9/2003 | Jampolsky et al. |
| 6,630,885 B2 | 10/2003 | Hardman et al. |
| 6,640,085 B1 | 10/2003 | Chatzipetros et al. |
| 6,650,907 B1 | 11/2003 | Kamperschroer et al. |
| 6,661,372 B1 | 12/2003 | Girerd et al. |
| 6,679,071 B1 | 1/2004 | Storey et al. |
| 6,696,982 B2 | 2/2004 | Yoshioka et al. |
| 6,697,103 B1 | 2/2004 | Fernandez et al. |
| 6,697,730 B2 | 2/2004 | Dickerson |
| 6,714,158 B1 | 3/2004 | Underbrink et al. |
| 6,714,791 B2 | 3/2004 | Friedman |
| 6,721,542 B1 | 4/2004 | Anttila et al. |
| 6,737,989 B2 | 5/2004 | Flick |
| 6,741,927 B2 | 5/2004 | Jones |
| 6,747,675 B1 | 6/2004 | Abbott et al. |
| 6,748,318 B1 | 6/2004 | Jones |
| 6,788,766 B2 | 9/2004 | Logan |
| 6,801,853 B2 | 10/2004 | Workman |
| 6,804,606 B2 | 10/2004 | Jones |
| 6,819,269 B2 | 11/2004 | Flick |
| 6,825,767 B2 | 11/2004 | Humbard |
| 6,832,093 B1 | 12/2004 | Ranta |
| 6,847,892 B2 | 1/2005 | Zhou et al. |
| 6,856,804 B1 | 2/2005 | Ciotta |
| 6,856,807 B1 | 2/2005 | Raith |
| 6,865,385 B1 | 3/2005 | Kohda et al. |
| 6,876,862 B1 | 4/2005 | Tanaka |
| 6,888,879 B1 | 5/2005 | Lennen |
| 6,937,900 B1 | 8/2005 | Pianca et al. |
| 6,952,645 B1 | 10/2005 | Jones |
| 6,975,941 B1 | 12/2005 | Lau et al. |
| 6,980,813 B2 | 12/2005 | Mohi et al. |
| 6,980,826 B2 | 12/2005 | Yamaguchi |
| 6,997,882 B1 | 2/2006 | Parker et al. |
| 7,003,273 B1 * | 2/2006 | Shimanuki ............... H03B 5/04 |
| | | 331/176 |
| 7,010,144 B1 | 3/2006 | Davis et al. |
| 7,071,842 B1 | 7/2006 | Brady, Jr. |
| 7,085,253 B2 | 8/2006 | Yang |
| 7,110,773 B1 | 9/2006 | Wallace et al. |
| 7,136,832 B2 | 11/2006 | Li et al. |
| 7,187,278 B2 | 3/2007 | Biffar |
| 7,212,829 B1 | 5/2007 | Lau et al. |
| 7,218,938 B1 | 5/2007 | Lau et al. |
| 7,253,731 B2 | 8/2007 | Joao |
| 7,308,272 B1 | 12/2007 | Wortham |
| 7,321,774 B1 | 1/2008 | Lau et al. |
| 7,325,061 B2 | 1/2008 | Haruki |
| 7,366,522 B2 | 4/2008 | Thomas |
| 7,375,682 B1 | 5/2008 | Tester et al. |
| 7,403,972 B1 | 7/2008 | Lau et al. |
| 7,482,920 B2 | 1/2009 | Joao |
| 7,498,870 B2 * | 3/2009 | Mair ..................... G11C 5/147 |
| | | 327/540 |
| 7,539,557 B2 | 5/2009 | Yamauchi |
| 7,663,502 B2 | 2/2010 | Breed |
| 7,809,377 B1 | 10/2010 | Lau et al. |
| 7,905,832 B1 | 3/2011 | Lau et al. |
| 7,953,809 B2 | 5/2011 | Lau et al. |
| 8,131,326 B2 | 3/2012 | Persico |
| 8,176,135 B2 | 5/2012 | Lau et al. |
| 8,285,484 B1 | 10/2012 | Lau et al. |
| 8,301,158 B1 | 10/2012 | Thomas |
| 8,447,822 B2 | 5/2013 | Lau et al. |
| 8,611,920 B2 | 12/2013 | Lau et al. |
| 8,620,343 B1 | 12/2013 | Lau et al. |
| 8,700,050 B1 | 4/2014 | Thomas |
| 8,725,165 B2 | 5/2014 | Lau et al. |
| 8,753,273 B1 | 6/2014 | Lau et al. |
| 8,868,103 B2 | 10/2014 | Thomas |
| 8,886,220 B2 | 11/2014 | Lau et al. |
| 8,975,941 B2 | 3/2015 | Zierhofer |
| 9,049,571 B2 | 6/2015 | Lau et al. |
| 9,074,903 B1 | 7/2015 | Lau et al. |
| 9,082,103 B2 | 7/2015 | Breed |
| 9,182,238 B2 | 11/2015 | Lau et al. |
| 9,219,988 B2 | 12/2015 | Lau et al. |
| 9,456,350 B2 | 9/2016 | Lau et al. |
| 9,596,579 B2 | 3/2017 | Lau et al. |
| 9,706,374 B2 | 7/2017 | Lau et al. |
| 9,723,442 B2 | 8/2017 | Lau et al. |
| 9,759,817 B2 | 9/2017 | Lau et al. |
| 9,769,630 B2 | 9/2017 | Lau et al. |
| 9,930,503 B2 | 3/2018 | Lau et al. |
| 9,998,886 B2 | 6/2018 | Lau et al. |
| 10,034,150 B2 | 7/2018 | Lau et al. |
| 10,152,876 B2 | 12/2018 | Joao |
| 10,327,115 B2 | 6/2019 | Lau et al. |
| 10,356,568 B2 | 7/2019 | Lau et al. |
| 10,516,975 B2 | 12/2019 | Lau et al. |
| 10,609,516 B2 | 3/2020 | Lau et al. |
| 10,614,408 B2 | 4/2020 | Lau et al. |
| 10,628,783 B2 | 4/2020 | Lau et al. |
| 10,652,690 B2 | 5/2020 | Lau et al. |
| 10,664,789 B2 | 5/2020 | Lau et al. |
| 10,715,970 B2 | 7/2020 | Lau et al. |
| 10,761,214 B2 | 9/2020 | Lau et al. |
| 10,827,298 B2 | 11/2020 | Lau et al. |
| 10,848,932 B2 | 11/2020 | Lau et al. |
| 10,873,828 B2 | 12/2020 | Lau et al. |
| 11,032,677 B2 | 6/2021 | Lau et al. |
| 11,041,960 B2 | 6/2021 | Lau et al. |
| 11,054,527 B2 | 7/2021 | Lau et al. |
| 11,067,704 B2 | 7/2021 | Lau et al. |
| 2001/0006891 A1 | 7/2001 | Cho |
| 2001/0020202 A1 | 9/2001 | Obradovich et al. |
| 2001/0020204 A1 | 9/2001 | Runyon et al. |
| 2001/0022558 A1 | 9/2001 | Karr, Jr. et al. |
| 2001/0023448 A1 | 9/2001 | Hanhan |
| 2001/0026240 A1 | 10/2001 | Neher |
| 2001/0027378 A1 | 10/2001 | Tennison et al. |
| 2001/0027384 A1 | 10/2001 | Schulze et al. |
| 2001/0027525 A1 | 10/2001 | Gamlin |
| 2001/0028304 A1 | 10/2001 | I'Anson et al. |
| 2001/0041554 A1 | 11/2001 | Rowell |
| 2001/0044299 A1 | 11/2001 | Sandegren |
| 2001/0044332 A1 | 11/2001 | Yamada et al. |
| 2001/0047125 A1 | 11/2001 | Quy |
| 2001/0052849 A1 | 12/2001 | Jones, Jr. |
| 2001/0053699 A1 | 12/2001 | McCrady et al. |
| 2002/0000916 A1 | 1/2002 | Richards |
| 2002/0000930 A1 | 1/2002 | Crowson et al. |
| 2002/0008661 A1 | 1/2002 | McCall et al. |
| 2002/0015439 A1 | 2/2002 | Kohli et al. |
| 2002/0016173 A1 | 2/2002 | Hunzinger |
| 2002/0027507 A1 | 3/2002 | Yarin et al. |
| 2002/0028988 A1 | 3/2002 | Suzuki et al. |
| 2002/0036593 A1 | 3/2002 | Ying |
| 2002/0038182 A1 | 3/2002 | Wong et al. |
| 2002/0047649 A1 | 4/2002 | Fregoso et al. |
| 2002/0049742 A1 | 4/2002 | Chan et al. |
| 2002/0050945 A1 | 5/2002 | Tsukishima et al. |
| 2002/0052794 A1 | 5/2002 | Bhadra |
| 2002/0055362 A1 | 5/2002 | Aoyama |
| 2002/0057192 A1 | 5/2002 | Eagleson et al. |
| 2002/0063622 A1 | 5/2002 | Armstrong et al. |
| 2002/0070862 A1 | 6/2002 | Francis et al. |
| 2002/0071677 A1 | 6/2002 | Sumanaweera |
| 2002/0077080 A1 | 6/2002 | Greene |
| 2002/0087260 A1 | 7/2002 | Hancock et al. |
| 2002/0087619 A1 | 7/2002 | Tripathi |
| 2002/0094067 A1 | 7/2002 | August |
| 2002/0099567 A1 | 7/2002 | Joao |
| 2002/0111171 A1 | 8/2002 | Boesch et al. |
| 2002/0111819 A1 | 8/2002 | Li et al. |
| 2002/0115450 A1 | 8/2002 | Muramatsu |
| 2002/0115453 A1 | 8/2002 | Poulin et al. |
| 2002/0116080 A1 | 8/2002 | Birnbach et al. |

(56) References Cited

U.S. PATENT DOCUMENTS

| | | |
|---|---|---|
| 2002/0119770 A1 | 8/2002 | Twitchell et al. |
| 2002/0119789 A1 | 8/2002 | Friedman |
| 2002/0120394 A1 | 8/2002 | Rayne |
| 2002/0120475 A1 | 8/2002 | Morimoto |
| 2002/0120503 A1 | 8/2002 | Iwayama et al. |
| 2002/0123353 A1 | 9/2002 | Savoie |
| 2002/0138196 A1 | 9/2002 | Polidi et al. |
| 2002/0140081 A1 | 10/2002 | Chou et al. |
| 2002/0173910 A1 | 11/2002 | McCall et al. |
| 2002/0177476 A1* | 11/2002 | Chou .................. G01S 5/0027 455/574 |
| 2002/0191757 A1 | 12/2002 | Belrose |
| 2002/0193121 A1 | 12/2002 | Nowak et al. |
| 2002/0193996 A1 | 12/2002 | Squibbs et al. |
| 2002/0198003 A1 | 12/2002 | Klapman |
| 2002/0198055 A1 | 12/2002 | Bull et al. |
| 2003/0001775 A1 | 1/2003 | Turner |
| 2003/0003943 A1 | 1/2003 | Bajikar |
| 2003/0009410 A1 | 1/2003 | Ramankutty et al. |
| 2003/0013445 A1 | 1/2003 | Fujiwara et al. |
| 2003/0018430 A1 | 1/2003 | Ladetto et al. |
| 2003/0036389 A1 | 2/2003 | Yen |
| 2003/0036683 A1 | 2/2003 | Kehr et al. |
| 2003/0054827 A1 | 3/2003 | Schmidl et al. |
| 2003/0068605 A1 | 4/2003 | Kullok et al. |
| 2003/0069759 A1 | 4/2003 | Smith |
| 2003/0083011 A1 | 5/2003 | Haller et al. |
| 2003/0083046 A1 | 5/2003 | Mathis |
| 2003/0083814 A1 | 5/2003 | Gronemeyer |
| 2003/0092448 A1 | 5/2003 | Forstrom et al. |
| 2003/0095540 A1 | 5/2003 | Mulligan et al. |
| 2003/0100326 A1 | 5/2003 | Grube et al. |
| 2003/0101225 A1 | 5/2003 | Han et al. |
| 2003/0107514 A1 | 6/2003 | Syrjarinne et al. |
| 2003/0110003 A1 | 6/2003 | Topmiller |
| 2003/0114206 A1 | 6/2003 | Timothy et al. |
| 2003/0151507 A1 | 8/2003 | Andre et al. |
| 2003/0163287 A1 | 8/2003 | Vock et al. |
| 2003/0182052 A1 | 9/2003 | DeLorme |
| 2003/0204132 A1 | 10/2003 | Suzuki et al. |
| 2004/0034470 A1 | 2/2004 | Workman |
| 2004/0046637 A1 | 3/2004 | Wesby Van Swaay |
| 2004/0114731 A1 | 6/2004 | Gillett et al. |
| 2004/0117108 A1 | 6/2004 | Nemeth |
| 2004/0172566 A1 | 9/2004 | Greiger et al. |
| 2004/0180701 A1 | 9/2004 | Livet et al. |
| 2004/0192352 A1 | 9/2004 | Vallstrom et al. |
| 2004/0203352 A1 | 10/2004 | Hall et al. |
| 2004/0204820 A1 | 10/2004 | Diaz |
| 2004/0233065 A1 | 11/2004 | Freeman |
| 2005/0046584 A1 | 3/2005 | Breed |
| 2005/0068169 A1 | 3/2005 | Copley et al. |
| 2005/0250440 A1 | 11/2005 | Zhou et al. |
| 2005/0278063 A1 | 12/2005 | Hersh et al. |
| 2006/0073851 A1 | 4/2006 | Colando et al. |
| 2006/0129691 A1 | 6/2006 | Coffee et al. |
| 2006/0139375 A1 | 6/2006 | Rasmussen et al. |
| 2006/0173444 A1 | 8/2006 | Choy et al. |
| 2006/0211430 A1 | 9/2006 | Persico |
| 2007/0156286 A1 | 7/2007 | Yamauchi |
| 2007/0242131 A1 | 10/2007 | Sanz-Pastor et al. |
| 2008/0021645 A1 | 1/2008 | Lau et al. |
| 2008/0261636 A1 | 10/2008 | Lau et al. |
| 2009/0042540 A1 | 2/2009 | Bodnar et al. |
| 2011/0022533 A1 | 1/2011 | Lau et al. |
| 2011/0223884 A1 | 9/2011 | Lau et al. |
| 2012/0220266 A1 | 8/2012 | Lau et al. |
| 2013/0203388 A1 | 8/2013 | Thomas et al. |
| 2013/0297524 A1 | 11/2013 | Lau et al. |
| 2014/0011524 A1 | 1/2014 | Lau et al. |
| 2014/0067708 A1 | 3/2014 | Lau et al. |
| 2014/0273953 A1 | 9/2014 | Lau et al. |
| 2014/0278084 A1 | 9/2014 | Lau et al. |
| 2014/0296659 A1 | 10/2014 | Lau et al. |
| 2015/0011243 A1 | 1/2015 | Thomas et al. |
| 2015/0038168 A1 | 2/2015 | Thomas et al. |
| 2015/0264576 A1 | 9/2015 | Lau et al. |
| 2016/0025863 A1 | 1/2016 | Lau et al. |
| 2016/0029175 A1 | 1/2016 | Lau et al. |
| 2016/0050533 A1 | 2/2016 | Lau et al. |
| 2017/0013426 A1 | 1/2017 | Lau et al. |
| 2017/0094458 A1 | 3/2017 | Thomas et al. |
| 2017/0111776 A1 | 4/2017 | Lau et al. |
| 2017/0111777 A1 | 4/2017 | Lau et al. |
| 2017/0188208 A1 | 6/2017 | Lau et al. |
| 2017/0295462 A1 | 10/2017 | Lau et al. |
| 2017/0353841 A1 | 12/2017 | Lau et al. |
| 2018/0011201 A1 | 1/2018 | Lau et al. |
| 2018/0027394 A1 | 1/2018 | Lau et al. |
| 2018/0211216 A1 | 7/2018 | Lau et al. |
| 2018/0213372 A1 | 7/2018 | Lau et al. |
| 2018/0255439 A1 | 9/2018 | Lau et al. |
| 2018/0302759 A1 | 10/2018 | Lau et al. |
| 2019/0215643 A1 | 7/2019 | Lau et al. |
| 2020/0064491 A1 | 2/2020 | Lau et al. |
| 2020/0077236 A1 | 3/2020 | Lau et al. |
| 2020/0226542 A1 | 7/2020 | Lau et al. |
| 2020/0242551 A1 | 7/2020 | Lau et al. |
| 2020/0304963 A1 | 9/2020 | Lau et al. |
| 2020/0326429 A1 | 10/2020 | Lau et al. |
| 2020/0355833 A1 | 11/2020 | Lau et al. |
| 2021/0160651 A1 | 5/2021 | Lau et al. |
| 2021/0223404 A1 | 7/2021 | Lau et al. |

FOREIGN PATENT DOCUMENTS

| | | |
|---|---|---|
| EP | 1 037 447 A3 | 10/2001 |
| JP | 09251069 A | 9/1997 |
| JP | 11-64482 | 3/1999 |
| JP | 11-258325 | 9/1999 |
| JP | 11-289574 | 10/1999 |
| JP | 11-306491 | 11/1999 |
| JP | 2001344678 A | 12/2001 |
| WO | WO 97/14054 | 4/1997 |
| WO | WO 97/41654 A1 | 11/1997 |
| WO | WO 98/01769 A1 | 1/1998 |
| WO | WO 98/16045 A1 | 4/1998 |
| WO | WO 98/40837 | 9/1998 |
| WO | WO 00/51391 | 8/2000 |
| WO | WO 01/50151 A1 | 7/2001 |
| WO | WO 01/63318 A1 | 8/2001 |
| WO | WO 01/75700 A2 | 10/2001 |
| WO | WO 02/42979 A1 | 5/2002 |
| WO | WO 02/084618 A1 | 10/2002 |
| WO | WO 03/012720 A1 | 2/2003 |

OTHER PUBLICATIONS

Office Action for U.S. Appl. No. 10/397,637, dated Sep. 29, 2006.

Notice of Allowance for U.S. Appl. No. 10/397,637, dated Jan. 22, 2007.

Office Action for U.S. Appl. No. 11/732,581, dated Jan. 20, 2010.

Notice of Allowance for U.S. Appl. No. 11/732,581, dated Jun. 16, 2010.

Non-Final Office Action for U.S. Appl. No. 12/924,470, dated May 4, 2012.

Notice of Allowance for U.S. Appl. No. 12/924,470, dated Nov. 23, 2012.

Notice of Allowance for U.S. Appl. No. 12/924,470, dated Mar. 20, 2013.

Notice of Allowance for U.S. Appl. No. 12/924,470, dated Aug. 29, 2013.

Notice of Allowance for U.S. Appl. No. 12/924,470, dated Dec. 19, 2013.

Notice of Allowance for U.S. Appl. No. 13/802,641, dated Jan. 17, 2018.

Notice of Allowance for U.S. Appl. No. 13/802,641, dated Aug. 16, 2017.

Notice of Allowance for U.S. Appl. No. 13/802,641, dated Apr. 27, 2017.

Notice of Allowance for U.S. Appl. No. 13/802,641, dated Jan. 13, 2017.

(56) References Cited

OTHER PUBLICATIONS

Notice of Allowance for U.S. Appl. No. 13/802,641, dated Sep. 29, 2016.
Notice of Allowance for U.S. Appl. No. 13/802,641, dated Jun. 16, 2016.
Notice of Allowance for U.S. Appl. No. 13/802,641, dated Mar. 3, 2016.
Notice of Allowance for U.S. Appl. No. 13/802,641, dated Nov. 9, 2015.
Notice of Allowance for U.S. Appl. No. 13/802,641, dated Jul. 8, 2015.
Notice of Allowance for U.S. Appl. No. 13/802,641, dated Jan. 21, 2015.
Notice of Allowance for U.S. Appl. No. 13/802,641, dated Aug. 18, 2014.
Office Action for U.S. Appl. No. 13/802,641, dated Mar. 27, 2014.
U.S. Appl. No. 13/802,641, filed Mar. 13, 2013.
Office Action for U.S. Appl. No. 13/802,641, dated Oct. 24, 2018.
Office Action for U.S. Appl. No. 13/802,641, dated Jun. 7, 2019.
Notice of Allowance for U.S. Appl. No. 13/802,641, dated Sep. 16, 2019.
Notice of Allowance for U.S. Appl. No. 13/802,641, dated Jan. 6, 2020.
U.S. Appl. No. 13/802,624, filed Mar. 13, 2013.
Office Action for U.S. Appl. No. 13/802,624, dated Nov. 18, 2014.
Office Action for U.S. Appl. No. 13/802,624, dated May 26, 2015.
Office Action for U.S. Appl. No. 15/933,578, dated Apr. 12, 2019.
Office Action for U.S. Appl. No. 15/933,578, dated Aug. 7, 2019.
Notice of Allowance for U.S. Appl. No. 15/933,578, dated Dec. 9, 2019.
Notice of Allowance for U.S. Appl. No. 15/933,578, dated Feb. 3, 2020.
Notice of Allowance for U.S. Appl. No. 16/830,666, dated Oct. 13, 2020.
Request for Inter Partes Reexamination, U.S. Appl. No. 95/001,896, filed Feb. 16, 2012.
Order Granting/Denying Request for Inter Partes Reexamination, U.S. Appl. No. 95/001,896, mailed Apr. 3, 2012.
Office Action in Inter Partes Reexamination, U.S. Appl. No. 95/001,896, dated Apr. 3, 2012.
Response to Office Action in Inter Partes Reexamination, U.S. Appl. No. 95/001,896, filed Jun. 4, 2012.
Thirty-Party Comments in Response to Patent Owner's Proposed Amendment and Response, U.S. Appl. No. 95/001,896, filed Jul. 5, 2012.
Office Action in Inter Partes Reexamination, U.S. Appl. No. 95/001,896, dated Aug. 21, 2012.
Petition in Inter Partes Reexamination, U.S. Appl. No. 95/001,896, mailed Sep. 12, 2012.
Response to Office Action in Inter Partes Reexamination, U.S. Appl. No. 95/001,896, filed Sep. 21, 2012.
Third-Party Requester's Opposition to Patent Owner's Petition for Supervisory Review, U.S. Appl. No. 95/001,896, filed Sep. 27, 2012.
Thirty-Party Comments Regarding Patent Owner's Response to Action Closing Prosecution and Proposed Amendment, U.S. Appl. No. 95/001,896, filed Oct. 22, 2012.
Patent Owner's Request to Expunge Comments, U.S. Appl. No. 95/001,896, filed Nov. 13, 2012.
Third-Party Requester's Opposition to Patent Owner's Request to Expunge Comments, U.S. Appl. No. 95/001,896, filed Nov. 27, 2012.
Action Closing Prosecution, U.S. Re-examination No. 95/001,896, dated Aug. 22, 2013.
Response to Action Closing Prosecution and Proposed Amendment Under 37 C.F.R. 1.530 and 1.943, U.S. Re-examination No. 95/001,896, dated Sep. 23, 2013.
Replacement Corrected Claims and Table of Contents, U.S. Re-examination No. 95/001,896, dated Sep. 26, 2013.
Petition under 37 CFR 1.181 for Review of Decision in ACP Entering Patent Owner's Improper Amendment of the Patent, U.S. Reexamination No. 95/001,896, dated Oct. 7, 2013.
Third Party Comments Regarding Patent Owner's Response to Second Action Closing Prosecution and Proposed Amendment, U.S. Re-examination No. 95/001,896, dated Oct. 22, 2013.
Patent Owner's Opposition to Requester's Petition for Review of the Primary Examiner's Entry of Patent Owner's Amendment, U.S. Re-examination No. 95/001,896, dated Oct. 31, 2013.
Patent Owner's Opposition to Entry of Declaration, U.S. Reexamination No. 95/001,896, dated Dec. 6, 2013.
Third Party Requester's Opposition to Patent Owner's Request to Expunge Prior Art and Expert Declation, U.S. Reexamination No. 95/001,896, ddated Dec. 18, 2013.
Decision on Petitions, U.S. Reexamination No. 95/001,896, dated Jan. 24, 2014.
Right of Appeal Notice, U.S. Reexamination No. 95/001,896, dated Feb. 7, 2014.
Patent Owner's Appeal Brief, U.S. Reexamination No. 95/001,896, filed May 19, 2014.
Third-Party Requester's Brief in Cross Appeal, U.S. Reexamination No. 95/001,896, filed May 16, 2014.
Respondent Brief for Cross Appeal (Patent Owner), U.S. Reexamination No. 95/001,896, filed Jun. 19, 2014.
Third-Party Requester's Respondent Brief, U.S. Reexamination No. 95/001,896, filed Jun. 19, 2014.
Examiner's Answer, U.S. Reexamination No. 95/001,896, dated Oct. 31, 2014.
Patent Owners' Rebuttal Brief, U.S. Reexamination No. 95/001,896, filed Dec. 1, 2014.
Rebuttal Brief (Patent Owner), U.S Reexamination No. 95/001,896, filed Dec. 1, 2014.
Decision on Appeal, U.S. Reexamination No. 95/001,896, dated Sep. 29, 2015.
Request for Rehearing (Patent Owner), U.S. Reexamination No. 95/001,896, filed Nov. 24, 2015, pp. 1-8.
Third-Party Requester's Response to Patent Owner's Request for Rehearing, U.S. Reexamination No. 95/001,896, filed Dec. 23, 2015, pp. 1-6.
Decision on Request for Rehearing, U.S. Reexamination No. 95/001,896, dated Apr. 1, 2016.
Patent Owner's Notice of Appeal, U.S. Reexamination No. 95/001,896, dated May 26, 2016.
Petition to Proceed with CAFC Appeal or to Reissue Board Decision, U.S. Reexamination No. 95/001,896, dated Jul. 5, 2016.
Third Party's Response in Opposition to Patent Owner's Petition to Proceed with CAFC Appeal, U.S. Reexamination No. 95/001,896, dated Aug. 2, 2016.
Decision Expunging Improper Documents in Inter Partes Reexamination, U.S. Reexamination No. 95/001,896, dated Aug. 12, 2016.
Memorandum and Order, U.S. Reexamination No. 95/001,896, dated Oct. 3, 2016.
Decision on Petitions, U.S. Reexamination No. 95/001,896, dated Apr. 4, 2017.
Notice of Intent to Issue Reexam Certificate, U.S. Reexamination No. 95/001,896, dated Jul. 11, 2017.
Notice of CAFC Order to Consider Petition (Patent Owner), U.S. Reexamination No. 95/001,896, dated Oct. 6, 2016.
Petitioner's Reply Brief, IPR2014-00833, Re U.S. Pat. No. 8,725,165, filed Apr. 21, 2015, pp. 1-22.
Petition for Inter Partes Review Re U.S. Pat. No. 8,725,165, filed May 30, 2014.
Patent Owner's Preliminary Response, IPR2014-00833, Re U.S. Pat. No. 8,725,165, filed Sep. 9, 2014.
Decision, Institution of Inter Partes Review, IPR2014-00833, Re U.S. Pat. No. 8,725,165, dated Dec. 3, 2014, pp. 1-26.
Patent Owner's Request for Rehearing, IPR2014-00833, Re U.S. Pat. No. 8,725,165, filed Dec. 17, 2014, pp. 1-16.
Patent Owner's Response, IPR2014-00833, Re U.S. Pat. No. 8,725,165, filed Feb. 18, 2015, pp. 1-49.
Decision, Patent Owner's Request for Rehearing, IPR2014-00833, Re U.S. Pat. No. 8,725,165, dated Feb. 20, 2015, pp. 1-8.

(56) References Cited

OTHER PUBLICATIONS

Final Written Decision, IPR2014-00833, Re U.S. Pat. No. 8,725,165, filed Nov. 20, 2015, pp. 1-28.
Patent Owner's Request for Rehearing, IPR2014-00833, Re U.S. Pat. No. 8,725,165, filed Dec. 20, 2015, pp. 1-24.
FedEx Answer, Affirmative Defenses and Counterclaims, C.A. 4:14-cv-04894-PJH, filed Feb. 2, 2015, pp. 1-9.
Decision on Patent Owner's Request for Rehearing, IPR2014-00833, Re U.S. Pat. No. 8,725,165, dated Feb. 12, 2016, pp. 1-11.
Decision & Judgement (Rule 36), CAFC Appeal No. 2016-1911, May 9, 2017.
Reply Brief of Appellant, CAFC Appeal No. 2016-1911, Oct. 20, 2016.
Brief of Appellee, CAFC Appeal No. 2016-1911, Oct. 6, 2016.
Brief of Appellant, CAFC Appeal No. 2016-1911, Jul. 27, 2016.
"352C22 Miniature Low Profile ICP Accelerometer," Precision Accelerometers, PCB Piezoelectronics Products—SVS Division, webpages, pp. 1-2 (downloaded Apr. 11, 2002: www.pcb.com/products/svs/svs352c22.html).
"3G Mobile Internet Revolution, . . . only with Location Based Services!" pp. 1, (downloaded Aug. 10, 2002: http://webhome.idirect.com/~dental/3glocator/home.htm).
"Airline Cargo Containers," Case Study, RJI Incorporated, webpages, pp. 1-2 (downloaded Mar. 16, 2002: www.rji.cc/casestudies/airlinecargocontainers.html).
"Airline Food Carts," Case Study, RJI Incorporated, webpages, pp. 1-2 (downloaded Mar. 16, 2002: www.rji.cc/casestudies/airlinefoodcarts.html).
"An Introduction to SnapTrack Server-Aided GPS Technology," SnapTrack Inc., Apr. 3, 2007.
Archived copy of a page entitled "Money-Back Guarantee Policy" from fedex.com, archived by the Internet Archive on Aug. 17, 2000.
"Audiovox Intros GPS, Bluetooth Phone;" INT Media Group, Inc. (allNetDevices), Apr. 5, 2002. (downloaded: www.allnetdevices.com/wireless/news/2001/1/15/audiovox_intros.html).
Bahl et al. "RADAR: An In-Building RF-based User Location and Tracking System," *Proc. of the IEEE Conf. on Comp. Comm., INFOCOM2000, 19th Annual Joint Conf. of the IEEE Computer and Communications Societies*, Mar. 2000, 10 pgs.
Benefon Esc! Owner's Manual, Publication No. YZ2400-4*, © Benefon Oyj, 2002, pp. 169.
"Carrier and end-user applications for wireless location systems," TruePosition, Inc., http://www.trueposition.com/spie_app.htm, downloaded, Jul. 30, 2000, pp. 1-7.
Capozza, P.T., et al. "A single-chip narrow-band frequency domain excisor for a Global Positioning System (GPS) receiver," IEEE Journal of Solid-State Circuits, vol. 35, Issue 3, Mar. 2000, pp. 401-411.
"Danger—Products" and "Hiptop Communicator Brochure," Danger, Inc., downloaded Oct. 26, 2002: www.danger.com/products.php).
"Developing a GPSs for the Global Supply Chain," Aberdeen Group, Inc., Executive White Paper, Jun. 2002.
"Devices for Text Messages in Deutsche Telekom's fixed network have already found their way into many households," Deutsche Telekom AG, Press Release, Mar. 13, 2002, pp. 1-2.
"Digital/Analog Compass Sensors" and "1655 Digital Compass Sensor," webpages, The Robson Company, Inc., pp. 1-2 (downloaded Apr. 11, 2002: www.dinsmoresensors.com/index.html).
"EarthTrack™ Vehicle Tracking Systems," Outfitter Satellite, Inc., 1998 (downloaded Jan. 22, 2000).
"Enhanced Tracking," United Parcel Service of America, Inc. (UPS), webpages, pp. 1-2 (downloaded Jun. 1, 2002: www.ups.com/myupsinfo/info/etrack?pnav=stdservice).
"Fleet Management Systems—Asset Tracking Devices," Axiom Navigation Inc., 2000-2001 (downloaded Oct. 19, 2002: www.axiomnav.com/Prod_Systems/prod_system.asp).
"Frozen Food Warehouse," Case Study, RJI Incorporated, webpages, pp. 1-3 (downloaded Mar. 16, 2002: www.rji.cc/casestudies/frozenfoodwarehouse.html).

"FunMail Launches on the NTT DoCoMo i-mode network," FunMail, Press Release, May 1, 2001, pp. 1-2.
Garmin, eTrex® Venture personal navigator™: Owner's Manual and Reference Guide, © 2001 Garmin, pp. 1-68.
"Global Cell Phone Location," Axiom Navigation Inc., 2000-2001 (downloaded Oct. 19, 2002: www.axiomnav.com/Prod_Global/prod_global.asp).
"Global Locating Services," SkyBitz, webpage, p. 1, (downloaded Nov. 15, 2002: www.skybitz.com/services/gls.html).
"GLS Communicator," SkyBitz, webpages, pp. 1-2, (downloaded Nov. 15, 2002: www.skybitz.com/gls/communicator.html).
"Guide to Tracking Info.," Nippon Express, website page, p. 1 (downloaded Jun. 9, 2002: www.nittsu.co.jp/edoc/howtoe.htm).
Heinrichs et al. "Synergies in Handset Architecture," *GPS World*, Mar. 2002, vol. 13, Issue 3, p. 30-39.
Hightower et al. "Location Systems for Ubiquitous Computing," *Computer*, Aug. 2001, vol. 34, Issue 8, p. 57-66.
"Introduction to SMS," by C. Tull of Anywhere YouGo.com, pp. 1-4 (downloaded:www.devx.com/wireless/articles/SMS/SMSintro-asp), Aug. 10, 2002.
"IO Data Develops GPS Adapter for I-Mode Mobile," AsiaBizTech, Sep. 17, 2002, pp. 1-2.
LaMance et al. "Assisted GPS," *GPS World*, Mar. 2002, vol. 13, Issue 3, p. 46-51.
"Locate Networks: Our Service," Locate Networks, webpages, pp. 1-7 (downloaded Sep. 26, 2002: www.locatenetworks.com/).
"MMS phones: Don't believe the hype," CNN.com/SCI-TECH, Aug. 8, 2002, pp. 1-3.
"Mobile Location Based Services: Cell Tracking Devices of People & Thongs . . . ," pp. 1-2, (downloaded Aug. 10, 2002: http://3glocate.com).
"MoniTrack," Case Study, RJI Incorporated, webpages, pp. 1-2 (downloaded Mar. 16, 2002: www.rji.cc/technology/telematic.html).
"My ups.com Benefits," United Parcel Service of America, Inc. (UPS), webpage, p. 1 (downloaded Apr. 13, 2002: www.ups.com/myupsinfo/info/benefits?pnav=stdsservice).
"NavMate® Navigation System," Visteon Corporation, webpage, pp. 1-2 (downloaded Jun. 21, 2002: www.visteon.com/technology/automotive/navmate.html).
"News," SkyBitz, webpages, pp. 1-8, (downloaded Nov. 15, 2002: www.skybitz.com/about/news.html).
"Pakhound: Your Watchdog In The Shipping Industry," website pages, pp. 1-3 (downloaded Jun. 9, 2002: www.pakhound.com/fact.asp).
Palenchar, J. "E911 Update: What Major Carriers Have Planned," *TWICE: This Week in Consumer Electronics*, Oct. 8, 2001, vol. 16, Issue 23, p. 36.
"Parkwatch and Wherenet Unveil the First Amusement Visitor Locating system," ParkWatch, Press Release, Jun. 27, 2000.
"pulver.com's Location Based Services Report," pulver.com, Inc., Oct. 2001, pp. 1-17 (downloaded Jun. 4, 2002: www.pulver.com/lbsreport/lastbsreport.02/oct01 .txt).
"Radio Frequency Identification (RFID)," Case Study, RJI Incorporated, webpage, p. 1 (downloaded Mar. 16, 2002: www.rji.cc/technology/rfid.html).
"Real Time Location System (RTLS)," Case Study, RJI Incorporated, webpage, p. 1 (downloaded Mar. 16, 2002: www.rji.cc/technology/rtls.html).
"Real-Time Warehouse Tracking," Case Study, RJI Incorporated, webpages, pp. 1-2 (downloaded Mar. 16, 2002: www.rji.cc/casestudies/rtwarehousetracking.html).
"Savi Reusable Transport Container," Savi Technology, Inc., Apr. 30, 2002, pp. 1-2.
"Send images to i-mode phones," Mobile Media Japan, 2001, pp. 1-3.
"Ski Rental with Auto ID and Tracking," Case Study, RJI Incorporated, webpages, pp. 1-2 (downloaded Mar. 16, 2002: www.rji.cc/casestudies/skirentalcompany.html).
"SnapTrack and SignalSoft Corp. Team Up to Trial Location-based Information Service for GSM Test Group," Press Release, SnapTrack Inc., Dec. 6, 1999.

(56) References Cited

OTHER PUBLICATIONS

"SnapTrack Awarded Additional Key Patents for Enhanced GPS System," Press Release, SnapTrack Inc., Jan. 4, 2000.
"Start-up crams single chip with phone, GPS and Bluetooth," CNET Network, Inc. (ZDNET), Mar. 22, 2002 (downloaded: http://news.zdnet.co.uk/story/0,t284-x2107163,00.html).
"Status Icons/Messages," Yahoo! Messenger Help, Yahoo! Inc., 2002, pp. 1-2.
Syrjarinne, J. "Keeping Time with Mobiles," *GPS World*, Jan. 2001, vol. 12, Issue 1, p. 22, 7pgs.
"Technical Applications Of Our Current Technology," Aetherwire, webpages, pp. 1-4 (downloaded Mar. 16, 2002: www.aetherwire.com/CDROM/General/appl1.html).
"The Always on Network," Position Paper, Nortel Networks, 2002.
"Theme Park Visitors & Cashless Purchasing," Case Study, RJI Incorporated, webpages, pp. 1-2 (downloaded Mar. 16, 2002: www.rji.cc/casestudies/themepark.html).
"Track Shipments—Detailed Results," FedEx, webpages, pp. 1-2 (downloaded Oct. 29, 2002: www.fedex.com).
"Track Your FedEx Shipments via Email," FedEx, webpages, pp. 1-2 (downloaded Oct. 29, 2002: www.fedex.com).
"Tracking Helpful Tips," United Parcel Service of America, Inc. (UPS), webpages, pp. 1-2 (downloaded Jun. 1, 2002: www.ups.com/tracking/nm_help.html).
"Trimble and Rosum Team to Develop Universal Positioning Technology," Trimble Navigation, Inc., News Release, Feb. 27, 2003.
"Turning Position Into Knowledge," SkyBitz, webpage, p. 1, (downloaded Nov. 15, 2002: www.skybitz.com).
"UPS Package Tracking," United Parcel Service of America, Inc. (UPS), webpages, pp. 1-2 (downloaded Apr. 13, 2002: www.ups.com/tracking/tracking.html).
"UPS Wireless Solutions," United Parcel Service of America, Inc. (UPS), webpage, p. 1 (downloaded Apr. 13, 2002: www.ups.com/myupsinfo/info/wireless?pnav=stdsservice).
Van Diggelen et al. "Indoor GPS," *GPS World*, Sep. 2001, vol. 12, Issue 9, p. 50. 5pgs.
"Welcome to Iship, Inc.," iShip, Inc., webpages, pp. 1-2, (downloaded Jun. 9, 2002: www.iship.com/).
"Welcome to Traker Systems," Tracker Systems, webpages, pp. 1-2 (downloaded Jun. 9, 2002: www.trakersystems.com).
"What are Instant Messages?" Yahoo! Messenger Help, Yahoo! Inc., 2002, pp. 1.
"What is "3G" technology?," CNN.com/SCI-TECH, Oct. 22, 2001, pp. 1-3.
"What is a Friend List?" Yahoo! Messenger Help, Yahoo! Inc., 2002, pp. 1.
"Wherify Wireless and SiRF Team to Deliver Child Locator System," Wherify Wireless, Inc., Press Release, Mar. 19, 2001, pp. 1-2.
"Wherify Wireless Breakthrough in Location-Based Services," Mobilemag.com, Feb. 28, 2001, p. 1.
"Wherify Wireless GPS Locator for Kids User Guide," Wherify Wireless, Inc., 2003, pp. 1-106.
"Wherify Wireless Location Services," Wherify Wireless, Inc., webpages, pp. 1-5 (downloaded: Mar. 25, 2003: www.wherifywireless.com/prod_watches.htm).
"X-GPS™—Hybrid GPS Location Server Solution," Axiom Navigation Inc., 2000-2001 (downloaded Oct. 19, 2002: www.axiomnav.com/Prod_Global/x-gps.asp).
"Yahoo! Messenger—Sending Messages to a Mobile Phone," Yahoo! Messenger, Yahoo! Inc., 2002, pp. 1-7 (downloaded Oct. 27, 2002: http://messenger.yahoo.com/messenger/wireless/pc2sms/tour1.html(through /tour7.html)).
"Yahoo! Messenger for Text Messaging," Yahoo! Messenger, Yahoo! Inc., 2002, pp. 1-10 (downloaded Oct. 27, 2002: http://messenger.yahoo.com/messenger/wireless/smsmsgr/tour1.html (through /tour7.html)).
"Yahoo! Messenger for WAP," Yahoo Messenger, Yahoo! Inc., 2002 (tours 1-9), pp. 1-17 (downloaded Oct. 27, 2002: www.messenger.yahoo.com/messenger/wireless/wap/tour1.html(through /tour9.html)).

Accelerometers—General Purpose, LP Series, Crossbow Technology, Inc., data sheet, pp. 1-3 (downloaded Apr. 11, 2002: www.xbow.com/Products/Accelerometers.htm).
Bickers, "Eyes in the sky," SafeTzone Technology Corporation, webpages, 2001, pp. 1-3 (downloaded: www.safetzone.com/newsKiosk.asp).
Chertkoff, Rachel, "Vehicle Locator Systems," Pager Technology, pp. 1-2, 1998.
Commercial Uses for LoJack (webpage), LoJack Corporation, downloaded Jan. 22, 2000.
Crossbow Product Guide—Accelerometers, Crossbow Technology, Inc., webpages, pp. 1-3 (downloaded Apr. 11, 2002: www.xbow.com/Products/Accelerometers.htm).
Culler, D. et al., "MICA: The Commercialization of Microsensor Motes," Sensors (Apr. 1, 2002), pp. 1-5.
Darabi et al., "A 2.4-GHz CMOS Transceiver for Bluetooth," IEEE Journal of Solid-State Circuits, vol. 36, No. 12 (Dec. 2001), pp. 2016-2024.
Delphi and MobileAria Demonstrate True Hands Free In-Vehicle Mobile Productivity Services At CES, Press Release, Delphi Automotive Systems, Jan. 8, 2002 (downloaded Apr. 5, 2002: www.delphiauto.com/news/pressRelease/pr6828-01082002).
F. Rivera, "Special Report: Keeping Tabs on Your Teen," 7 News, Boston, Apr. 30, 2002, pp. 1-3.
FedEx Insight, FedEx, webpages, pp. 1-11 (downloaded Oct. 29, 2002: www.fedex.com).
Fraden, J., Handbook of Modern Sensors: Physics, Designs and Applications, Second Edition, Springer-Verlag (1996), cover, pp. 310-354, 384-431, 458-493, and 513-528.
GPS2000, Omega Research and Development, Inc., webpages, pp. 1-9 (pp. 7-9 pertain to an online tour) (downloaded Jul. 14, 2003: www.gps2000online.com/).
Grimes, et al., "Wireless Magnetoelastic Resonance Sensors: A Critical Review," Sensors, vol. 2 (Jul. 23, 2002), pp. 294-313.
Helfenstein et al., Circuits and Systems for Wireless Communications, Kluwer Academic Publishers (2000), cover pages, pp. 3-7, 9-34, and 37-47.
Hill et al., "System Architecture Directions for Networked Sensors," ACM/ASPLOS-IX (Nov. 2000), 12 pages.
IMVironment, Yahoo! Messenger Yahoo! Inc., 2002, pp. 1-12 (downloaded (including) Oct. 27, 2002: http://help.yahoo.com/help/us/mesg/imv/imv-01.html(through/index5.html).
J.Wrolstad, "Chrysler Claims First With Bluetooth Mobile Phone System," Wireless Newsfactor, Oct. 26, 2001.
K. Hill, "Prada Uses Smart Tags To Personalize Shopping," CRMDaily.com, Apr. 24, 2002., pp. 1-4.
Madou, Marc J., Fundamentals of Microfabrication: the Science of Miniaturization, Second Edition, CRC Press (2002) 139 pages.
K. Miyake, "Sharp to unveil 3G PDA-type cell phone," ITworld.com, Inc., Jan. 11, 2002.
Kleinknecht, William, "Juvenile authorities want satellite tracking for felons," The Star-Ledger of New Jersey, Nov. 18, 1997.
LoadTrak, pp. 1-2 (downloaded Jun. 4, 2002: www.load-trak.com).
Mainwaring et al., "Wireless Sensor Networks for Habitat Monitoring," ACM (Sep. 28, 2002) pp. 88-97.
Marek, "The Unstoppable SnapTrack," Wireless Week, Dec. 18, 2000.
Motorola Consumer Catalog: Pagers (webpage), Motorola, Inc., downloaded Jan. 19, 2000.
My.Roadway!, Roadway Express, Inc., webpages, pp. 1-2, (downloaded Jun. 9, 2002: www.quiktrak.roadway.com/cgi-bin/quiktrak).
Package, Dictionary.com, http://dictionary.reference.com/browse/package (last accessed Nov. 6, 2013), 3 pgs.
"Package" definition, Oxford English Dictionary (OED) Online, Oxford University Press, Jun. 2014 (printed Aug. 1, 2014).
"Portable" definition, Oxford English Dictionary (OED) Online, Oxford University Press, Jun. 2014 (printed Aug. 1, 2014).
Packtrack™, PackTrack.com, webpages, pp. 1-2 (downloaded Jun. 9, 2002: www.packtrack.com).
Precision Accelerometers, PCB Piezoelectronics Products—SVS Division, webpages, pp. 1-2 (downloaded Apr. 11, 2002: www.pcb.com/products/svs/index.html).

(56) References Cited

OTHER PUBLICATIONS

Rabinowitz and Spilker, Jr., "A New Positioning System Using Television Synchronization Signals," Rosum Corporation, pp. 1-11 (downloaded May 21, 2003).
Rabinowitz and Spilker, Jr., "Positioning Using the ATSC Digital Television Signal," Rosum Corporation Whitepaper, Rosum Corporation (downloaded May 21, 2003).
Razavi, Behzad, RF Microelectronics, Prentice Hall (1998), cover pages, pp. 1-10, and 118-297.
Real Time Locating System, Executive Summary, Technology Systems International, Inc., 2007.
Rofougaran et al., "A Single-Chip 900-MHz Spread-Spectrum Wireless Transceiver in 1-μm CMOS-Part II: Receiver Design," IEEE Journal of Solid-State Circuits, vol. 33, No. 4 (Apr. 1998), pp. 535-547.
Ryan, "Catching up with Dick Tracy," San Francisco Chronicle, news article, Mar. 18, 2002.
SandPiper GPS Receiver, Specification sheet by Axiom Navigation Inc. (www.axiomnav.com) 2006.
Senturia, Stephen D., Microsystem Design, Kluwer Academic Publishers (2001), cover pages, and pp. 3-14.
SiRF Debuts Revolutionary Architecture and Technologies to Further Drive GPS into the Mainstream, SiRF.com, Aug. 16, 1999 (archived Dec. 22, 1999), http://web.archive.org/web/19991222194810/http:/www.sirf.com/as_prss2_3.htm, 4 pgs.
Smart Antenna, Specification sheet by Axiom Navigation Inc. (www.axiomnav.com) 2008.
SnapTrack—Privacy Protection (webpage), SnapTrack Inc., downloaded Jan. 19, 2000.
SnapTrack—Technology At Work (webpage), SnapTrack Inc., downloaded Jan. 19, 2000.
SnapTrack in Action (webpage), SnapTrack Inc., downloaded Jan. 19, 2000.
Steyaert et al., "A 2-V CMOS Cellular Transceiver Front-End," IEEE Journal of Solid-State Circuits, vol. 35, No. 12, Dec. 2000, pp. 1895-1907.
Stilp, Louis A., "Examining the Coming Revolution in Location Services," pp. 1-11, Nov. 19, 2020.
Strom, Stephanie. "A Wild Sleigh Ride at Federal Express," The New York Times, Dec. 20, 1994.
Swift A2 GPS Receiver, Specification sheet by Axiom Navigation Inc. (www.axiomnav.com) 2010.
Swift B2 GPS Receiver, Specification sheet by Axiom Navigation Inc. (www.axiomnav.com) 2010.
TruePosition Virtual Brochure (webpage), TruePosition, Inc. Nov. 19, 2020.
Wong, "Fishers, golfers join the rush to GPS," San Jose Mercury News, news article, Mar. 25, 2002.
Danger Product Overview, Danger, Inc., date unknown, 5 pgs, Nov. 19, 2020.
PCVtrak™ Installation and Operator's Manual, Trimble Navigation, 24623-00 Rev. A, May 1994, pp. 1-259.
"Advanced Traveler Aid Systems for Public Transportation," Final Report, Federal Transit Administration, Sep. 1994, pp. 1-131.
Campbell, Laurel, "SECURITY—Military satellite enlisted to thwart car crime," The Commercial Appeal, Sep. 26, 1996, pp. 5B.
Law, Alex, "Week in Wheels/. . . From a Driver's Notebook," Newsday, Inc., Sep. 20, 1996, pp. C03.
Cortez, Angela, "Springs police can track thief, vehicles," The Denver Post, Sep. 10, 1996, pp. B-01.
"OnGuard Tracker Nabs Auto Burglar," Global Positioning & Navigation News, vol. 6, No. 16, Aug. 8, 1996.
"OnGuard Tracker Nabs Auto Burglar," Section: Financial News, PR Newswire, Jul. 29, 1996.
Nauman, Matt, "Pressing the Panic Button: Car Security Enters a New Age with Cellular Phones and Satellites that Watch Over You," San Jose Mercury News, Jun. 21, 1996, pp. 1G.
"Monday Briefing" San Antonio Express—News, p. 1, Part B, Jun. 10, 1996.

"OnGuard Tracker Makes Debut on 'One Lap of America'," PR Newswire, Jun. 7, 1996.
"OnGuard Tracker Makes Debut on 'One Lap of America'," Southwest Newswire, Jun. 7, 1996.
Dominguez, Raul, "Women get their day in sun—American Golf planning events nationwide May 18," San Antonio Express—News, Apr. 18, 1996, pp. 2, part B.
"Vehicle Navigation Units Being Measured in Luxury Autos," Global Positioning & Navigation News, vol. 6, No. 7, Apr. 4, 1996.
"Advanced Business Sciences, Inc. Announces Completion of Acquisition of Comguard of Illinois," Business Wire, Aug. 26, 1998.
"Advanced Business Sciences, Inc. Announces Filing With Securities and Exchange Commission," Business Wire, Jun. 25, 1999.
"Advanced Business Sciences, Inc. Announces Preliminary Fourth Quarter 1998 Revenue Results," Business Wire, Feb. 4, 1999.
"Business People Burnsy's Grill Names Two," Omaha World-Herald, Section Business, p. 4M, Oct. 20, 1996.
"Company Sees Prisoner Tracking and Monitoring Market Niche," Global Positioning & Navigation News, vol. 6, No. 10, May 16, 1996.
GPS-Based Personal Monitoring Systems Offered to Corrections, Private Market, Global Positioning & Navigation News, vol. 8, No. 11, Jun. 3, 1998.
GPS tracks parolees, probationers, Corrections Professional, vol. 5, No. 6, Nov. 19, 1999.
High-Tech System Tracks Offenders—Satellites Watching Criminals, Business Wire, Nov. 14, 1997.
Briefs, Global Positioning & Navigation News, vol. 9, No. 4, Feb. 24, 1999.
Dunkelberger, Lloyd, "Lawmakers question criminal-tracking system," Sarasota Herald-Tribune (Florida), pp. 16A, Nov. 28, 1999.
Powell, Barbara. "New gadgets help drivers find their way," Fort Worth Star-Telegram (Texas), p. 1, Jan. 20, 1997.
"New Service Lets Corrections Agencies Track Offenders By Satellite," PR Newswire, Jan. 11, 1999.
"New Service Lets Corrections Agencies Track Offenders by Satellite; SecutityLink Offers "GPS" Tracking for Offenders on Electronic Monitoring—Sandusky Municipal Court Adopts Technology for Local Offenders," PR Newswire, Jan. 12, 1999.
"New Service Lets Corrections Agencies Track Offenders by Satellite; SecurityLink Offers 'GPS' Tracking for Offenders on Electronic Monitoring," PR Newswire, Section: Financial News, Jan. 11, 1999.
"New Service Lets Corrections Agencies Track Offenders By Satellite," Satellite Today, vol. 2, No. 8, Jan. 13, 1999.
"Prisoner Security Monitoring Company Grabs Contracts for GPS-Based System," Global Positioning & Navigation News, vol. 7, No. 1, Jan. 15, 1997.
Atwater, Andi, "Proposal seeking 24-hour tracking of all sex offenders," The News-Press (Fort Meyers, FL), pp. 1A, Feb. 20, 2000.
Briefs, Global Positioning & Navigation News, vol. 9, No. 3, Feb. 10, 1999.
Brauer, David, "Satellite 'Big Brother' Tracks Ex-Inmates; Agencies Experiment with GPS to Monitor Parolee Whereabouts," Chicago Tribune, Section: News, p. 31, Dec. 18, 1998.
"Satellite Spotlight; Eye in the Sky to Monitor Parolees," Satellite News, vol. 21, No. 15, Apr. 13, 1998.
"Satellite Spotlight: Fighting Crime From Space," Satellite News, vol. 19, No. 20, May 13, 1996.
Prohaska, Thomas J, "Satellite Will Keep Tabs on Convicts," Buffalo News (New York), Section: Local, p. 5B, Sep. 20, 1999.
"Sierra Wireless and Pro Tech Team Up on Monitoring Product," Global Positioning & Navigation News, vol. 8, No. 8, Apr. 22, 1998.
Anderson, Larry, "Technology rules at Securing New Ground," Access Control & Security Systems Integration, Section: Industry Outlook; ISSN 1084-6425, Dec. 1999.
Trimble Navigation Warns 2nd-Quarter Earnings to Miss Target, Dow Jones Business News, Jul. 10, 1998.
"Trimble Navigation's Net Income Skidded 93% Amid Order Delays," Dow Jones Business News, Jul. 23, 1998.
Briefs, Global Positioning & Navigation News, vol. 9, No. 2, Jan. 27, 1999.

(56) References Cited

OTHER PUBLICATIONS

Briefs, Global Positioning & Navigation News, vol. 9, No. 14, Jul. 14, 1999.
Dailey et al. "Automatic Transit Location System," Final Research Report, 55 pgs., Feb. 1996.
Maguire, Jr. et al. "SmartBadges: a wearable computer and communication system," codes/CASHE '98, 47 pgs., 1998.
Koshima et al. "Personal locator services emerge," IEEE Spectrum, Feb. 2000, pp. 41-48.
Zygowicz et al. "State of the Art in Automatic Vehicle Location Systems," Center for Urban Transportation Studies, University of Wisconsin, Milwaukee, Feb. 1998.
Ashworth, Jon. "Big brother is watching you," The Times (London), Section: Features, May 7, 1999.
"Car Thieves Take the "Bait" in Michigan; Two Suspects Reeled in With OnGuard," Business Wire, Sep. 11, 1997.
Sauer, Matthew, "Company Finds Niche By Giving Directions . . . " Sarasota Herald-Tribune (Florida), Section: Business Weekly, p. 1, Jul. 7, 1997.
"ATX Technologies Signs Nationwide Service Deal with AT&T," Global Positioning & Navigation News, vol. 7, No. 9, May 7, 1997.
"Car Thieves Take the 'Bait' in Tulsa; Two Suspects Caught Off Guard with OnGuard Once Again," PR Newswire, Section: Financial News, Jan. 8, 1997.
"Car Thieves Take the 'Bait' in Tulsa; Two Suspects Caught Off Guard with On Guard," PR Newswire, Section: Financial News, Dec. 9, 1996.
Jackson, Terry, "Smart Cars Whether By Satellite or the Internet, High-Tech Devices and Services May Make Crumpled Road Maps A Thing of the Past," The Miami Herald, Section: Travel, p. 1J, Oct. 6, 1996.
"San Antonio Personal Security Company Links Up with Senior PGA Golfer," PR Newswire, Section: Financial News, Apr. 1, 1996.
"San Antonio Personal Security Company Links Up with Senior PGA Golfer," Southwest Newswire, Apr. 1, 1996.
Business Briefs, San Antonio Express—News, Mar. 25, 1996.
"ATX Research Signs Exclusive Sales Agreement with Arizona Company," PR Newswire, Mar. 21, 1996.
"ATX Research Signs Exclusive Sales Agreement with Arizona Company,"Southwest Newswire, Mar. 21, 1996.
"Automotive GPS Satellite/Safety System Race Is On," Southwest Newswire, Feb. 20, 1996.
"Dealerships Can Track Down New Aftermarket Revenues," PR Newswire, Feb. 9, 1996.
"ATX Research Unveils New Stealthtrac Capability," PR Newswire, Feb. 9, 1996.
"Dealerships Can Track Down New Aftermarket Revenues," Southwest Newswire, Feb. 9, 1996.
Briefs, Global Positioning & Navigation News Wire, vol. 6, No. 2, Jan. 24, 1996.
"ATX Research Provides Police Departments With Onguard Personal Security and Vehicle Tracking System," PR Newswire, Jan. 15, 1996.
"ATX Research Provides Police Departments With Onguard Personal Security and Vehicle Tracking System," Southwest Newswire, Jan. 15, 1996.
"ATX Research Relocates to New Corporate Headquarters," PR Newswire, Dec. 12, 1995.
"ATX Research Relocates to New Corporate Headquarters," Southwest Newswire, Dec. 12, 1995.
"Texas invention tracks stolen cars, lets driver call for help," The Vancouver Sun, Oct. 20, 1995.
"San Antonio Company Unveils Satellite/Cellular Personal Security System," PR Newswire, Oct. 3, 1995.
"San Antonio Company Unveils Satellite/Cellular Personal Security System," Southwest Newswire, Oct. 3, 1995.
Office Action for U.S. Appl. No. 16/830,666, dated Mar. 31, 2021.

* cited by examiner

NOTIFICATION SETUP

NOTIFICATION CHANNEL:

☐ EMAIL  ☐ PAGE  ☐ FAX

602

DESTINATION(S):

[                    ]

604

NOTIFICATION CRITERIA: 606

☐ POSITION
- ☐ PERIODIC, EVERY [DAY ▼]
- ☐ DISTANCE, EVERY [100 Mi ▼]

☐ ON-DELIVERY
- ☐ DELIVERED  ☐ IMPENDING DELIVERY

☐ CONDITIONS
- ☐ PERIODIC, EVERY [DAY ▼]
- ☐ EXTREME CONDITIONS
  - ☐ TEMPERATURE > [  ] °F
  - ☐ FORCE > [  ] LBS

FIG. 6

METHOD AND SYSTEM FOR TRACKING AND MONITORING ASSETS

CROSS REFERENCE TO RELATED APPLICATIONS

This application is a Continuation of U.S. patent application Ser. No. 16/830,666, filed Mar. 26, 2020, and entitled "TRACKING MOVEMENT OF OBJECTS AND NOTIFICATION THEREFOR," which is hereby incorporated herein by reference, which in turn is a Continuation of U.S. patent application Ser. No. 15/933,578, filed Mar. 23, 2018, and entitled "METHOD AND SYSTEM FOR PROVIDING SHIPMENT TRACKING AND NOTIFICATIONS," now U.S. Pat. No. 10,614,408, which is hereby incorporated herein by reference, which in turn is a Continuation of U.S. patent application Ser. No. 13/802,641, filed Mar. 13, 2013, and entitled "METHOD AND SYSTEM FOR PROVIDING SHIPMENT TRACKING AND NOTIFICATIONS," which is hereby incorporated herein by reference, which in turn is a Continuation of U.S. patent application Ser. No. 12/924,470, filed Sep. 27, 2010, and entitled "METHOD AND SYSTEM FOR PROVIDING SHIPMENT TRACKING AND NOTIFICATIONS," now U.S. Pat. No. 8,725,165, which is hereby incorporated herein by reference, which in turn is a Continuation of U.S. patent application Ser. No. 11/732,581, filed Apr. 3, 2007, and entitled "METHOD AND SYSTEM FOR PROVIDING SHIPMENT TRACKING AND NOTIFICATIONS," now U.S. Pat. No. 7,809,377, which is hereby incorporated herein by reference, which in turn is a Continuation of U.S. patent application Ser. No. 10/397,637, filed Mar. 26, 2003, and entitled "METHOD AND SYSTEM FOR PROVIDING SHIPMENT TRACKING AND NOTIFICATIONS," now U.S. Pat. No. 7,212,829, which is hereby incorporated herein by reference.

By way of prior U.S. patent application Ser. No. 10/397,637, this application also claims benefit of: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

This application is also related to: (i) U.S. patent application Ser. No. 10/397,473, filed Mar. 26, 2003, and entitled "METHOD AND APPARATUS FOR INTELLIGENT ACQUISITION OF POSITION INFORMATION," now U.S. Pat. No. 6,975,941; (ii) U.S. patent application Ser. No. 10/397,472, filed Mar. 26, 2003, and entitled "Methods and Apparatus to Analyze and Present Location Information;" (iii) U.S. patent application Ser. No. 10/397,641, filed Mar. 26, 2003, and entitled "METHOD AND SYSTEM FOR PERSONALIZED MEDICAL MONITORING AND NOTIFICATIONS THEREFOR;" (iv) U.S. patent application Ser. No. 10/397,640, filed Mar. 26, 2003, and entitled "INEXPENSIVE POSITION SENSING DEVICE;" (v) U.S. patent application Ser. No. 10/397,474, filed Mar. 26, 2003, and entitled "METHOD AND SYSTEM FOR ENHANCED MESSAGING;" (vi) U.S. patent application Ser. No. 10/397,512, filed Mar. 26, 2003, and entitled "APPLICATIONS OF STATUS INFORMATION FOR INVENTORY MANAGEMENT."

BACKGROUND OF THE INVENTION

Objects are regularly shipped from a sender to a recipient. The objects can be packages, containers or boxes, or items within packages, containers or boxes. However, for the most part, once an object leaves the sender and enters a shipping channel, the sender and recipient have little or no knowledge about the shipments.

Recently, shipping companies, such as Federal Express, have enabled users to track shipments using tracking numbers uniquely assigned to the objects being shipped. A user can access the FedEx.com website and retrieve tracking information about a particular package or can arrange to have such tracking information emailed to a particular email address. The tracking information can include such information as shipment date, delivery location, delivery date/time, person acknowledging receipt, and scan activity. The scan activity provides a listing of each of the locations (and date and time) during the shipment where the package was scanned. Even more recently, FedEx introduced a Web-based business tool, referred to as FedEx InSight, to help businesses manage their shipping activities. FedEx InSight is advertised as facilitating: (i) tracking inbound, outbound and third-party payor shipments; (ii) providing notifications of critical shipping events via electronic mail, facsimile, Internet or wireless means; (iii) providing status summaries of international and domestic shipments on one report; and (iv) helping to pinpoint customs delays and delivery attempts and then suggesting ways to expedite delivery.

Notwithstanding the recent advances in tracking shipments, there still exists various problems that lead to lack of understanding of shipments activity and conditions. When scanning of packages at various locations during a route of shipment is used to tracking location, personnel must manually perform such scanning. Further, the location of packages is only known at the time that the packages are scanned at certain locations (scanning locations). In shipping a package, there is a need to have more precise and robust knowledge of the position and condition of the package throughout the shipping process.

Further, to be effective, companies have to be aware of the status of their inventory in not only their companies but also their supply-chain and/or demand-chain partners. Such information should preferably be in real time and should be precise, such as item by item. The numerous items can be located all over the globe. There is also a need for a company to be aware of the position of its inventory, preferably item-by-item, in real time.

SUMMARY

Improved approaches for tracking and monitoring status of articles are disclosed. The monitoring can produce notifications to interested parties. The notifications typically contain status information pertaining to the articles being tracked. Alternatively, interested parties can gain access to status information pertaining to the articles being tracked via a website. According to one embodiment, the status information includes at least position (location) information and shipping conditions information. Also disclosed are improved approaches for monitoring real time status information impacting inventory management of a company and/or its partners. Adverse changes in the status information of specific items can be identified in real time, and changes implemented as needed.

The invention can be implemented in numerous ways including, a method, system, device, graphical user interface, and a computer readable medium.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention will be readily understood by the following detailed description in conjunction with the accompanying drawings, wherein like reference numerals designate like structural elements, and in which:

FIG. 6 is a representative notification setup screen according to one embodiment of the invention.

DETAILED DESCRIPTION OF EMBODIMENTS OF THE INVENTION

The invention relates to improved approaches for monitoring status of articles being shipped. The monitoring can produce notifications to interested parties. The notifications typically contain status information pertaining to the articles being shipped. Alternatively, interested parties can gain access to status information pertaining to the articles being shipped via a website. According to one embodiment, the status information includes at least position (location) information and shipping conditions information.

In the following description, numerous specific details are set forth in order to provide a thorough understanding of the present invention. However, it will become obvious to those skilled in the art that the invention may be practiced without these specific details. The description and representation herein are the common meanings used by those experienced or skilled in the art to most effectively convey the substance of their work to others skilled in the art. In other instances, well-known methods, procedures, components, and circuitry have not been described in detail to avoid unnecessarily obscuring aspects of the present invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments mutually exclusive of other embodiments. Further, the order of blocks in process flowcharts or diagrams representing one or more embodiments of the invention do not inherently indicate any particular order nor imply any limitations in the invention.

Embodiments of this aspect of the invention are discussed below with reference to FIGS. 1-39. However, those skilled in the art will readily appreciate that the detailed description given herein with respect to these figures is for explanatory purposes as the invention extends beyond these limited embodiments.

Figure 1:
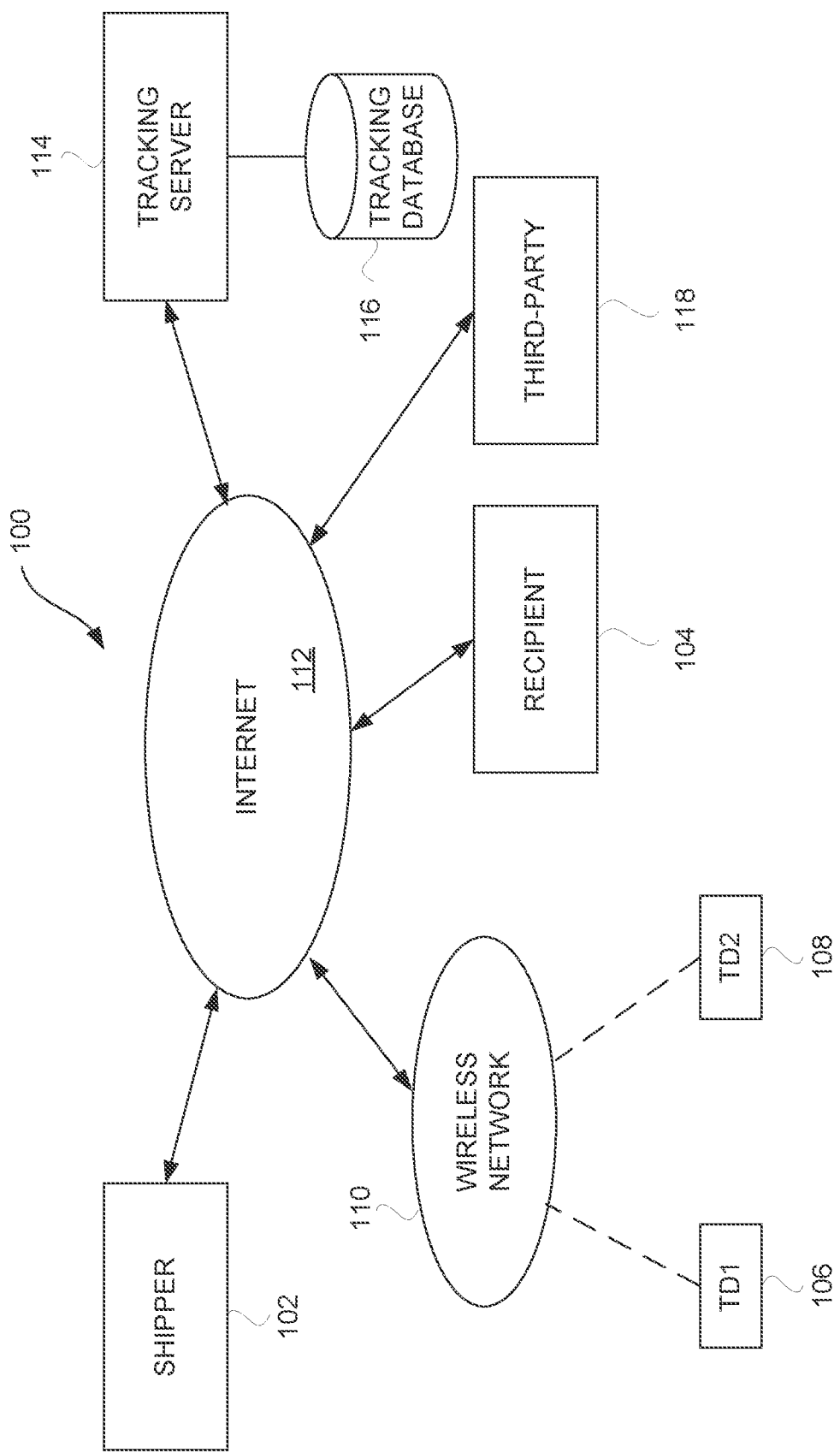
FIG. 1 is a block diagram of an article shipment notification system according to one embodiment of the invention.

FIG. 1 is a block diagram of an article shipment notification system 100 according to one embodiment of the invention. The article shipment notification system 100 provides web-based article shipment management capable of not only tracking the shipment of articles but also providing notifications to users of the system.

The article shipment notification system 100 includes a shipper 102 and a recipient 104. Typically, the article shipment notification system 100 would support multiple shippers and multiple recipients. However, in the embodiment shown in FIG. 1, only the shipper 102 and the recipient 104 are illustrated. It is assumed that an article is being shipped by the shipper 102 to the recipient 104. A shipper is a person, entity or associated computing device that is responsible for or associated with shipping an article, and a recipient is a person, entity or associated computing device to which the article is being shipped.

In order to track the location and shipping conditions of the article being shipped from the shipper 102 to the recipient 104, a tracking device (TD1) 106 is provided within or attached to the article being shipped. Additionally, a second tracking device (TD2) 108 is also illustrated in FIG. 1 which could be used to track another article. The first tracking device 106 and the second tracking device 108 are coupled to a wireless network 110. In general, the article shipment notification system 100 supports many different tracking devices. Typically, for each article being tracked, the article shipment notification system 100 would use a separate tracking device.

The wireless network 110 is coupled to the Internet 112. Further, a tracking server 114 is coupled to the Internet 112. The tracking server 114 also couples to a tracking database 116. The Internet 112 can be replaced by other data networks (e.g., enterprise network, regional network, Local Area Network, or Wide Area Network).

While an article is being shipped from the shipper 102 to the recipient 104, the first tracking device 106 gathers status information associated with the article. The status information includes at least position (location) information and/or shipping conditions information. The position information is obtained typically from a global positioning system (GPS) receiver within the first tracking device 106. The position information can be obtained or augmented by a local positioning system such as utilized with a local network (e.g., Bluetooth, Wi-Fi, etc.). The shipping conditions information pertains to conditions of or surrounding an article during its shipment. The shipping conditions information can vary with application. Examples of shipping conditions that can be provided within shipping conditions information include one or more of vibration, acceleration, speed, or direction of travel of, or force or pressure on, the article. Other examples of shipping conditions that can be provided within shipping conditions information include one or more of temperature, humidity, pressure, gaseous or liquid states, chemical compositions, wind speed, color composition, scent, light, sound, smoke, particle or radiation (e.g., infrared radiation).

The status information that is obtained by the first tracking device 106 is sent by the first tracking device 106 to the tracking server 114 via the wireless network 110 and the Internet 112. The tracking server 114 stores the status information pertaining to the first tracking device 106 into the tracking database 116 such that it is associated with the particular article being shipped. The tracking server 114 tracks the shipment of various articles, and thus stores status information pertaining to the particular articles being shipped.

As the article is being shipped, the tracking server 114 can also monitor the status information associated with the first tracking device 106 (as well as other tracking devices used with the article shipment notification system 100). The tracking server 114 can produce and send various notifications to shippers and/or recipients of articles being shipped using the article shipment notification system 100. More particularly, the tracking server 114 can monitor the status information provided by the first tracking device 106 and determine whether and when to send notifications to either the shipper 102 or the recipient 104, or both.

In one embodiment, the shipper 102 and/or the recipient 104 can provide notification criteria to the tracking server 114. The shipper 102 and the recipient 104 are coupled to the Internet 112 and thus can supply notification criteria to the tracking server 114 (as well as receive notifications from the tracking server 114). The notification criteria can specify the channel, timing and nature of the notifications to be received. The notification messages can be transmitted through different channels, such as electronic mail, text message (e.g., page, instant message, etc.), voice call, and facsimile. The timing, for example, can be periodic (e.g., daily) or on events or conditions. The nature of the notification messages can vary based on circumstances and/or user preferences. For example, the user might only desire urgent messages and not messages of lesser priorities. As another example, the user might want to receive messages in an abbreviated format as opposed to a detailed format. As still another example, the user might want to receive warning messages or messages indicating that corrective action is suggested, but opt not to receive regular status messages. In one embodiment, the notification criteria can also be considered user configuration data.

The article shipment notification system 100 can allow the shipper 102 and the recipient 104 to interact with the tracking server 114 through a web interface so that such users are able to configure or set-up to receive certain notifications. The web interface can facilitate a user in arranging to receive notifications by indicating notification criteria. For example, through use of the web interface, a user can make user selections to indicate the notifications to be received and where and by what channels the notifications are to be provided.

The article shipment notification system 100 can provide various different notifications to interested users, such as the shipper 102 and the recipient 104. For example, the shipper 102 might receive a notification that the article shipment has been delayed, a notification that the article has been delivered (arrived at the destination), a notification that shipping conditions violations have occurred, or a notification of the position of the article. For example, the recipient 104 might receive notifications such as a notification that an article has been shipped identifying the recipient as the person or entity receiving the article, a notification that an article being shipped to the recipient is nearby, and a notification that an article will be delivered to the recipient shortly (optionally including an estimated delivery time), a notification of shipping conditions violations, or a notification of the position of the article.

The article shipment notification system 100 can also include at least one third-party 118. The third-party 118 is a user interested in the shipment of the article other than the shipper 102 or the recipient 104. The article shipment notification system 100 can operate (or be configured to operate) to provide certain notifications to the third-party 118. The above-mentioned web interface can be used to configure or set-up such notifications. As examples, the third-party 118 can represent a shipping entity, an insurance company, a management organization, a financial organization, etc.

In one embodiment, the notifications can have different levels. The level of a notification can depend on security clearance, authorization, ranks within companies, or the recipient. For example, a notification directed to an insurance company might contain all available status information. In another example, a notification directed to a recipient of the article might only contain selected types/portions of status information (e.g., time of arrival but not humidity information).

The notification can be initiated by a server, such as the tracking server 104, or on-demand by a requestor (e.g., interested user).

Figure 2:
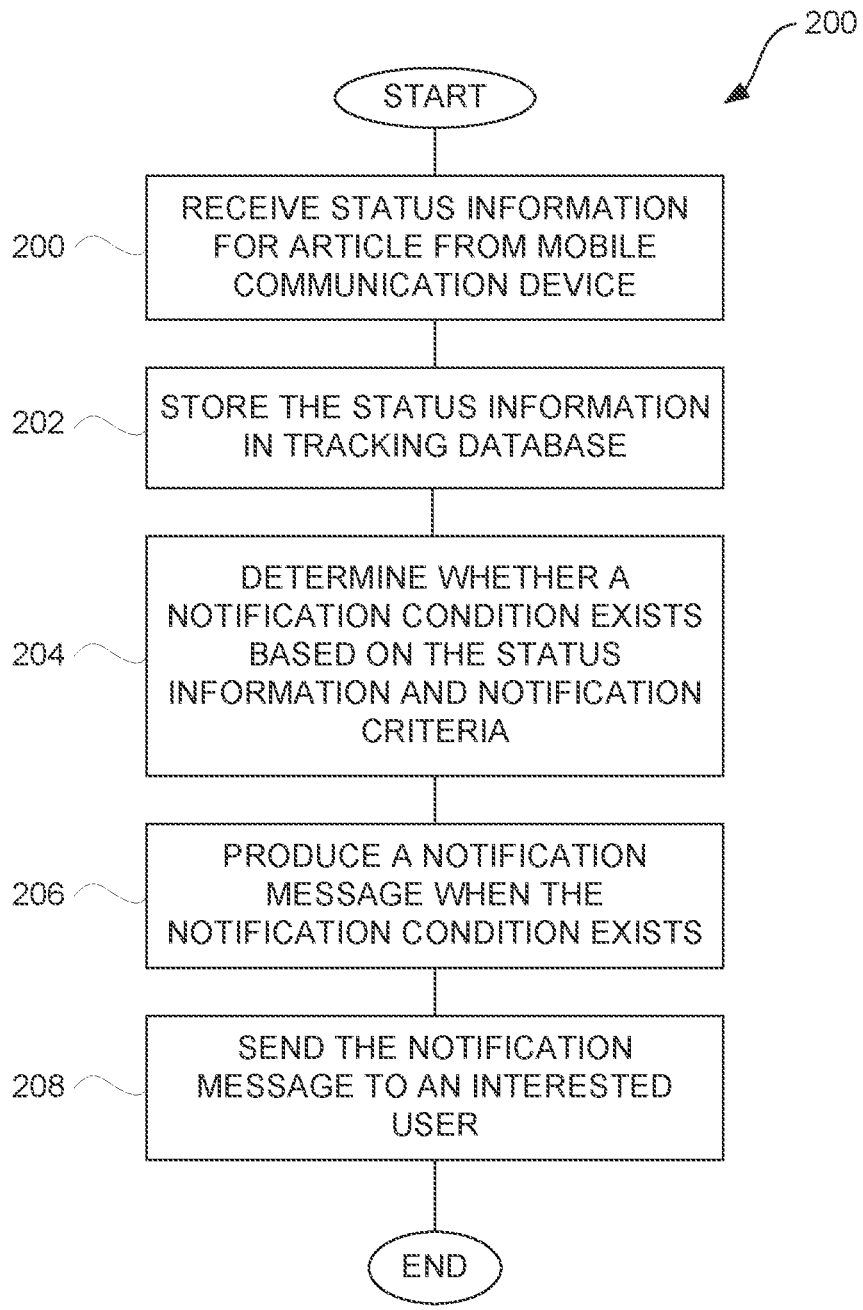
FIG. 2 is a flow diagram of article shipment notification processing according to one embodiment of the invention.

FIG. 2 is a flow diagram of article shipment notification processing 200 according to one embodiment of the invention. The article shipment notification processing 200 can, for example, be performed by a server machine, such as the tracking server 114 illustrated in FIG. 1.

The article shipment notification processing 200 receives 201 status information for an article from a mobile communication device. Here, the mobile communication device transmits the status information for the article that is associated with (e.g., coupled to or encloses) the mobile communication device. The status information that is being transmitted is received at the server by way of a wireless and/or wired network. Next, the status information is stored 202 to a tracking database. The tracking database allows the status information for the article to be organized for subsequent evaluation. The article shipment notification processing 200 then determines 204 whether a notification condition exists based on the status information and notification criteria. The status information for the article was received from the corresponding mobile communication device and stored in the tracking database as noted above. The notification criteria can be either default notification criteria or user-specified notification criteria. In any case, the status information and the notification criteria are utilized to determine whether a notification condition exists. Thereafter, a notification message is produced 206 when the notification condition exists. After the notification message is produced 206 the notification message is sent 208 to an interested user. The manner by which the notification message is sent 208 can vary depending upon the nature of the notification message, the capabilities of the communication system being used, the preferences of the interested user, and the like. After the notification message has been sent 208, the article shipment notification processing 200 is complete and ends.

Figure 3:
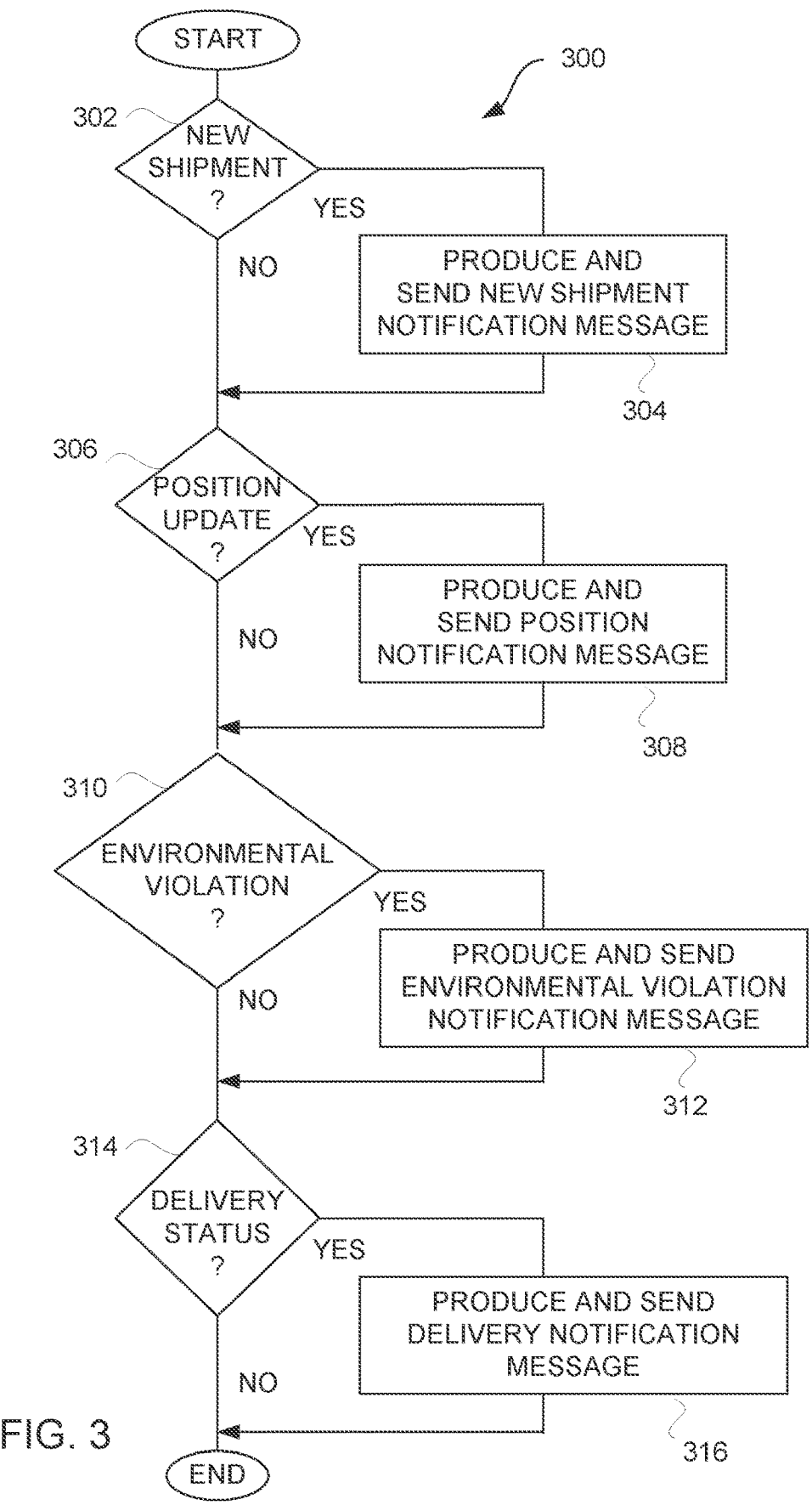
FIG. 3 is a flow diagram of notification message processing according to one embodiment of the invention.

FIG. 3 is a flow diagram of notification message processing 300 according to one embodiment of the invention. The notification message processing 300 can, for example, represent a more detailed implementation for the operations 206 and 208 illustrated in FIG. 2.

The notification message processing 300 assumes that the notification system supports the various types of notifications and distinguishes those notifications based on the existence of particular notification conditions. More specifically, the notification conditions being processed by the notification message processing 300 include, for example, notification conditions pertaining to a new shipment, a position update, an environmental violation, and a delivery status.

The notification message processing 300 begins with a decision 302 that determines whether a new shipment notification condition exists. As an example, a new shipment notification condition is a notification condition that is used to indicate that a new shipment is or has been sent. The new shipment notification condition might notify a recipient that an article was shipped to them on a particular date, from a particular person, and possible also indicate the approximate arrival date and/or time. Still further, in one embodiment, the new shipment notification message can include a link (e.g., hyperlink) to a server location wherein notifications can be arranged. When the decision 302 determines that a new shipment notification condition does exist, then a new shipment notification is produced and sent 304. Alternatively, when the decision 302 determines that a new shipment notification condition does not exist, then a decision 306 determines whether a position update notification condition exists. When the decision 306 determines that a position update notification condition exists, then a position notification message is produced and sent 308. On the other hand, when the decision 306 determines that a position update notification condition does not exist, then a decision 310 determines whether an environmental violation notification condition exists. When the decision 310 determines that an environmental violation notification condition does exist, then an environmental notification message is produced and sent 312. As an example, an environmental notification message informs the recipient of the message that one or more environmental violation notification conditions have been violated. For example, the environmental notification message might indicate that the temperature of the article has exceeded a desired limit, that the humidity has exceeded a desired limit, or that the article has undergone excessive forces. Alternatively, when the decision 310 determines that an environmental violation notification condition does not exist, then a decision 314 determines whether a delivery notification condition exists. When the decision 314 determines that a delivery notification condition does exist, then a delivery notification message is produced and sent 316. On the other hand, when the decision 314 determines that a delivery notification condition does not exist, then as well as following the operation 316, a notification message processing 300 is complete and ends.

It should be noted that the notification message processing can send one or more notifications to an interested user at any point in time. Additionally, the multiple notifications can be combined into a single notification. Further, additional notification conditions beyond those discussed with respect to the notification message processing 300 shown in FIG. 3 can also be utilized and processed in a similar manner. Still further, the organization or arrangement of the processing of the notification message processing 300 shown in FIG. 3 is illustrative and thus not required. For example, the order of evaluating the decisions is not limited to that shown in FIG. 3. In other words, the notification message processing 300 can vary with implementation.

As an illustration regarding notification, the shipping conditions information can provide chemical related feedback or notification information based on chemical substances being sensed within the package or object being shipped. For example, a chemical sensor can be provided within the mobile tracking device to sense chemical compositions (e.g., gaseous components).

With respect to the notification criteria utilized to determine when notifications are to be sent, a user can configure those notifications desired and the particular conditions for such notifications. For example, a user can configure notifications by interacting with a web site to set the notification criteria.

Although the notifications often are sent to the sender or recipient of the package or article being shipped, the notifications can also be sent or forwarded to third parties. One particular third party is, for example, an insurance representative. The notification can indicate that certain shipping conditions have been violated. The notification can also provide instructions or recommendations to take corrective action. The corrective action can, for example, include fixing the problem that caused the shipping conditions violation or mitigating damages caused by the shipping conditions violation.

Figure 4:
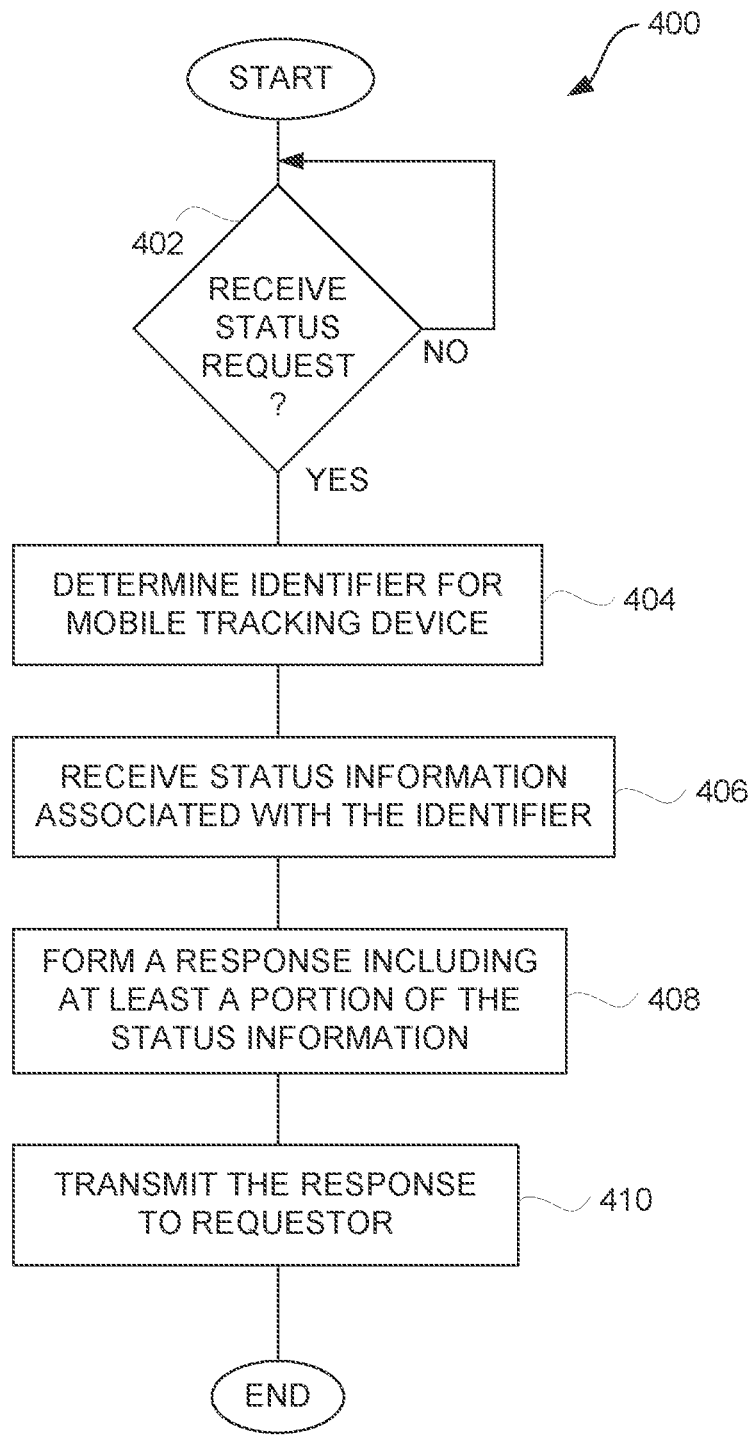
FIG. 4 is a flow diagram of requested notification processing according to one embodiment of the invention.

FIG. 4 is a flow diagram of requested notification processing 400 according to one embodiment of the invention. The requested notification processing 400 is, for example, performed by a server machine, such as the tracking server 114 illustrated in FIG. 1.

The requested notification processing 400 begins with a decision 402 that determines whether a status request has been received. When the decision 402 determines that a status request has not been received, the requested notification processing 400 awaits such a request. In other words, the requested notification processing 400 is invoked when a status request is received. A user (i.e., requestor) typically initiates the requested notification processing 400 when status information is desired by making a status request (or notification request).

Once the decision 402 determines that a status request has been received, then an identifier for the mobile tracking device is determined 404. The identifier serves to identify the particular mobile tracking device for which the status information is to be obtained. After the identifier is identified, status information for the mobile tracking device associated with the identifier is retrieved 406. If desired, the requested notification processing 400 can further determine whether the requestor for the status information is authorized to receive the status information or the level of status information the requestor is authorized to receive.

After the status information has been retrieved 406, a response including at least a portion of the status information is formed 408. In one embodiment, the response being formed 408 is in the format of an electronic mail message (email). For example, if the status request were in the form of an email message (including any text or graphical message being electronically transmitted), the response could be a reply email to the status request email message. In other embodiment, the response being formed 408 can take various other formats. After the response has been formed 408, the response is transmitted 410 to the requestor. The transmission of the response can be over a wireless and/or a wired network. For example, when the format of the response is an email message, the response is typically sent to a network address or email address associated with the requestor that issued the status request. Following the operation 410, the requested notification processing 400 is complete and ends.

Figure 5:
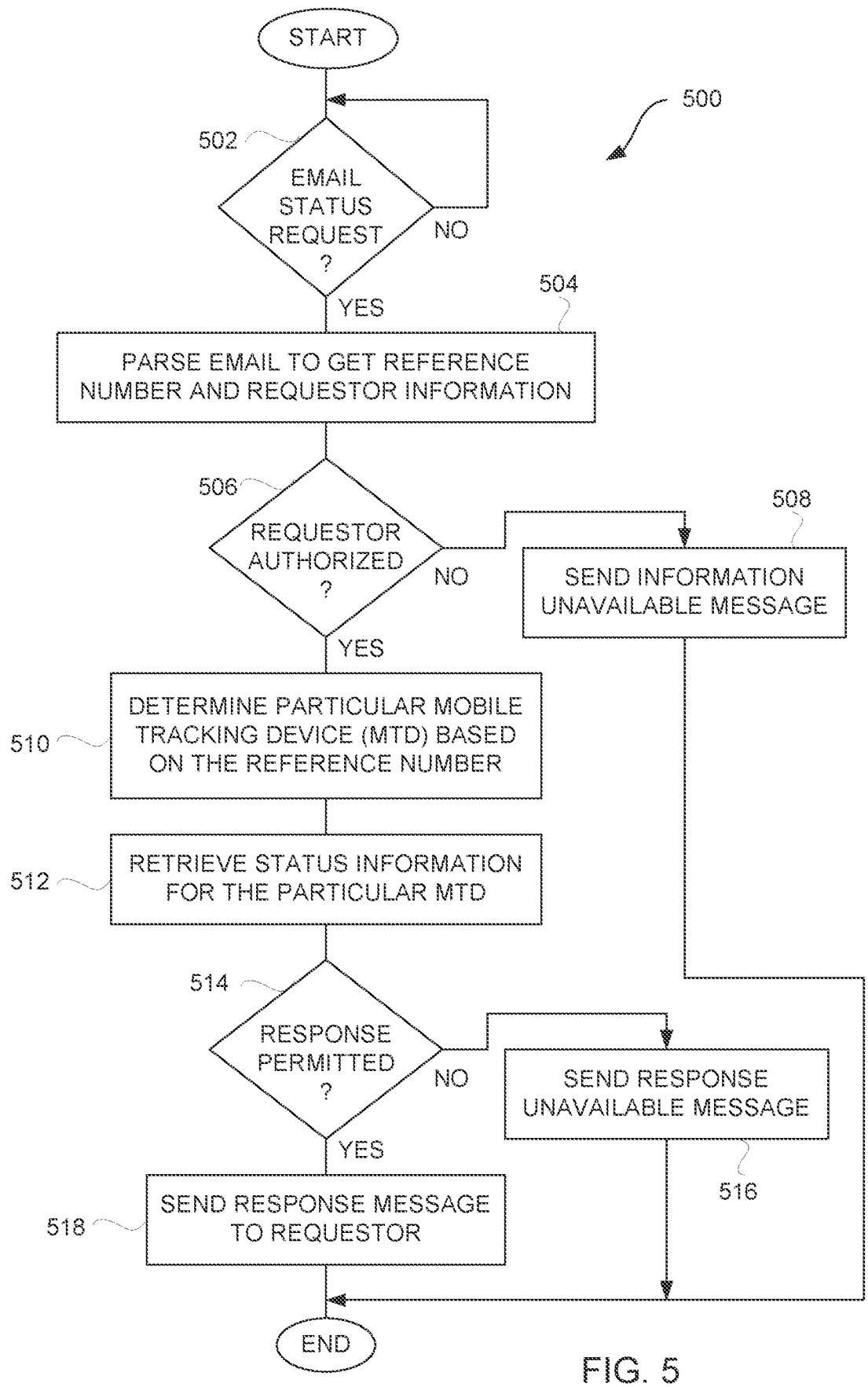
FIG. 5 is a flow diagram of email status processing according to one embodiment of the invention.

FIG. 5 is a flow diagram of email status processing 500 according to one embodiment of the invention. The email status processing 500 is, for example, performed by a server machine, such as the tracking server 114 illustrated in FIG. 1. The email status processing 500 can be considered a more detailed embodiment of the requested notification processing 400 illustrated in FIG. 4.

The email status processing 500 begins with a decision 502 that determines whether an email status request has been received 502 from a requestor. When the decision 502 determines that an email status request has not been received, then the email status processing 500 awaits such a request. Once the decision 502 determines that an email status request has been received, then the email status request is parsed 504 to get a reference number and requestor information.

Next, a decision 506 determines whether the requestor is authorized. Here, the determination of whether or not the requestor is authorized can be performed using some or all of the requestor information and the reference number for the mobile tracking device of interest. When the decision 506 determines that the requestor is not authorized, then an information unavailable reply message is sent 508 to the requestor.

When the decision 506 determines that the requestor is authorized, the mobile tracking device is determined 510 based on the reference number. As an example, the reference number can be an identifier that is used by users to identify the mobile tracking device they are desirous of tracking. Internally the system may use the reference number or another identifier. The reference number may be a fixed number or a re-assignable number that specifies a particular mobile tracking device. For example, the reference number can be a telephone number or network address used by the mobile tracking device for communications.

After the mobile tracking device has been determined 510, the status information for the determined mobile tracking device is retrieved 512. In one embodiment, the status information is retrieved 512 from a database that stores status information for a plurality of mobile tracking devices. The database is, for example, the tracking database 116 illustrated in FIG. 1.

Next, a decision 514 determines whether the requested response is permitted. In other words, although the requestor is permitted to access the status information, the type of response that is permitted to be supplied to the requestor could be limited. Hence, when the decision 514 determines that the requested response is not permitted, then a requested response unavailable message is sent 516 to the requestor. On the other hand, when the decision 514 determines that the requested response is permitted, then a response message is produced and sent 518 to the requestor. In one embodiment, the message can take different formats depending upon a user's configuration requests or the destination for the response. Following the operation 518, as well as following the operations 508 and 516, the email status processing 500 ends.

A web interface (or Graphical User Interface) can be made available to users. The web interface can, among other things, assist a user with configuring notifications for themselves or others. One embodiment of such a web interface is referred to as a notification setup screen.

FIG. 6 is a representative notification setup screen 600 according to one embodiment of the invention. The notification setup screen 600 is, for example, displayed on a display device associated with a user's computer. The notification setup screen 600 would be presented on the display device of the user's computer when the user desires to configure the notification system to provide certain automated notifications. As an example, a network browser application operating on the user's computer can present the notification setup screen 600 and interface thereby with the tracking server 114 to configure the notification system. The user can, for example, be the shipper 102, the recipient 104 or the third-party 118 illustrated in FIG. 1.

The notification setup screen 600 includes a notification format region 602, a notification destination region 604, and a notification criteria region 606. These regions are portions of the notification setup screen which is often a window displayed on a display device as a graphical user interface. The notification format region 602 is a region that allows the user to select a notification channel (format). In the example, shown in FIG. 6, the user is able to select one of email, page or facsimile as the notification channel. The notification destination region 604 is a region that allows the user to specify one or more destinations. The destination can be an email address, a network address, a telephone number, or a facsimile number. The notification criteria region 606 is a region that allows the user to select, enter or otherwise choose notification criteria. The notification criteria set when and/or what notification are sent to the recipient users. The notification criteria can, for example, enable a user to specify that notifications are to be sent based on position, delivery or other conditions. For example, the notifications regarding position can be configured to be sent periodically (e.g., hourly, daily, weekly, etc.) or based on a distance traversed (e.g., every 1, 5, 10, 50 or 100 miles). For example, the notifications regarding delivery can be configured to be sent on delivery of the article/object to a destination, or when delivery is impending (i.e., article/object is proximate to the destination). For example, the notification regarding conditions of the shipment can be initiated periodically or on-event. In the representative example shown in FIG. 6, the notification can be periodic (e.g., hourly, daily, weekly, etc.) or can be when an extreme condition occurs, such as temperature exceeding a threshold temperature or a force exceeding a threshold amount.

Regardless of how the notification is triggered, the content of the notification could include merely status information about the condition causing the trigger, or could also include other current status information. For example, a periodic position notification could also include other status information besides position information. Likewise, a periodic condition notification could include other condition information (e.g., temperature, force, etc.) as well as position information.

Further, different channels, types or criteria can be used to provide notifications to different recipients. Hence, the notification can be customized for different users, namely, shippers, recipients and third-parties.

The web interface used to configure notification is not limited to the notification setup screen 600 illustrated in FIG. 6. Instead, the web interface can take a variety of different forms. It may use defaults, preferences (e.g., user-specified or inferred from prior actions), or other means to assist the user in interfacing with the web interface.

The notifications provided by the invention can be informative and/or instructive. The informative nature of the notifications reflects the inclusion of status information in the notification. The instructive nature of the notifications can reflect instructions or requests for corrective action to remedy dangerous or unwanted status of the shipment. For example, if a shipment is reaching dangerously high temperatures, the shipping company can be notified of the present or anticipated problem and request corrective action to remedy the situation. Further, the status information history for the shipment of the article can be made available so an interested user can evaluate where a problem occurred, how it occurred, and who was at fault.

When shipping an article, a shipper might insure the shipment. The insurance could, for example, be provided by the shipping entity or a third party. The insurance could insure against certain insured criteria, such as delivery by a deadline, damage to the article, exposure of the article to an unaccepted environmental conditions, etc. Notifications concerning violations (or non-violations) of insured criteria can be automatically provided to interested users.

Figure 7:
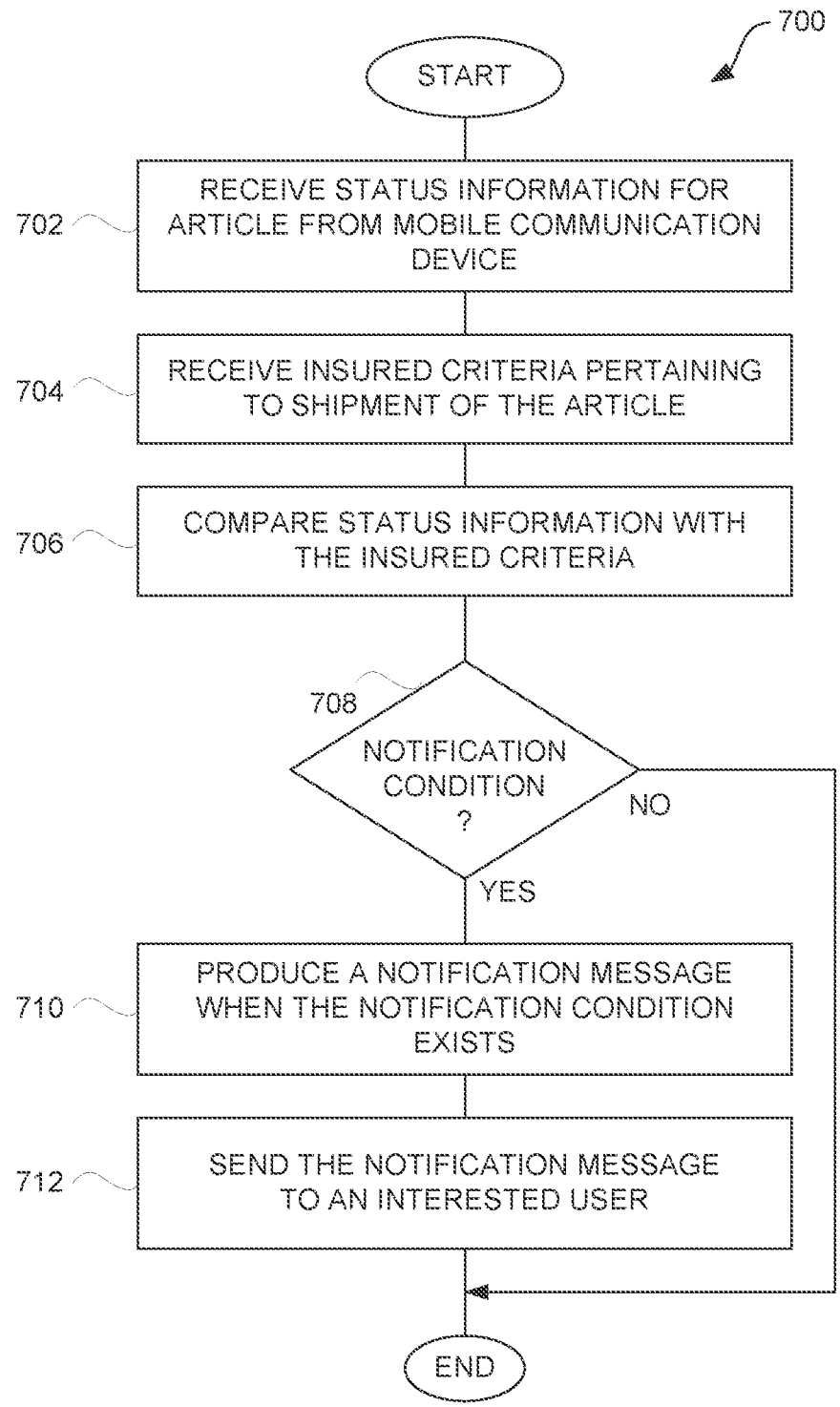
FIG. 7 is a flow diagram of insurance compliance processing according to one embodiment of the invention.

FIG. 7 is a flow diagram of insurance compliance processing 700 according to one embodiment of the invention. The insurance compliance processing 700 can, for example, allow notification messages to be automatically sent to interested users (e.g., shipping entity, shipper, or insurance representative).

The insurance compliance processing 700 receives 702 status information for an article from a mobile communication device. As noted above, at least in one embodiment, the status information includes at least position (location) information and shipping conditions information. In addition, insured criteria pertaining to the shipment of the article is received 704. The insured criteria are typically dependent on insurance policy coverage placed on the article. Next, the status information is compared 706 with the insured criteria. A decision 708 then determines whether a notification condition exists. In one implementation, a notification condition exists when the status information indicates that one or more insured criteria have been breached. In another implementation, an interested user can configure the system to set notification conditions associated with status conditions and insured criteria. When the decision 708 determines that a notification condition exists, then a notification message is produced 710. The notification message is then sent 712 to an interested user. After the notification message is sent 712, the insurance compliance processing 700 is complete and ends. Alternatively, when the decision 708 determines that a notification condition does not exist, then the operations 710 and 712 are bypassed and the insurance compliance processing 700 ends.

In the course of shipping an article, a shipping entity might have agreed to deliver the article to a destination within a prescribed period of time. The failure of the shipping entity to meet this or any other condition can entitle the sender or recipient to a refund of some of all of the costs the sender incurred in shipping the article. Typically, the party that originally paid for the costs of the shipping would normally be the party that receives the refund. The discussion provided below primarily assumes that the sender is the party that would receive any refund, though such is not a limitation.

Figure 8:
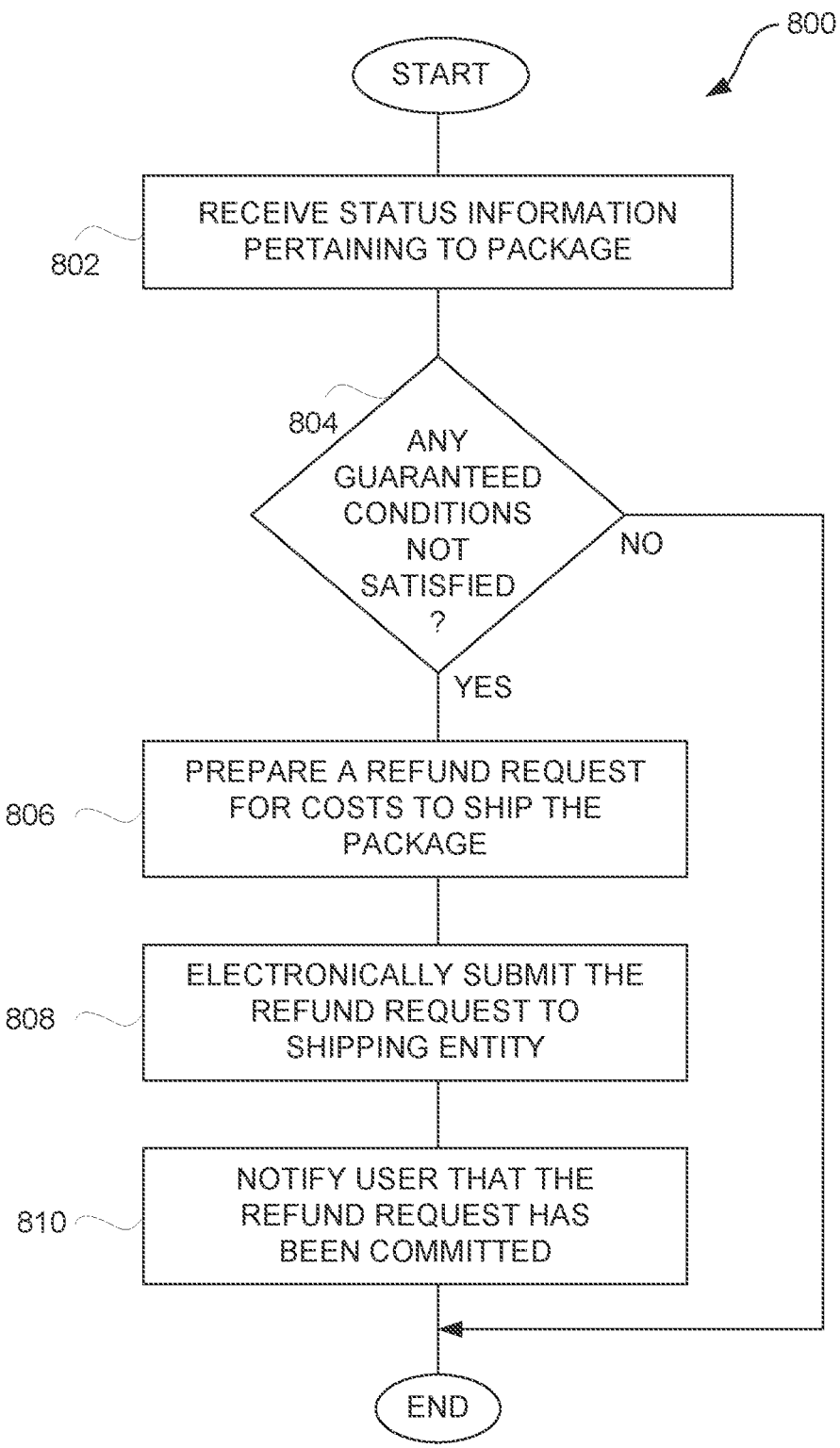
FIG. 8 is a flow diagram of refund processing according to one embodiment of the invention.

FIG. 8 is a flow diagram of refund processing 800 according to one embodiment of the invention. The refund processing 800 serves to automatically request and process refunds on behalf of senders, and their refunds with respect to shipping entities.

The refund processing 800 begins by receiving 802 status information pertaining to a package (i.e., article). The package is being shipped to a recipient. The sender is utilizing a carrier (i.e., shipping entity) to perform the shipping function to deliver the package to the recipient. A decision 804 determines whether there are any guaranteed conditions associated with the shipment that have not been satisfied. Here, the status information can be utilized to determine whether one or more of the guaranteed conditions are not satisfied. The guaranteed conditions are typically associated with a shipping agreement between the sender and the shipping entity. In one embodiment, one guaranteed condition of a shipment is a guaranteed delivery time. When the decision 804 determines that one or more guaranteed conditions of the shipment have not been satisfied, then a refund request is prepared 806 to recover some or all of the cost to ship the package. Next, the refund request is electronically submitted 808 to the shipping entity. The submission to the shipping entity can be done using a general address, a special address associated with refunds, or it could be an agent's address that is utilized to process the refund request for the shipping entity. Further, the electronic submission 808 can be performed through electronic mail, facsimile transmission, or FTP transmission. After the refund request has been electronically submitted 808, the user (sender) is notified 810 that the refund request has been submitted. On the other hand, when the decision 804 determines that all guaranteed conditions have (so far) been satisfied, then the operations 806-810 are bypassed. Following the operation 810, the refund processing 800 is complete and ends.

Additionally, the refund processing could also further monitor the processing of a refund request by the shipping entity. For example, after submission of the refund request, the refund processing can examine whether the refund associated with the refund request has been received. Further, additional monitoring could be performed to determine that the receipt of the refund request has been received, the stage of its processing by the shipping entity, or other refund related information. Furthermore, the user (sender) can be notified when the refund monies have been received. These refund monies can be electronically transmitted to the sender or can be placed in an account that is associated with the sender.

The refund processing can be initiated in a variety of different ways. For example, the refund processing can be triggered by the arrival of the package at its destination. Alternatively, the refund processing could be performed whenever a guaranteed condition is not met, such as the guaranteed delivery time has been exceeded. As yet another alternative, the refund processing can be performed as status information is updated or as processing resources are available.

The invention is suitable for asset management, such as tracking location/position of assets and monitoring conditions of assets. Assets can, for example, include: packages, purchased goods, moving boxes/creates, and pallets.

The position resolution can be enhanced through use of a community layout and/or profile information.

Figure 9:
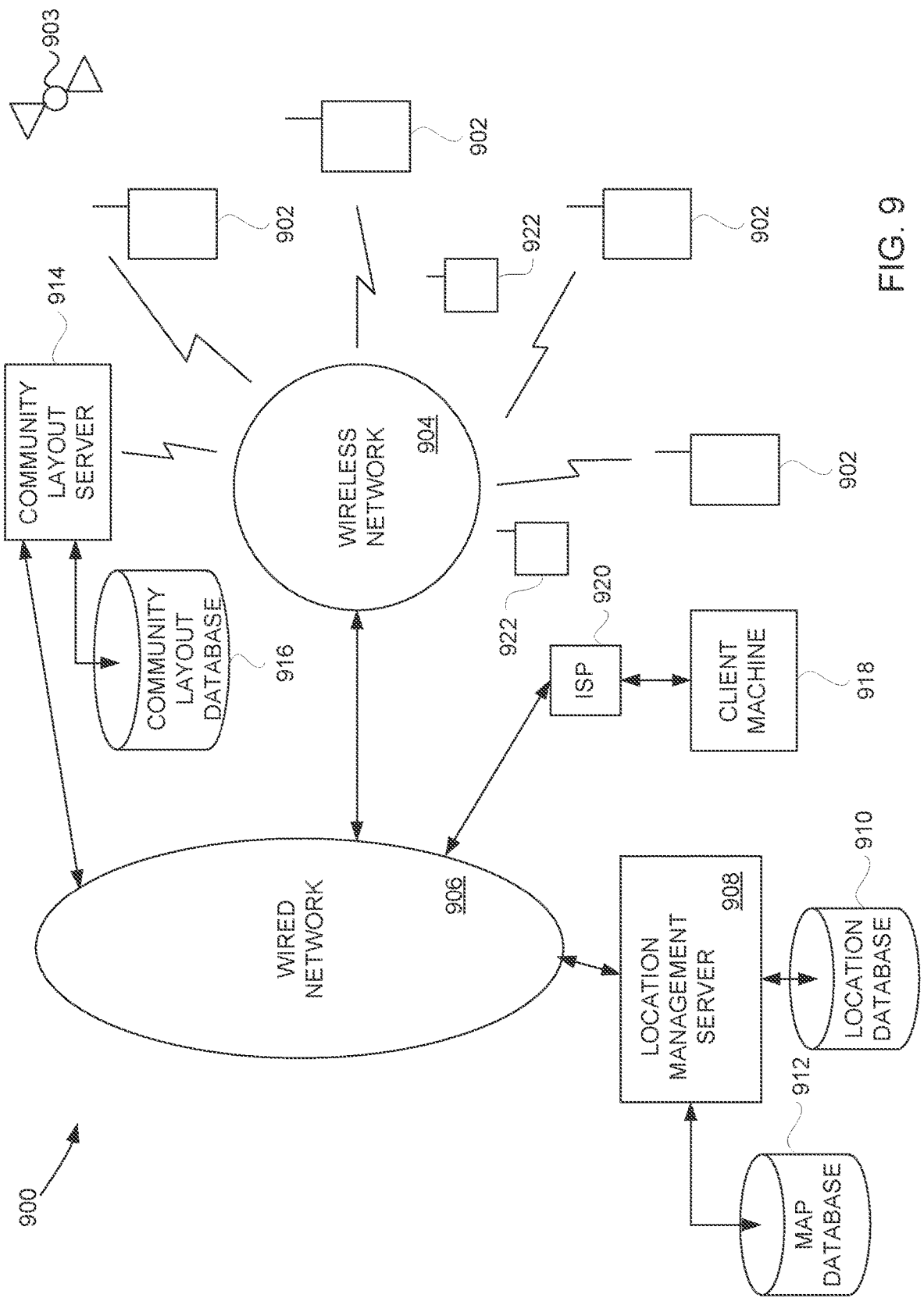
FIG. 9 is a block diagram of an object tracking system according to one embodiment of the invention.

FIG. 9 is a block diagram of an object tracking system 900 according to one embodiment of the invention. The object tracking system 900 can be used to track various objects including packages, humans, pets and the like. The object tracking system 900 includes a plurality of wireless devices 902. These wireless devices 902 are provided with or proximate to objects being tracked by the object tracking system 900. These mobile devices 902 have GPS receivers that can receive GPS position information from a GPS system 903. The acquisition of such position information can be performed on demand, periodically or on need. The mobile devices 902 communicate over wireless links with a wireless network 904. The wireless network 904 then couples to a wired network 906. A location management server 908 is coupled to the wireless network 906. The location management server 908 provides centralized storage of the location information for each of the mobile devices 902 in a location database 910. A map database 912 is also coupled to the location management server 908. The map database 912 can directly connect to the location management server 908 or can reside elsewhere on the wired network 906. The location management server 908 can interact with the map database 912 to convert position information provided by the GPS information into map coordinates, street addresses, etc.

In addition, the object tracking system 900 also includes a community layout server 914. The community layout server 914 can be coupled to the wired network 906 or the wireless network 904. In one embodiment, a community can be associated with a commercial building, a shopping mall, a residential community and the like. The community layout server 914 interacts with a community layout database 916 to resolve locations, such as street addresses and cross streets, into more intelligible locations in a community. For example, instead of a street address, the locations can pertain to points of interest with respect to the community. As an illustration, in the case of a commercial building, with five floors, the community layout database 916 would convert the GPS information (plus any additional sensor information relevant to making the determination also provided by the mobile device 902, such as altitude and direction) to obtain a community location or point of interest. For example, using the GPS position information together with other sensor information, the community layout server 914 can interact with the community layout database 916 to precisely locate a particular mobile device 902 to a particular point of interest. In the case of the commercial building with five floors, the mobile device 902 can be pinpointed to the third floor which pertains to the corporation Acme, Inc. The point of interest or community position can then be sent from the community layout server 914 through the wired network 906 to the location management server 908 which then in turn stores the community position or point of interest in the location database 910 as the position of the particular mobile device 902.

Once the location database 910 has the positions of the mobile devices 902, when subsequent position data is sent to the location management server 908, these positions are suitably updated in the location database 910. Additionally, other of the mobile devices 902 or a representative client machine 918 coupled through an Internet Service Provider (ISP) 920 to the wired network 906 can be permitted to access the locations of one or more of the mobile devices 902. Assuming that the requesting party is allowed access to said position information, the request for such information is processed by the location management server 908. When permission is granted, the locations desired are retrieved from the location database 910 and returned to either the requesting mobile devices 902 or the requesting client machine 918. In a similar manner, access to other non-location information (i.e., additional sensor information or conditions information) pertaining to the mobile devices 902 can be available.

In one embodiment, the client machine 918 or a particular one of the mobile devices 902 can set up a private or semi-private web page that is hosted by a server (e.g., the location management server 908 or other server) on the wired network 906. Then, the page can be customized to monitor the location of a number of the mobile devices 902. Hence, thereafter, the requestor need only access the customized web page to obtain the current position information for such mobile devices. With such an embodiment, a web page could be provided to track a plurality of packages being transported from a warehouse to a customer. In another embodiment, a similar web page can be setup to allow a parent to track the position of mobile devices that are affixed to his children such that the parent can easily monitor the position of his children. In this example, the object tracked is a living being (e.g., person).

The object tracking system 900 could also be augmented by wireless profile devices 922. These profile devices 922 can wirelessly couple to the mobile devices 902 using the wireless network 904. The profile devices 922 could be short range transmitters or transceivers. The profile devices 922 could store one or more profiles for a particular location in which they reside.

Hence, the mobile device 902 can wirelessly communicate with the profile device 922, if available, to acquire a profile pertaining to its location. For example, with the profile device 922 placed in the office building of Acme, Inc., when the mobile device 902 is in such office building, the mobile device 902 can acquire the profile from the proximate profile device 922. The profile can include the business name, its location, contact information for the business, etc. Thereafter, some or all of the profile information can be stored in the mobile device 902 and/or forwarded to the location management server 908 or other server for storage. Hence, the location provided by the profile may be more exacting and descriptive than the GPS position, such that the location of the mobile device 902 can be better determined.

In some cases it may be useful to control or limit the wireless communications with respect to the profile devices 922 so that the mobile devices 902 do not inadvertently receive the wrong profile. Various techniques can be utilized to provide control over the wireless communications. For example, the profile device 922 may or may not use a directional antenna. As another example, the profile device 922 could also control (e.g., limit) its transmission power.

In one embodiment of package tracking and monitoring, a GPS-enabled mobile device is attached to a package. As the package travels, the mobile device periodically sends its position information wirelessly to a center. This can be done, for example, through a cellular connection. The center keeps track of the package's location, and can post its path on a Web site. A user might have to pay to access the location information. For example, at 3 am in the morning, the user can log into the site, and enter a password to find out that the package is on the 9th floor of the Empire State Building (e.g., it destination), or more particularly the package is at the office of Acme, Inc. on the 9th floor of the Empire State Building.

In one embodiment, in addition to position information, other identifying information can also be automatically included based on radio frequency identification (RFID) tags. The RFID tags typically include memory chips equipped and radio antennas. They can be attached to objects (or people) to transmit data about the objects. Typically, the memory chips do not include tremendous amount of information. They may only have 2 kilobytes of data, sufficient to encode, such as a serial number, where and when the product was manufactured, and other relevant information. These tags can come in a number of configurations. For example, an active tag uses a battery-powered transponder to emit a constant signal carrying the identifying information programmed into the chip. Active tags are more applicable to situations where readers are not close to the tags. A semi-passive tag likewise has a battery, but may not be activated until it receives a signal from a reader. They are more applicable to situations that do not need continuous tracking. A passive tag has no battery; its antenna extracts power from the reader's radio wave signal to transmit the identifying information on the chip. Passive tags are typically relatively inexpensive, but may have to be within a few feet of a reader to extract power. The tags can provide identifying information to the corresponding positioning information, which may also include temporal information. Together, the location and identification of assets can be automatically tracked.

In still another embodiment, personalized asset management or object tracking can be provided. For example, a user can track a package or object being shipped at her convenience. Such tracking can be achieved independent of a shipping entity that ships the package. A representative scenario is as follows. A user acquires a location-aware (e.g., GPS-aware) mobile communication device, such as a limited-functionality mobile telephone or 2-way pager, and places the mobile communication device in or on the package or object. The user makes note of the identifier for the mobile communication device. Then, periodically or on-demand, the user can determine the precise location of her package. In one implementation, the user (or a server on the user's behalf) sends a message to the mobile communication object. The message can be a voice or text message, or other form of data, that simply requests the mobile communication device to get its present location. The mobile communication device then determines its location. The mobile communication device can determine its location, for example, by directly using a GPS receiver or indirectly via another device in its immediate vicinity having GPS awareness. Further, battery lifetime can be conserved using the intelligent GPS information acquisition approaches noted in U.S. Provisional Patent Application No. 60/375,998. The mobile communication device then replies back (e.g., through voice or text message) to the user (or server) to inform of its present location. The user can, for example, call or page the mobile communication device and get the reply message. Alternatively, the user need only access the server to access the location data it holds for the package or object associated with the mobile communication device. The server can also automatically track these mobile communication device and alert the users when problems or delays in its transport are identified. Further, alerts or message could notify a recipient or sender of an object or package when the same is determined to be in-route, arrived at and/or proximate to its destination. Besides location, the reply message could also provide other information such as velocity, temperature, humidity, pressure, forces or stresses.

In one embodiment, the mobile device (mobile tracking device or mobile communication device) can include a solar panel. The solar panel can provide electrical power for the mobile device. The solar panel can thus charge a battery used to power the mobile device and/or itself power the mobile device. When the mobile device is affixed to an object (e.g., package) to be shipped, the solar panel can remain at least partially exposed to the outside of the object so as to be able to receive light. The solar panel can be integrated with the housing of the mobile device or can be separate and couple to the mobile device via one or more wires (e.g., a cable).

The present invention has described one or more GPS devices as to identify a location. However, the present invention is not limited to using GPS devices. In certain situations, other wireless or mobile devices can also serve as location-designating devices, such as devices based on GSM technologies or Wi-Fi technologies. Through the techniques of triangulation, these devices can also designate a location. Such triangulation techniques should be known to those skilled in the art.

One embodiment of the invention relates to an inexpensive position-sensing device that allows widespread use and availability of position information. The availability of position information in an inexpensive manner is highly desirable. However, there are a number of factors preventing such availability, such as cost and, sometimes, the size of the sensors. One approach of the invention provides an inexpensive position-sensing device that can be attached to or located on an object. In another embodiment, the position-sensing device is in a convenient form factor applicable for transport. Based on a number of embodiments of the present invention, position information can become not only a sought-after feature, but also a common commodity.

One embodiment of the invention includes a position-sensing device, which can be based on GPS technology. After acquiring position signals, the device extracts raw position data from the signals. Then, the device wirelessly transmits the raw position data to a position-computing device. The position-computing device can be used to convert the raw position data received into the position of the position-sensing device. The position-computing device can also receive auxiliary information from auxiliary sensors. Further analysis can then be performed based on the position and the auxiliary information. Examples of auxiliary sensors are pressure sensor, smoke detectors and heat sensors. The auxiliary sensors can capture their corresponding auxiliary information and provide them to the position-computing device.

The position-computing device can re-transmit the position of the position-sensing device with the auxiliary information to a remote site for additional analysis. The remote site can include a website. The remote site can provide additional intelligence and send different types of information back to the position-computing device. For example, location, map or traffic information can be downloaded to the position-computing device.

The position-computing device can also control an actuator. Based on an analysis performed by the remote site, the position-computing device can send a signal to an actuator to perform an operation. The operation can simply be displaying a message, flashing a signal or turning on a heater.

In one embodiment, the position-sensing device does not include a keyboard or display. This facilitates the position-sensing device in being compact in size and inexpensive. In addition, in another embodiment, a number of components of the position-sensing device's circuitry can be integrated together. For example, the components can be incorporated on two semiconductor chips, one substantially for radio-frequency circuits and the other for low-frequency baseband processing circuits. With the advantageous size and cost benefits, the position-sensing devices can be conveniently included into packages for shipment to track the packages, or can be attached to a person for monitoring purposes.

In one approach, an auxiliary sensor can be integrated into the position-sensing device, and the fabrication process can include micromachining techniques.

Figure 10:
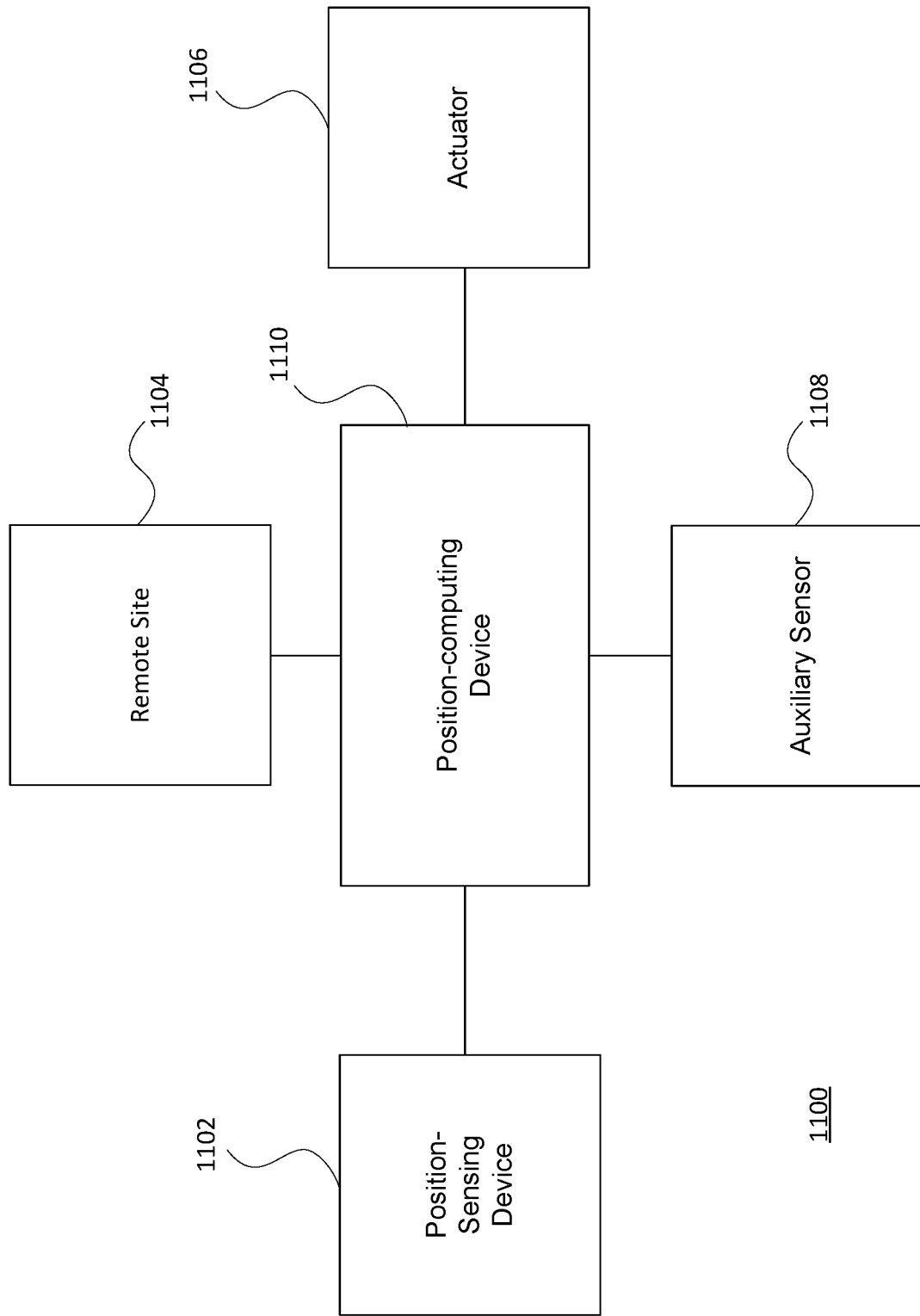
FIG. 10 shows one embodiment of the present invention.

FIG. 10 shows a position-sensing device 1102 according to one embodiment of the invention. The position-sensing device 1102 can be coupled to a position-computing device 1110, which, in turn, can be coupled to an auxiliary sensor 1108, a remote site 1104, and an actuator 1106. The position-sensing device 1102 can be based on global positioning system (GPS) technology, and can be compact and inexpensive. In one implementation, in a general sense, the position-sensing device 1102 only has to track the GPS satellites and send raw position data to the position-computing device 1110 where position computation can be performed. The position-sensing device 1102 can be very portable. For example, one can easily affix the position-sensing device 1102 to a person, package or other object. As another example, the position-sensing device 1102 can be temporarily placed within a vehicle and easily carried from one vehicle to another.

In one approach, the position-computing device 1110 receives and converts the raw position data from the position-sensing device 1102 into the position of the position-sensing device. In another approach, the position-computing device 1110 can receive the raw position data from the position-sensing device 1102 and then forward the raw position data (or a partially processed version thereof) to a remote computing device (e.g., remote server) for additional processing.

In one embodiment, a position sensor as used herein refers to a system, apparatus or device that includes not only a position-sensing device but also a position-computing device. For example, with respect to FIG. 10, the position-sensing device 1102 and the position-computing device 1110 can together be referred to as a position sensor.

Figure 11:
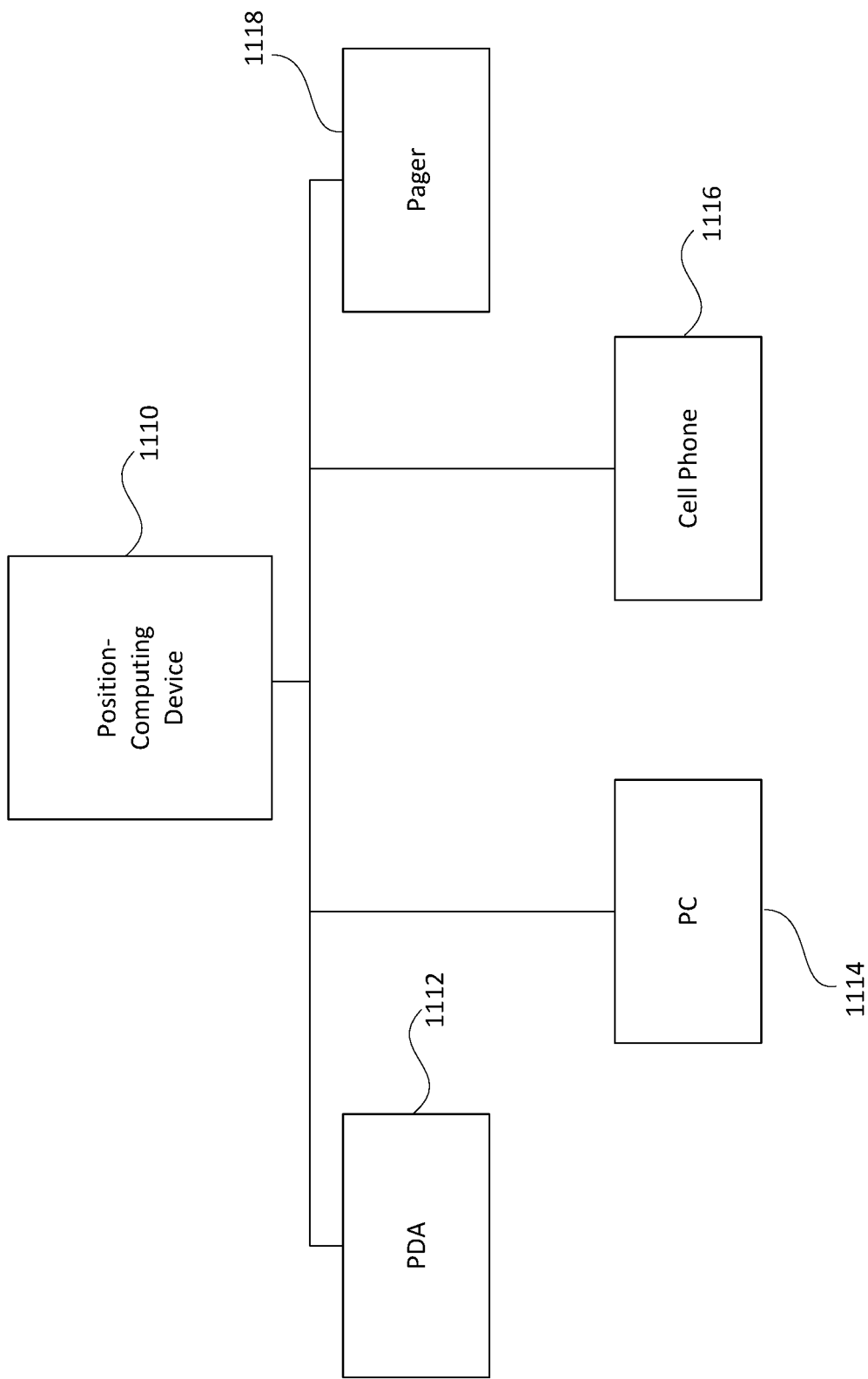
FIG. 11 shows a number of embodiments for the position-computing device of the present invention.

FIG. 11 shows a number of embodiments for the position-computing device 1110. The position-computing device 1110 can be a personal digital assistant (PDA) 1112, a personal computer (PC) 1114, a cell phone 1116, a pager 1118, or other types of electronic device typically with computation and signal transceiving capabilities.

In one embodiment, the position-sensing device 1102 does not have any user input/output interface other than a link (e.g., wireless link) to the position-computing device 1110. With such an embodiment, the position-sensing device 1102 can be made particularly small and low cost. The position-computing device 1110, which can be a portable device, can provide user-interface functionality. For example, the position-computing device 1110 can include a keyboard, a touch-pad or a stylus for information entry. The output of the position-computing device 1110 can be text, audio or graphical. When the position-computing device 1110 has a display screen, then text or graphics can be displayed on the display screen. As an example of a graphics output, the position-computing device 1110 can display a moving map on the display screen. In the case of an audio output, the position-computing device 1110 can, for example, output voice instructions pertaining to positions. In one embodiment, the computation capabilities of the position-computing device 1110 are also applicable for other applications. For example, when the position-computing device 1110 is implemented by a PDA 1112, the PDA 1112 can operate to perform processing for calendars, appointments, address books, phone books, or other application provided by the PDA 1112.

Figure 12:
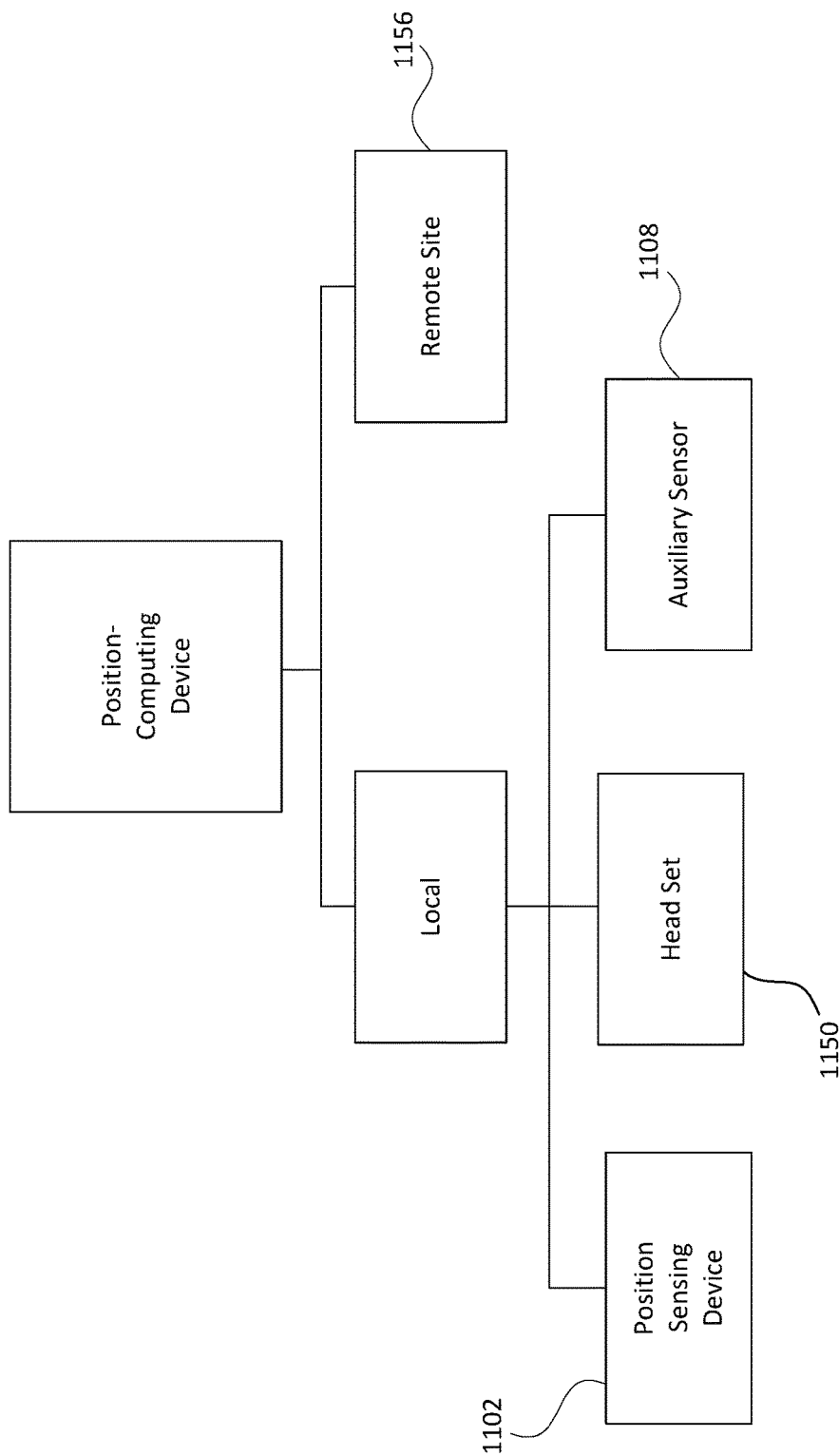
FIG. 12 shows examples of connections made by the position-computing device of the present invention.

FIG. 12 shows examples of connections that can be made by the position-computing device 1110. Locally, the position-computing device 1110 can be coupled to a position-sensing device 1102. In one embodiment, the communication between the position-sensing device 1102 and the position-computing device 1110 can, for example, be via a Bluetooth network or a wireless LAN (e.g., Wi-Fi, 802.11a or 802.11b). In such an embodiment, the position-computing device 1110 can be placed anywhere within the signal reception range of the wireless link from the position-sensing device 1102. For instance, the position-computing device 1110 can be placed in the shirt pocket of a driver, and the position-sensing device can be on the dashboard of the car. In any case, since the position-computing device 1110 and the position-sensing device 1102 do not have to be physically tied together via a cable, a user enjoys greater freedom in the placement of the position-sensing device 1102 and the position-computing device 1110. In yet another embodiment, the communication between the position-sensing device 1102 and the position-computing device 1110 can be through a serial connection (e.g., USB or FIREWIRE link).

The position-computing device 1110 can also be wirelessly coupled to a head set 1150 having a speaker and a microphone. Again, as an example, the wireless coupling between the position-computing device 1110 and the heat set 1150 can be via the Bluetooth or Wi-Fi protocols.

In one embodiment, a user wearing the headset 1150 can receive voice instructions via the wireless link between the position-computing device 1110 and the headset 1150. In addition to receiving the voice instructions (e.g., voice directions), the user can also issue voice commands to the position-computing device 1110 via the microphone of the head set 1150. Alternatively, the headset 1150 can couple to the position-computing device 1110 via a wired link (e.g., cable).

Figure 13:
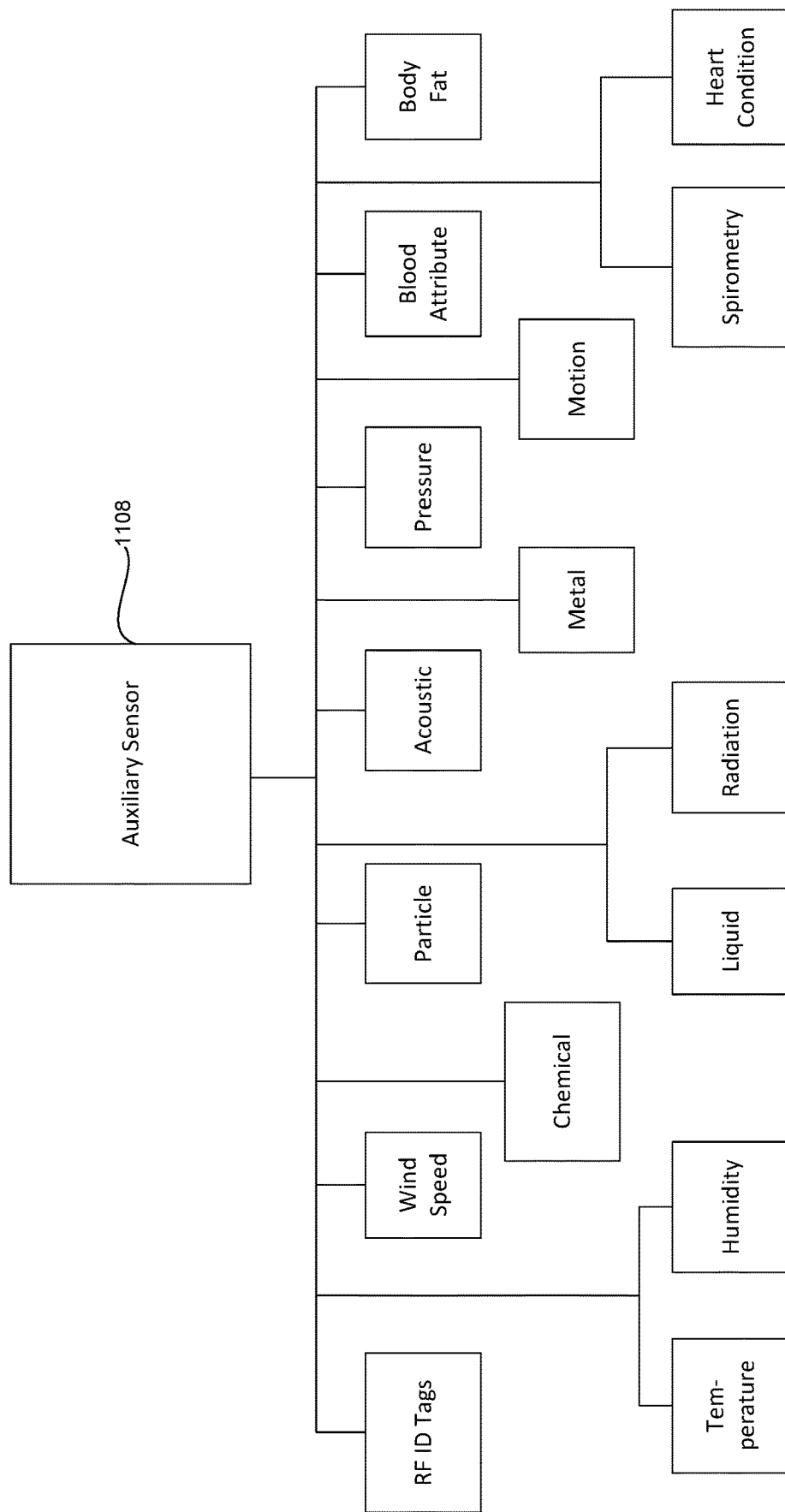
FIG. 13 shows examples of auxiliary sensors of the present invention.

The position-computing device 1110 can be locally coupled to one or more of the auxiliary sensors 1108. FIG. 13 shows examples of auxiliary sensors 1108. The auxiliary sensors 1108 capture or acquire auxiliary information, and then can wirelessly transmit such information to the position-computing device 1110. In one embodiment, an auxiliary sensor is not a position-sensing device.

The auxiliary sensor 1108 can be an environment sensor, capturing information regarding the environment where the position-sensing device 1102 is located. For example, the auxiliary sensor 1108 can be a sensor for temperature, humidity, wind speed, chemicals, particle, liquid, radiation, sound/acoustic, metal or pressure. When the auxiliary sensor 1108 is a chemical sensor, the sensor can, for example, sense oxygen level or carbon monoxide level. Similar to a chemical sensor, the auxiliary sensor 1108 can be an odor sensor. When the auxiliary sensor 1108 is a particle sensor, the sensor can, for example, be a smoke detector. When the auxiliary sensor 1108 is a radiation detector, the sensor can, for example, be a light sensor or an infrared detector. When the auxiliary sensor 1108 is a pressure sensor, the sensor can, for example, sense atmospheric pressure or device (e.g., tire) pressure.

The auxiliary sensor 1108 can also capture information pertaining to the position-sensing device 1102. In other words, the auxiliary sensor 1108 can sense information pertaining to the position-sensing device 1102 itself, such as its motion or pressure asserted on it. The information related to the motion of the position-sensing device 1102 can be its speed, direction of travel, acceleration, shock, or vibration. Regarding pressure, the auxiliary sensor 1108 can sense the force or pressure asserted on the position-sensing device 1102.

In one embodiment, the auxiliary sensor 1108 can be part of the position-sensing device 1102 and sense information regarding a living being (e.g., a person). The position-sensing device 1102 may be attached to the being or be in close proximity to the being. The information sensed by the auxiliary sensor 1108 can include the being's vital parameters. For example, the auxiliary sensor 1108 can measure the being's body temperature, blood attributes, spirometry, heart conditions, brain wave, sound/acoustic waves, or body fat. The blood attributes can include blood pressure, blood sugar or glucose level, or blood oxygen. Heart conditions can include ECG, heart rate, or arrhythmias. Sound/acoustic waves can be those measurable by a stethoscope or an ultrasound scanner. The auxiliary sensors 1108 can be non-invasive or invasive. The auxiliary sensors 1108 can be in vitro or in vivo.

Still further, the auxiliary sensors 1108 can also pertain to sensors for color, pattern, or touch (tactile).

In one embodiment, the position-computing device 1110 can be coupled to a remote site 1156, and can transmit the position-sensing device's position and/or auxiliary information to the remote site 1156 for additional analysis. The coupling can be through a local area network, or a wide area or global network. The wide area or global network can be a SMS network. The remote site 1156 can interface with users through a website. The additional analysis performed by the remote site 1156 can include a number of operations, such as labeling the positions of the position-sensing device 1102, enhancing the accuracy of the labels and/or positions, or compressing the position and/or auxiliary information received, as, for example, described in U.S. Provisional Patent Application No. 60/404,645, filed Aug. 19, 2002.

Figure 14:
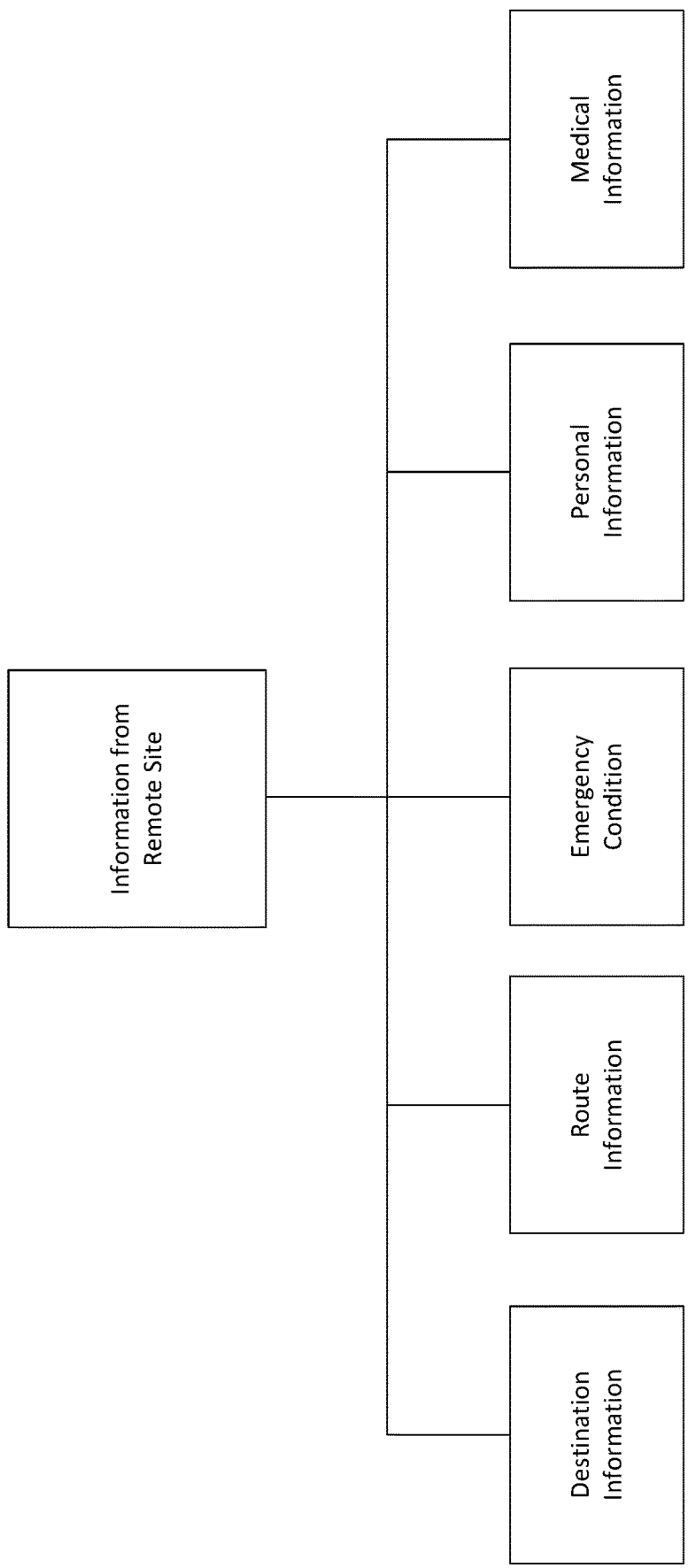
FIG. 14 shows examples of information provided by the remote site of the present invention.

The remote site 1104 can also provide information to the position-computing device 1110. FIG. 14 shows examples of information provided by the remote site 1104. For example, the remote site 1104 can provide information regarding the environment of the position-computing device 1110, such as information on a destination entered by the user into the position-computing device 1110. The destination can be a point of interest. As the user is traveling towards the destination, since the remote site 1104 can be made aware of the position of the position-sensing device 1102, route information can also be provided to the position-computing device 1110. Route information can, for example, depend on pre-programmed maps or include current traffic conditions. For example, an accident has just occurred on the freeway and traffic is held up. Such information can be transmitted to the user. In one embodiment, the remote site 1104 can send emergency conditions to the position-computing device 1110. For example, any emergency conditions, such as fire, flood and explosion, within a five-mile radius from a position-sensing device will be sent to its corresponding position-computing device 1110.

The remote site 1104 can provide information regarding a user to the position-computing device 1110. The information can be personal to the user of the position-computing device 1110. In one example, the information provided by the remote site 1104 can be medical in nature. For example, the user's heart beat is irregular and there is a hospital close to where the current position of the user. The remote site 1104 can suggest that the user visit the hospital, and provide the user with the corresponding directions. The hospital can also be notified of the imminent arrival and/or condition of the user by the remote site 1104 or the position-computing device 1110.

Figure 15:
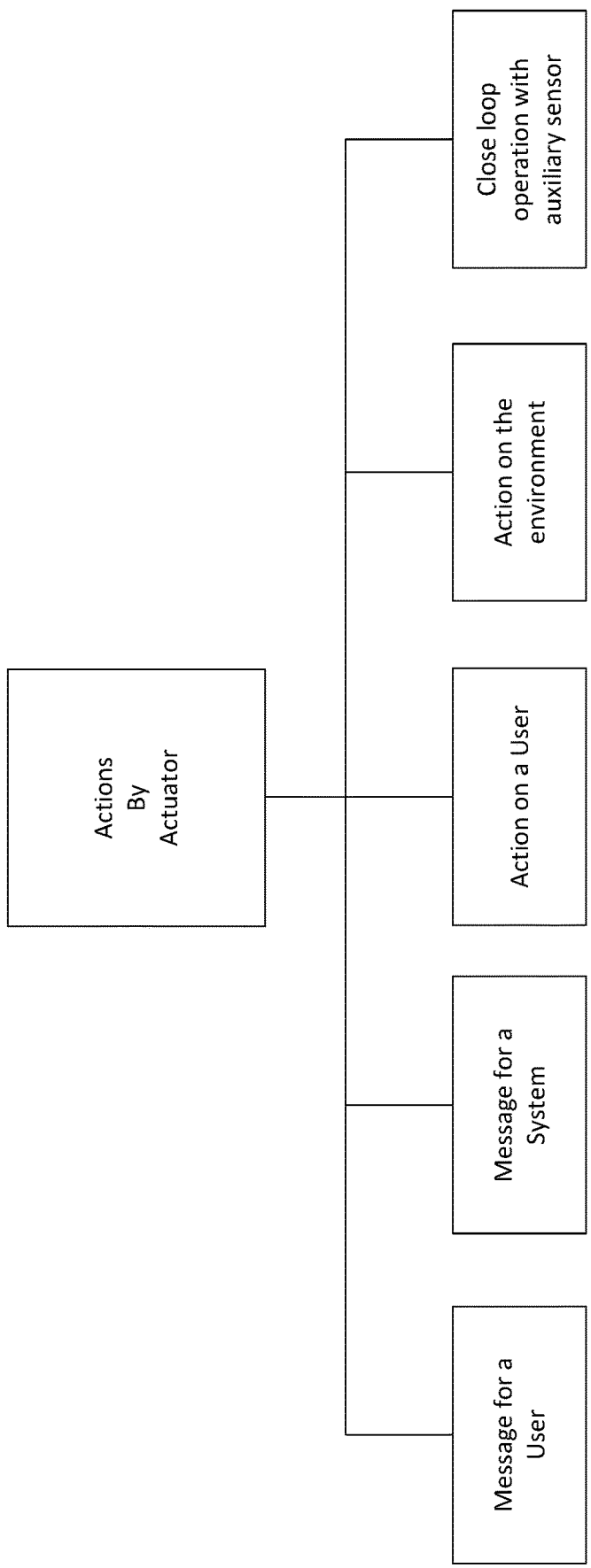
FIG. 15 shows examples of actions performed by an actuator of the present invention.

In one embodiment, the position-computing device 1110 is also coupled to the actuator 1106. In view of an analysis performed by the position-computing device 1110 and/or the remote site 1104, the actuator 1106 can be controlled to perform an action. FIG. 15 shows examples of actions performed by the actuator 1106. In one embodiment, the action is a message to a user of the position-computing device 1110 or to another person. The message can include text, audio or graphics. The message can describe certain actions the recipient should perform. The message might simply be an alarm, which can be a flashing red light or an audible tone. The action performed by the actuator 1106 can also be a message for a different system. Based on the message, the different system can initiate an action.

In another embodiment, the action performed by the actuator 1106 can be an action directly on a user. For example, in view of auxiliary information regarding the user's glucose level, the actuator 1106 can inject small doses of insulin into the user's blood stream.

In still another embodiment, the action performed by the actuator 1106 is an action on the environment or the surroundings in the vicinity of the position-sensing device 1102. For example, the action can be increasing the power to a heater to increase temperature, or to speed up a fan to decrease temperature.

Auxiliary sensors and actuators can work in a closed-loop situation so as to reach a pre-set point. For example, as a temperature sensor monitors the temperature of an environment, an actuator adjusts the speed of a fan or the power to an air-conditioner until a certain optimal or pre-set temperature is reached.

Figure 16:
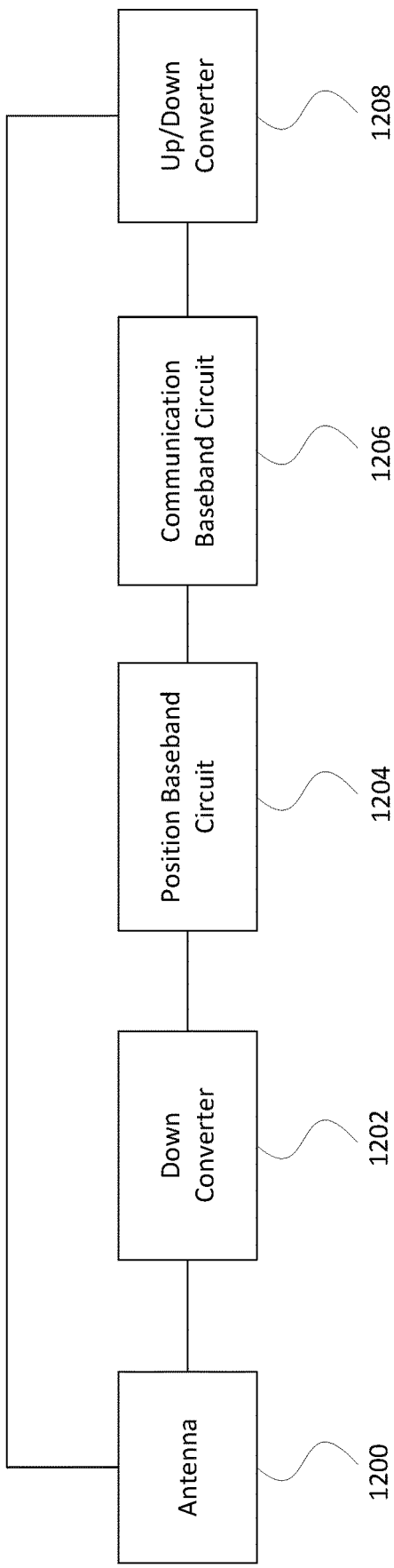
FIG. 16 shows one embodiment of the position-sensing device of the present invention.

FIG. 16 shows a position-sensing device according to one embodiment of the invention. The position-sensing device shown in FIG. 16 is suitable for use as the position-sensing device 1102 shown in FIG. 10. The position-sensing device includes an antenna 1200, a down converter 1202, a position baseband circuit 1204, a communication baseband circuit 1206, and an up converter 1208. The up converter 1208 may also serve as a down converter in another embodiment. Under that situation, the up converter 1208 can be known as an up/down converter. The following description is directed towards an embodiment that makes use of GPS to sense position, but it should be understood that the position-sensing device could use other technologies besides GPS.

In one embodiment, the antenna 1200 receives GPS RF signals and can also receive and transmit communication RF signals. After GPS RF signals are captured, the down converter 1202 down-converts such signals received from the antenna 1200 to lower frequency signals or baseband signals for further processing.

The position baseband circuit 1204 extracts raw position data from the GPS baseband signals. The raw position data are related to the pseudo-ranges from GPS satellites. Typically, a GPS baseband processor uses a digital signal processor core, which controls a set of GPS correlators. These correlators are usually set up to acquire and track the GPS satellite signals so as to produce the raw position data.

In one embodiment, raw position data are pseudo-ranges. Pseudo-ranges are typically estimates of distances between position-sensing devices and GPS satellites. In another embodiment, raw position data are from signals captured by the position-sensing device, but are less processed than pseudo-ranges. For example, as the GPS signals are received from the satellites, the position-sensing device does not perform the tracking calculations needed to maintain a closed tracking loop. Instead, the tracking calculations are performed by the position-computing device to generate, for example, pseudo-ranges, which are then used to generate a position. In this example, raw position data sent to the position-computing device are less processed than pseudo-ranges. The position generated can be, for example, the longitude and latitude of the position. In yet another embodiment, raw position data are information that needs additional processing before their corresponding position, such as its longitude and latitude, can be identified.

In one embodiment, the position-sensing device does not convert the raw position data to identify the position of the position-sensing device. Instead, the raw position data are sent to the position-computing device 1110, which will then compute a position based on these data. In another embodiment, these raw position data can be sent, via cellular link, to remote servers for position calculations. In either case, the position-sensing device does not have to perform the intensive position computations requiring processing capability from additional circuitry and consuming more power.

Figure 17:
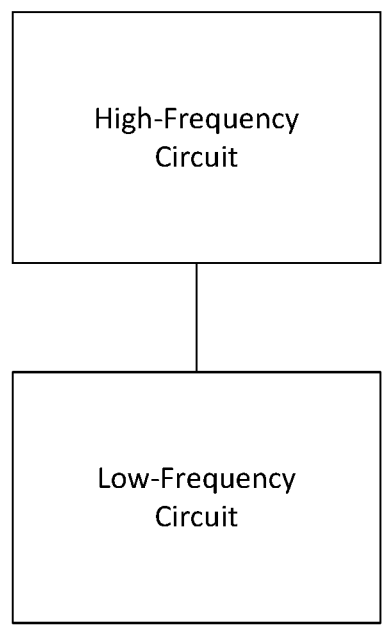
FIG. 17 shows one embodiment of the position-sensing device of the present invention having a high-frequency and a low-frequency circuit.

In one embodiment, to minimize space, and to reduce power consumption under certain circumstances, many components shown in FIG. 16 in the position-sensing device are integrated into a high-frequency circuit and a low-frequency circuit (FIG. 17). Sometimes, the high-frequency circuit can be called the analog circuit, while the low-frequency circuit, the digital circuit. For example, the GPS down converting and the communication up/down converting functions are integrated into the high-frequency circuit; and the position baseband circuit and the communication baseband circuit are integrated into the low-frequency circuit. The high-frequency circuit can be on a chip or substrate, and the low-frequency circuit can be on another chip. This results in a two-chip solution for a position-sensing device. In yet another embodiment, all these circuits could be on a common chip where high-speed analog circuits and digital circuits operate satisfactorily on the same substrate. If the antenna is an integrated-circuit antenna, to reduce loss, the antenna may not be on the same substrate as the other circuits, but can be on a separate low-loss material. In another embodiment, a chip or a substrate can be a circuit board instead.

Figure 18:
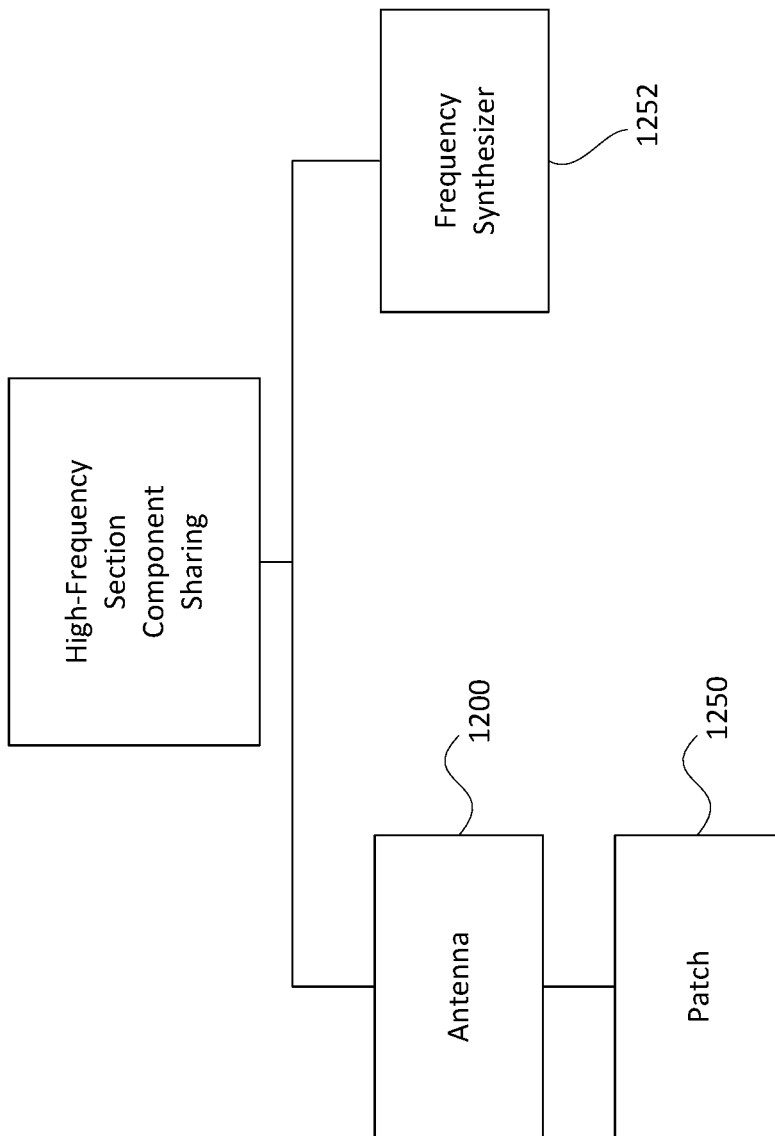
FIG. 18 shows examples of component sharing in the high-frequency section of the position-sensing device of the present invention.

Certain components in the high-frequency section of the position-sensing device can be shared. FIG. 18 shows examples of such sharing. Both the GPS RF signals and the communication RF signals can share the same physical antenna 1200. In one embodiment, the antenna 1200 can be a patch antenna 1250. Both the GPS RF signals and the communication RF signals can also share the same frequency synthesizer 1252, locked to a common timebase such as a crystal oscillator.

Figure 19:
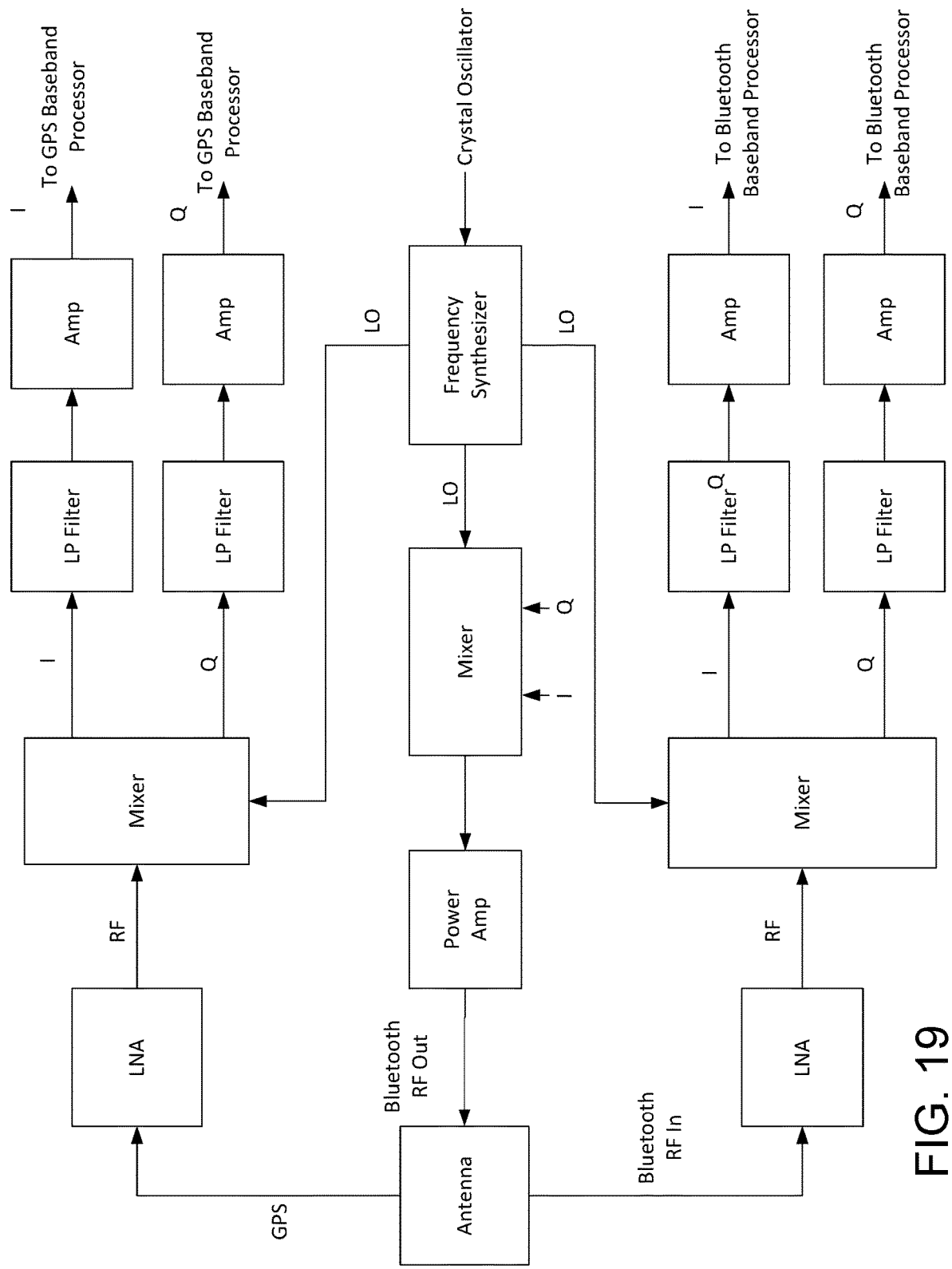
FIG. 19 illustrates one example of a high-frequency circuit of the position-sensing device of the present invention.

FIG. 19 shows one embodiment of the high-frequency circuit, using GPS and Bluetooth to illustrate different features. First, regarding the signal path of the GPS signals, an antenna receives the GPS RF signals, which are then amplified by a low-noise amplifier (LNA). The subsequent RF signals are down-converted to lower or baseband frequencies. This can be done by a mixer that mixes the RF signals with a LO signal from a frequency synthesizer. The mixer can be an image-reject mixer. The frequency synthesizer can be controlled by a temperature-compensated voltage-controlled external oscillator or timebase, which can be a crystal oscillator. The mixer output typically includes two signals, I and Q signals, which are in phase quadrature with each other. Both signals are amplified and then sent to a GPS baseband processor.

For the Bluetooth signals to be transmitted by the position-sensing device to the position-computing device, a mixer receives the I and Q signals from a Bluetooth baseband processor. The mixer, serving as an up converter, converts the two sets of signals to RF signals by mixing them with a LO signal from the frequency synthesizer. The communication RF signals are then amplified by a power amplifier to generate the Bluetooth RF output signals. The antenna then transmits the RF output signals to the position-computing device.

The position-computing device can also send Bluetooth RF input signals to the position-sensing device. This can be, for example, control signals for power conservation, configuration or other functions. Other functions can include initiating an action of accessing raw position data, or transmitting data to the position-computing device. As shown in FIG. 19, the Bluetooth RF input signals can go through similar signal processing as the GPS RF signals, but the I and Q signals are transmitted to the Bluetooth baseband processor. In this case, the mixer along the signal processing path can serve as a down converter.

A number of components are not shown in FIG. 19. For example, a mode switching circuitry with 3-wire bus input can be used to control the different modes of operation. In addition, there can be on-chip diplexers to control signal traffic for the different modes. There may be other passive components like filters for processing the RF and baseband signals.

Figure 20:
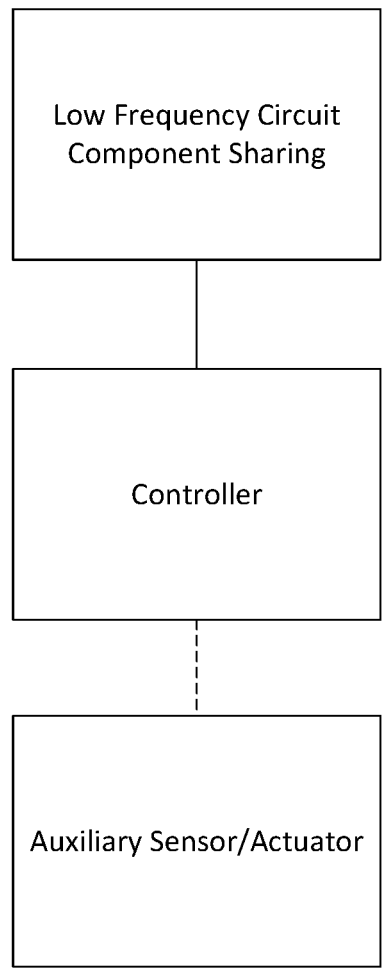
FIG. 20 shows examples of component sharing in the low-frequency circuit of the present invention.

Similar to the high-frequency circuit, certain components in the low-frequency circuit can be shared. FIG. 20 shows examples of such sharing. The communication signals and the GPS signals may share the same controller. An auxiliary sensor or an actuator can also share a controller.

Figure 21A:
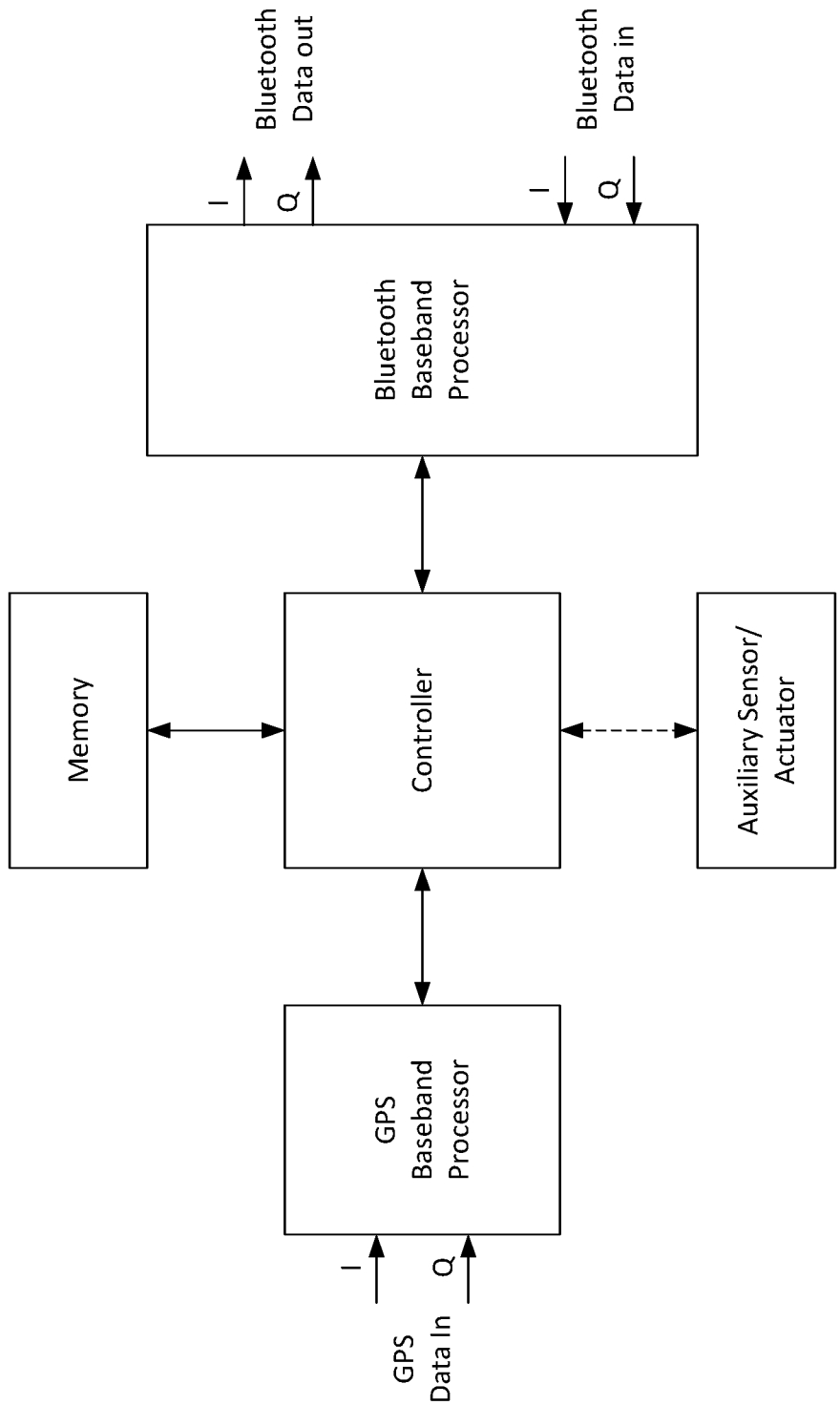
FIG. 21A shows one embodiment of low-frequency circuit of the position-sensing device of the present invention.

FIG. 21A shows one embodiment of the low-frequency circuit, again using GPS and Bluetooth to illustrate different features. The GPS baseband processor receives and analyzes the GPS quadrature data, the I and Q signals. The GPS baseband processor is controlled by a controller with on-chip memory.

The Bluetooth baseband processor receives and analyzes the Bluetooth quadrature data from the Bluetooth RF input signals. The Bluetooth baseband processor is also responsible for generating the Bluetooth quadrature data, the I and Q signals, for the Bluetooth RF output signals. The Bluetooth baseband processor is controlled by the controller. The controller can have a separate and dedicated communication processor. In such a case, the logic circuitry of the controller will be simplified.

The controller can also be used to control one or more auxiliary sensors and/or one or more actuators. These auxiliary sensors and/or actuators can be integrated to the circuits of the position-sensing device, such as the low-frequency circuit, or can be on separate circuits/chips, or can be external to the device.

Figure 21B:
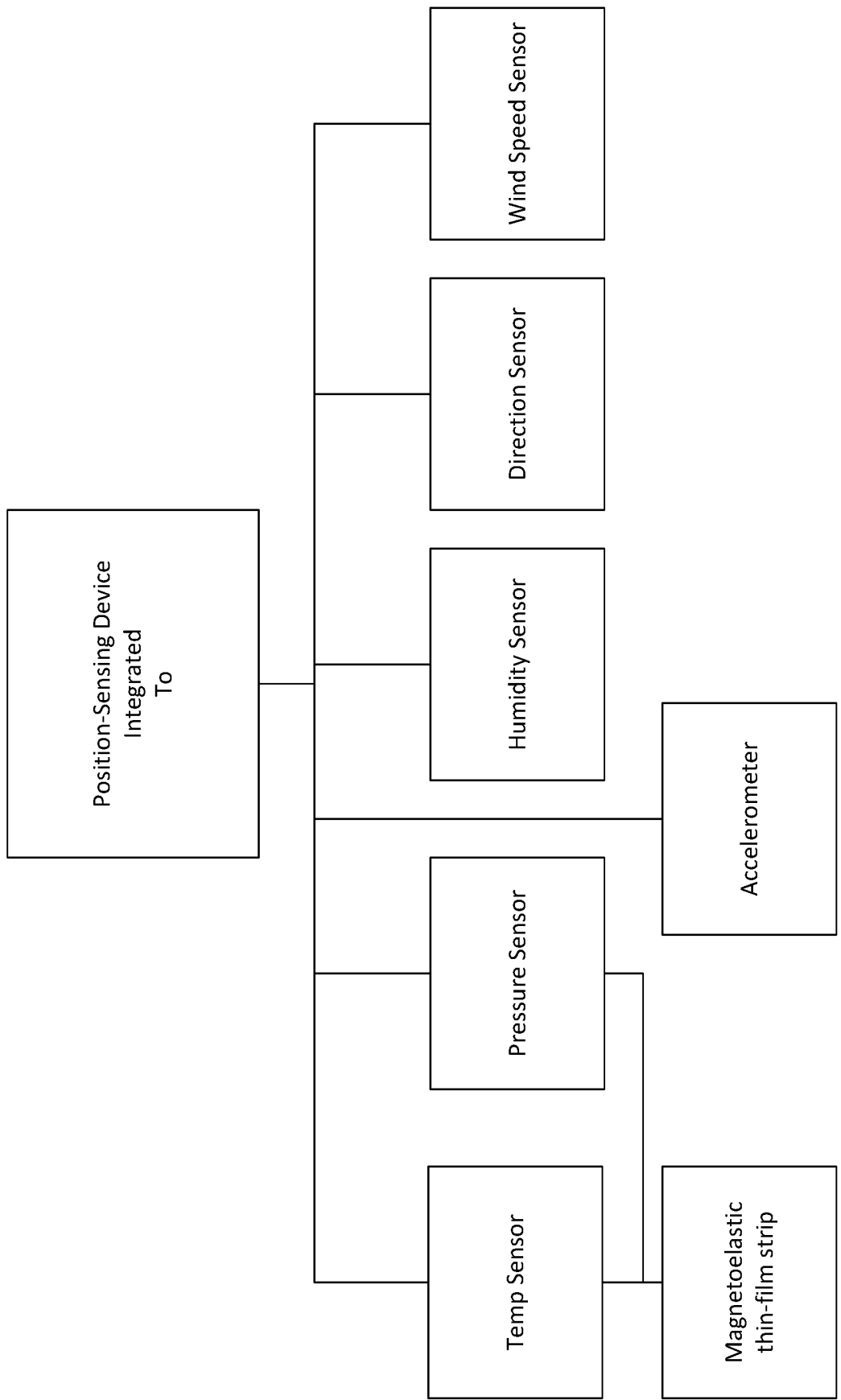
FIG. 21B shows examples of integrating a position-sensing device with different types of auxiliary sensors.

FIG. 21B shows examples of integrating a position-sensing device with one or more different types of auxiliary sensors. Other types of auxiliary sensors can be integrated. FIG. 21B provides examples for illustration purposes. The device can be integrated to a temperature sensor, a pressure sensor, an accelerometer, a humidity sensor and a wind speed sensor. The integration can be through integrated-circuit techniques, such as having one or more of auxiliary sensors on the same integrated circuit as the position-sensing device. Or, the integration can be through packaging, where one or more auxiliary sensors are in the same package as the position-sensing device.

An example of a temperature sensor is a magnetoelastic thin-film strip. The material's magnetic response changes when it is heated or cooled. A magnetoelastic thin-film strip can also be used as a stress sensor, again through monitoring its magnetic response. Such a strip can be, for example, one inch in length.

In another embodiment, two or more different types of auxiliary sensors are integrated together, without a position-sensing device.

Figure 22:
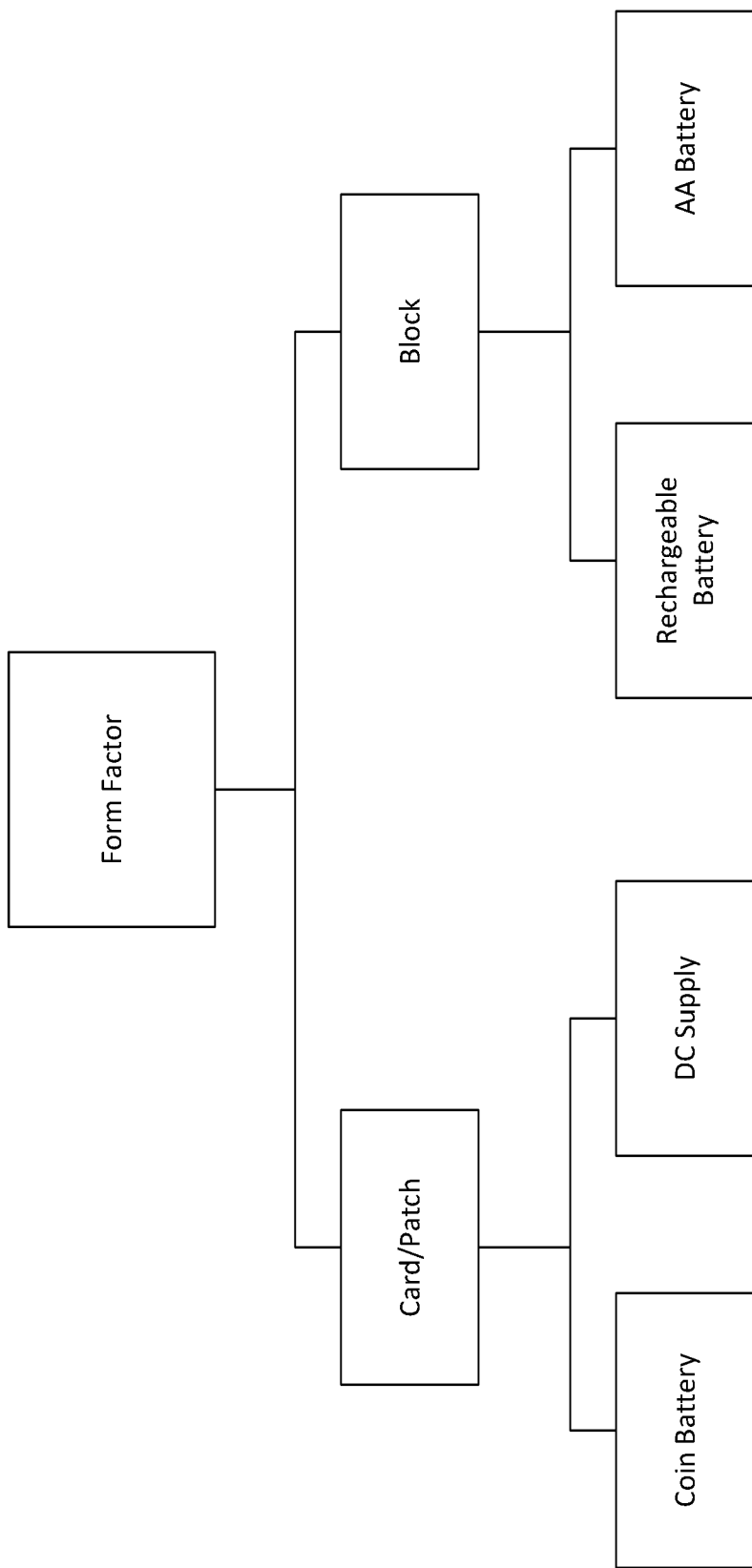
FIG. 22 shows examples of the position-sensing device form factor of the present invention.

The position-sensing device can be made relatively compact, enhanced through circuit integration. FIG. 22 shows examples of the position-sensing device form factor. The position-sensing device can be the size of a patch or a card (e.g., memory card or PC Card). The antenna can be a patch antenna. A patch can be a structure whose thickness is less than 0.5 inch and whose surface area is less than 2 square inches, or more preferably 1 square inch. In this situation, power can be from a dc power supply or a battery (e.g., coin battery). The dc power supply can be from the cigarette lighter outlet of a car or from an ac outlet with an external transformer. Certain features described in U.S. Provisional Patent Application No. 60/404,645, filed Aug. 19, 2002 can be incorporated into the position-sensing device to reduce power consumption.

In another embodiment, the size of the position-sensing device is thicker, more in the shape of a block. In this situation, the size is influenced by the size of its power source. For example, power can be from a rechargeable battery or from AA batteries.

Figure 23:
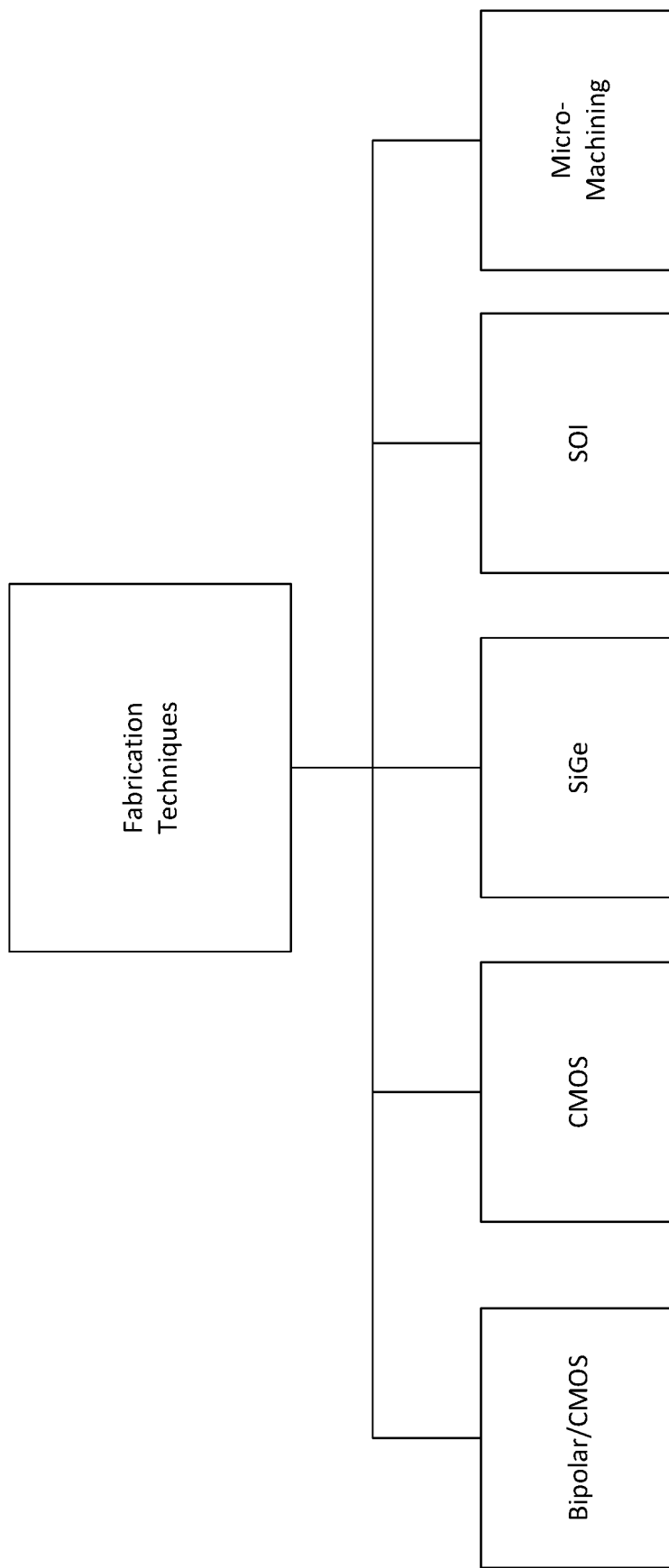
FIG. 23 shows examples of fabrication techniques for the present invention.

Different techniques may be used to fabricate different circuits described. FIG. 23 shows a few examples. The high-frequency circuit can be fabricated by bipolar processes, while the low-frequency circuit by CMOS processes. In one example, both the high and low frequency circuits are fabricated by CMOS processes. Other processing technologies can be used, such as BiCMOS, SiGe or SOI (Silicon-On-Insulator).

In one approach, an auxiliary sensor includes a mechanical device that can respond to mechanical forces. It can be fabricated by micromachining techniques. Devices made by micromachining techniques can also be known as micro-electromechanical systems or microsystems. The micromachining techniques include semiconductor processes. The auxiliary sensor can be integrated with the position-sensing device, such as on the low-frequency chip.

An example of an auxiliary sensor made by micromachining techniques is a pressure sensor. It can include a square membrane bulk-etched in a silicon wafer. This process etches away most of the thickness of a region of the die, called the diaphragm. Then piezoresistive (stress sensing) transducers can be deposited through diffusion to create a resistive bridge type structure. The etching process used to create the thin diaphragm can make the silicon wafer more fragile and susceptible to breakage during handling. To reduce in-process damage, the etch process can be performed as the last major photolithography step. The sensor can then be separated from the wafer, and bonded to a glass or Pyrex plate, or to a ceramics plate to increase its mechanical strength.

Figure 24:
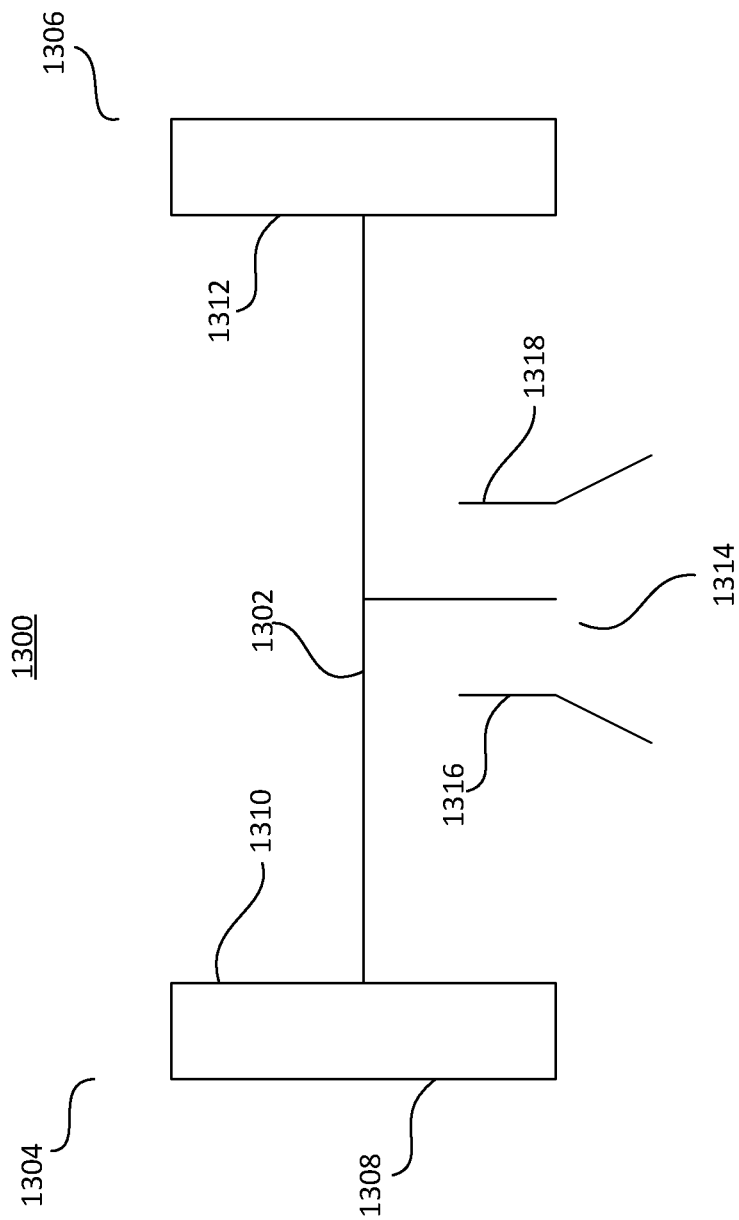
FIG. 24 shows an example of a micromachined accelerometer for the present invention.

Another example of such an auxiliary sensor made by micromachining techniques is a capacitive accelerometer or inertia sensing element. It can be a bulk micromachined capacitive accelerometer on a substrate. FIG. 24 shows an example. The accelerometer 1300 incorporates a moving inertial mass 1302 suspended by springs attached to a surrounding frame structure, which can be the substrate. There can be two springs 1304 and 1306, one connected to each end of the moving inertial mass. Each spring can be micromachined beams in the shape of a rectangular box, with two long beams connected at their ends. One of the long beam 1308 of the spring 1304 is stationary and is attached to the frame structure. The other long beam 1310 is a movable or flexible beam. That long beam 1310 is connected to one end of the inertial mass 1302, whose other end is connected to the long beam 1312 that is movable and flexible, of the other spring 1306. Again, the other long beam of the spring 1306 is stationary and is attached to the frame structure.

The inertial mass 1302 has a metallic finger 1314. The finger 1314 is positioned between two stationary metal bars, 1316 and 1318, on the frame structure. The distance between the finger 1314 and each of the metal bar changes as the inertial mass 1302 moves. This creates a variable capacitance between the moving inertial mass and each of the metal bars. There can be many fingers, each positioned between two bars, so as to have higher capacitance. To measure two axes of acceleration, two such accelerometers, positioned orthogonal to each other, can be used.

Yet another example of an auxiliary sensor made by micromachining techniques is for measuring information regarding a living being. In one embodiment, sensors made by such techniques can take very small amount of materials from the being as samples for measurement.

The auxiliary sensor may not have to include a mechanical device. For ease of integration, such auxiliary sensors can be fabricated by semiconductor processing techniques similar to those used in the position-sensing device. For example, the auxiliary sensor is a temperature sensor implemented with a diode. The diode can be fabricated on the same piece of substrate as the low-frequency circuit of the position-sensing device. Assume the circuits of the device are in an enclosure. The temperature gradient between the inside of the enclosure and the outside ambient of the position-sensing device can be calculated or measured. The temperature as measured by the diode on the substrate can be calibrated to subtract out the gradient. This will more accurately reflect the outside ambient temperature. In one embodiment, the temperature sensor is implemented with a thermal couple.

The auxiliary sensor can be in the same package as the position-sensing device but not share the same substrates as the circuits in the position-sensing device. For example, the temperature sensing diode can be separately encapsulated or enclosed, with the enclosed diode exposed to the outside environment, and with its leads bonded to circuitry in the position-sensing device. As another example, the geometry of the auxiliary sensor can be much bigger than the numerous circuit components of the position-sensing device. To illustrate, the diaphragm in a micromachined pressure sensor can occupy significant area. This area can be quite expansive if it is on the substrate of the low frequency circuit of the device. Hence, the auxiliary sensor can be on a separate substrate or circuit board.

In one embodiment, different chips or circuit boards described are stacked, one on top of the other, instead of having one substantially on the same plane as the other.

In yet another embodiment, an actuator also includes a mechanical device that can exert mechanical forces, and is fabricated by micromachining techniques. For example, the micromachined actuator is for administering small doses of insulin into a person's blood stream.

In one embodiment, some of the high-frequency components in the device are also fabricated by micromachining techniques.

In one approach, the micromachining process is a bipolar process. In another, it is a CMOS process. In yet another approach, it is a BiCMOS process.

In one embodiment, a position sensing system can include more than one type of position detection mechanisms. Such a system can be known as a multi-type position sensor. For example, two types of position detection mechanisms can be a GPS sensor and a RF ID tag. In one embodiment, the RF ID tag can be integrated with circuitry of the GPS sensor. In another embodiment, the GPS sensor and the RF ID tag are on separate substrates or circuit boards, or in separate enclosures. In yet another embodiment, the RF ID tag is on a plastic substrate. The GPS sensor can provide more coarse position information, while the RF ID tag provides finer position information. In another example, the GPS sensor can provide position information in an outdoor environment, while the RF ID tag can provide for position information in an indoor environment, such as a large warehouse. The multi-type position sensor can include a position-sensor selector. When the multi-type position sensor is in transit from one warehouse to another, the selector activates the GPS sensor to track position. When the multi-type position sensor is moved into a warehouse, the selector would select the RF ID tag to take over the position-sensing responsibility. As another example, two types of position detection mechanisms can be a GPS sensor and a local wireless network sensor (e.g., Bluetooth or Wi-Fi transceiver). In one embodiment, a multi-type position sensor, or at least the GPS sensor within the multi-type position sensor, extracts raw position data, but does not convert the raw position data into the position of the multi-type position sensor.

Figure 25:
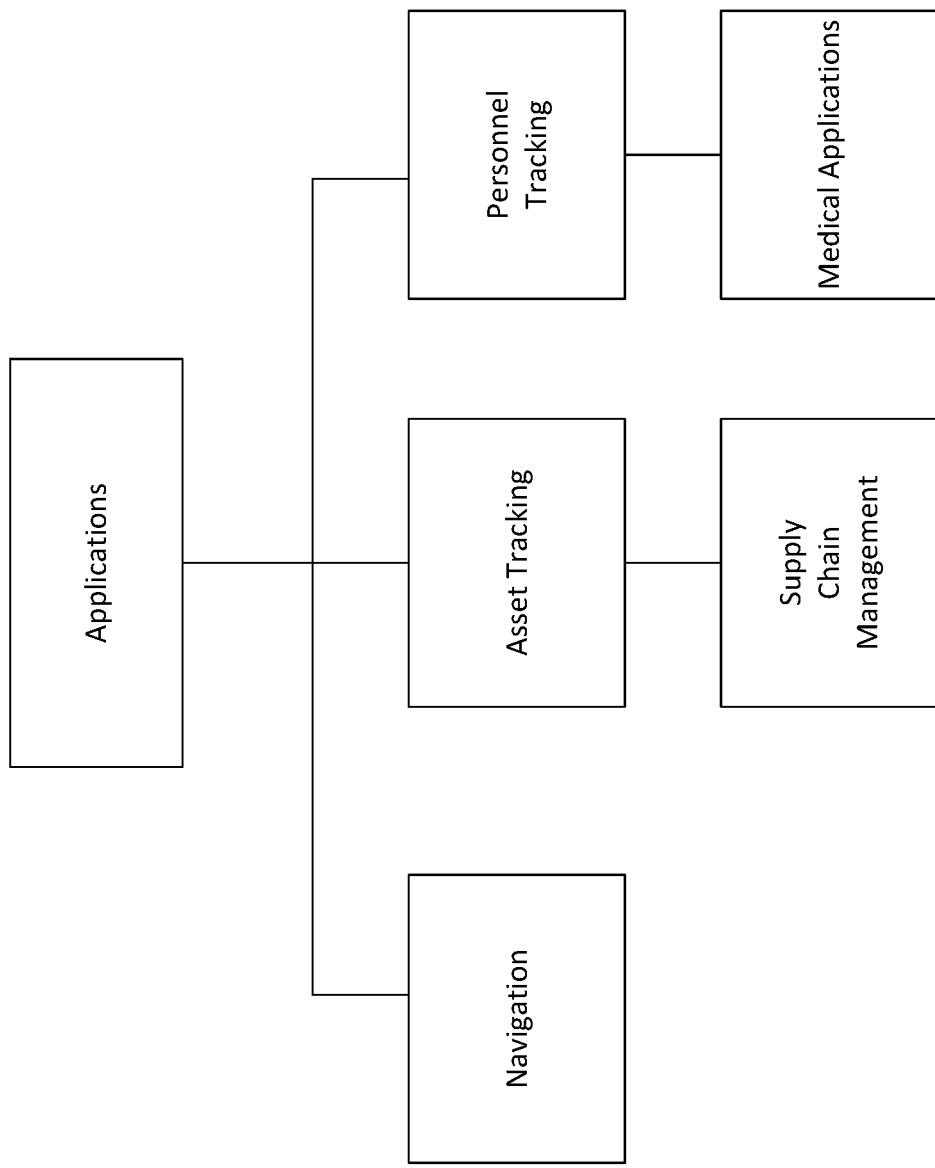
FIG. 25 shows examples of applications for the present invention.

FIG. 25 shows a few examples of applications for the present invention. One application is in navigation. The position-sensing device can be attached to the top of the dashboard or to the rear window of a car. The position-computing device can be a PDA next to the driver or in the driver's pocket. The PDA can contain a navigation program that performs route calculations, based on user input (e.g., a destination location), with a map database stored in the PDA's memory. The map may be downloaded from a remote site. The downloading can be performed before or after the destination position has been entered into the PDA. The navigation program allows the driver or a passenger to enter a destination position, e.g., in the format of a street address or a point on a map display. The program then can compute a route based on the map database to guide the driver to that destination. Such guidance can be in the form of turn-by-turn voice instructions. As an example, a car rental company can incorporate such technologies into its car rental policy and offer them as an additional feature.

Another application is in the area of asset tracking and management. A cost-effective asset tracking system can be built based on a number of embodiments described. For example, a position sensor can include a low-cost GPS position-sensing device and a position-computing device (e.g., PDA with cellular or other wireless communication ability). The position-computing device can also be wirelessly connected to a remote station or site.

In one embodiment, products/materials can be tracked by a position sensing system. This can be used in supply-chain management. When a product requires multiple parts/materials to be assembled or integrated together, to have each of the right parts/materials available at the appropriate time is sometimes critical to success. To reduce total costs, a company has to control the amount of materials/parts at rest (inventory) and the speed and costs of materials/parts in motion (freight). If different parts/materials come from different channel partners, to control cost, the company may want to work with their partners to keep their assets (the parts/materials) moving to the company at the minimum level needed to keep customers satisfied. To achieve that, the company should know where the different parts/materials are and to control the rate they are transported. Not only would this help the company lower its expense by reducing its inventory, the company can better satisfy its customers with sufficient inventory.

A piece of inventory can be in freight or it can be in a large warehouse. Sometimes, the piece of inventory has to be tracked in both situations. In one embodiment, the position sensing system can include two types of position sensors—a multi-type-position sensor. One position sensor (a GPS sensor) is for sensing the inventory when it is being transported from an airport to a warehouse, and the other (such as a RF ID tag or a bar code) for sensing its location inside the warehouse. In another embodiment, a piece of large inventory can include many sub-pieces. The piece of inventory can be tracked by a GPS sensor, and may also be tracked by a RF ID tag. Once inside the warehouse, the piece of inventory can be transported to a center, where it is unpacked, with a number of the sub-pieces separately distributed through the warehouse. Each sub-piece can be identified and tracked within the warehouse by its individual bar-code or RF ID tag.

The inventory location information can be wirelessly entered into a warehouse management system, which allows users to see the status of incoming goods, outgoing shipments, and available inventory. Reports can also be generated. The warehouse management system can allow the inventory to be managed in real time. Such information is useful for procuring, maintaining, transporting and delivering products through every stage of production from the source of supply to the final point of consumption. Such information could also assist in providing an audit trail for accounting purposes.

The above embodiments describe tracking inventories, such as, by the management. However, a consumer can track a piece of inventory as well. A typical supply chain includes four entities—manufacturer, wholesaler, retailer and consumer. In one embodiment, a consumer can drive what a manufacturer should produce and ship. For example, the consumer can get in touch with the call center of the retailer, or enters his request into the retailer's web site. Such a request can directly go to the manufacturer, which would assemble the product to be shipped to the consumer. Based on a number of the embodiments of the present invention, the consumer can track the location of his request in real time, such as through a web site. Thus, the consumer directly drives what should be produced and shipped, and tracks his shipment, from inside a warehouse to his door step.

Another example of involving a consumer is for products at least partially assembled by the consumer. A retailer can have thousands of components in the store. It is up to the consumer to pick and choose the components desired for subsequent integration. If the consumer selects two components, manufactured by two different manufacturers, the retailer can place the order to the two manufacturers. One goal of the retailer may be to ensure that both components arrive around the same time at the retailer's store. The two components can be ready for shipment at different time. Or, the two components can arrive at different time frames, even if they are shipped at the same time. This can be due to differences in locations or differences in delivery method. One approach to achieve the retailer's goal is to allow the component that needs more time (long-time component) before reaching the retailer dictate the delivery of the other component. For example, when the manufacturer of the long-time component is ready to ship its component, that component is shipped, with its position tracked by an embodiment of the present invention. Only when the long-time component is within a certain distance to the retailer, the retailer initiates the delivery of the other component. In other words, the retailer (or the system automatically) changes the delivery time of the other component based on the position of the long-time component. When both components arrive, the retailer/system can notify the consumer.

In tracking assets, a position sensor can include additional auxiliary sensors, such as temperature and humidity sensors. The following illustrates an example of asset tracking based on a position sensor and an auxiliary temperature sensor.

Assume that a company needs to produce a product that requires two very expensive parts to be integrated together at a warehouse. One part is manufactured by a local sub-contractor. The other part is from a remote sub-contractor thousands of miles away. This other part is also temperature sensitive. Due to cost and liability, the company does not want to order and store any one of the two parts in the warehouse unless the product has to be produced. Assume an order is received for the product. The company has a supply-chain management controller, which can include a warehouse management system. The controller automatically requests the sub-contractors to make and ship the parts so that the company can produce the ordered product as needed.

Assume the temperature-sensing part is ready and is shipped first. Once shipped, the controller tracks the temperature-sensitive part in motion based on a position sensor. The controller is also aware of the temperature of the ambient surrounding that part based on an auxiliary sensor. Assume the temperature-sensitive part becomes defective during shipment due to accidental temperature rise, even though the part is still thousands of miles away from the company. Since the temperature sensor sends information to the controller, the controller is aware that the temperature-sensitive part has to be replaced. Based on such information, the controller automatically orders the local sub-contractor to hold delivery of its part, until the remote sub-contractor is ready to ship a new temperature-sensitive part to the company.

Such real-time location and/or auxiliary information notification and control are very helpful for a company to manage its inventory. Such information is not only applicable to asset tracking/management, supply chain management or product management, but also can be applied to enterprise resource planning and customer relationship management. For example, in customer relationship management, a call center support staff can inform a customer of the location and condition of her product. Alternatively, a customer can access real-time information (e.g., location and condition) via a web interface or by receiving notifications (e.g., email notifications).

Personnel tracking can be another application. For example, additional auxiliary sensors such as body temperature or blood oxygen sensors, or heart-beat monitors can provide important physical health parameters to interested persons (e.g., health professionals) wishing to monitor the position and well-being of their clients. Personnel tracking can also include tracking of other forms of living beings, such as animals.

Different examples of sensors have been described. In one embodiment, a sensor not only can sense but can also transmit information regarding an object. For example, the sensor is a RF ID tag with information stored in the tag about an object. The tag can transmit such information to a recipient.

In a number of embodiments, not only can the size of the position-sensing device be made compact, the position-sensing device can be relatively inexpensive. For example, to reduce cost and size, the position-sensing device does not have a display or keyboard entry for user input. Information can be received and transmitted wirelessly. Also, the position-sensing device does not have to include circuitry to perform processing to calculate its position or determine actions.

A number of devices have been described where the position-sensing device is separated spatially from the position-computing device. Alternatively, the position-sensing device and the position-computing device are in one package.

A number of embodiments have been described that include a position-computing device. One embodiment does not include a position-computing device. Instead, its function is performed by a remote site. The corresponding position-sensing device directly communicates with and is controlled by the site. In this embodiment, auxiliary sensors and/or actuators can also communicate with and be controlled by the site. As an alternative embodiment, the position-sensing device can collect information from, and distribute information to, the additional auxiliary sensors and/or actuators. In other words, the position-sensing device communicates with the site on behalf of the auxiliary sensors and/or actuators.

Figure 26:
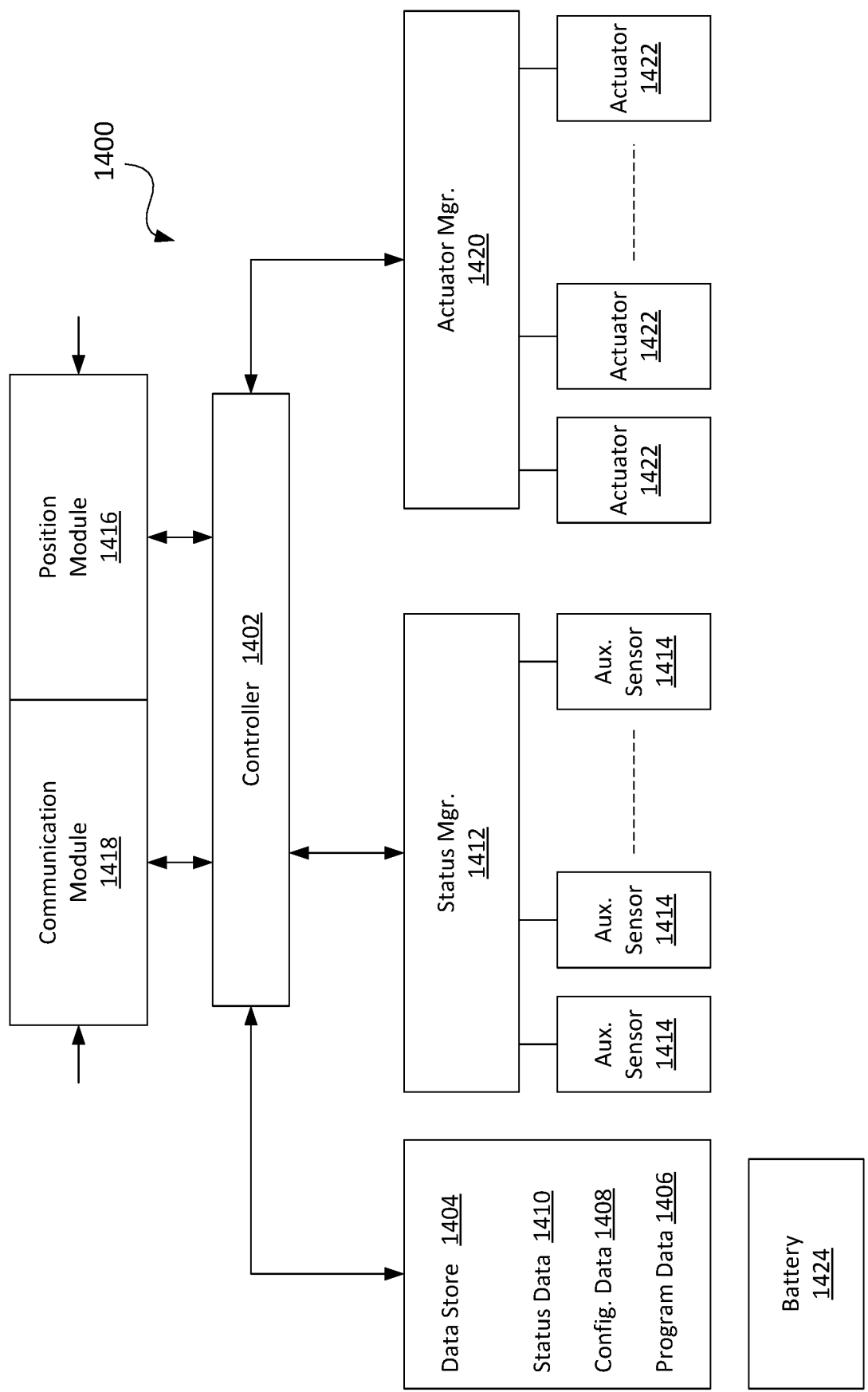
FIG. 26 is a block diagram of a mobile device according to one embodiment of the invention.

FIG. 26 is a block diagram of a mobile device 1400 according to one embodiment of the invention. The mobile device 1400 is suitable for use as a position sensing system, a medical monitoring device, a position tracking device, or other positioning device.

The mobile device 1400 includes a controller 1402 that controls overall operation of the mobile device 1400. A data store 1404 is connected to the controller 1402 and provides storage of data. The data stored in the data store 1404 can include program data 1406, configuration data 1408, and status data 1410. The status data 1410 are data related to the status of an object being monitored, such as position information and/or auxiliary information of the object. The status data 1410 are acquired by one or more auxiliary sensors. A status manager 1412 couples to the one or more auxiliary sensors 1414. The controller 1402 interacts with the status manager 1412 to obtain the status data 1410.

In addition, the controller 1402 couples to a position module 1416 and a communication module 1418. The position module 1416 can receive signals that are used to determine a position of the mobile device 1400. In one embodiment, the position module 1416 is a GPS receiver. The communication module 1418 allows the mobile device 1400 to communicate in a wireless manner. The wireless communications are over a wireless network (e.g., SMC network, a cellular network, a Bluetooth network, a Wi-Fi network, etc.). The wireless communication capabilities can be used to communicate with a remote server (e.g., send status data to the remote server), sending or receiving messages (e.g., notifications) to other mobile devices, or as an alternative or additional means of determining position.

The mobile device 1400 can also include an actuator manager 1420 that couples to one or more actuators 1422. The actuators 1422 can be controlled by the actuator manager 1420 to perform an action. The controller 1402 interacts with the actuator manager 1420 to direct any of the actuators 1422 to perform an action. FIG. 15 shows examples of actions that could be performed by the actuators 1420. For example, the action is a message to a user of the mobile device 1400, another person, a different system, or an action on a user.

The mobile device 1400 further includes a battery 1424 that supplies power to the mobile device 1400. The controller 1402, or a power manager (not shown), can also perform power management functions to reduce power consumption and thus extend battery life. For example, circuits or components can be power-off or placed in low-power mode when not active. Further, in one embodiment, the communication module 1418 and the position module 1416 can share components to reduce cost, die area consumption and power consumption (see, e.g., FIGS. 16-21).

Although the mobile device 1400 shown in FIG. 26 includes the status manager 1412 and the actuator manager 1420, such managers are not required as their operations can be performed by the controller 1402. However, when provided, managers can off-load processing from the controller 1402 to the managers which reduce processing load on the controller 1402. The mobile device 1400 can also facilitate power management by separately controlling power to the controller 1402 and any managers provided. In addition, the mobile device 1400 need not include any of the actuators 1422.

Figure 27:
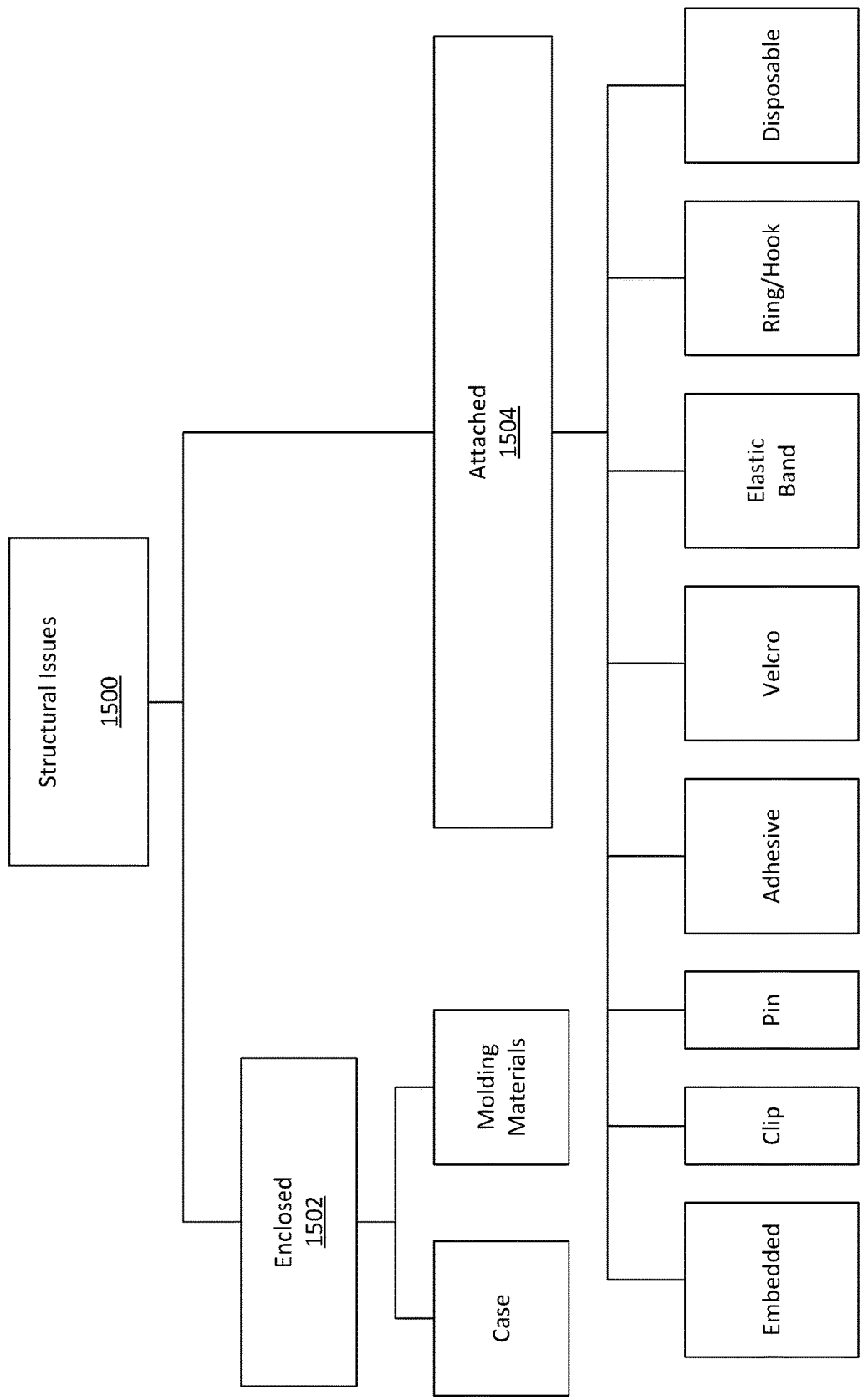
FIG. 27 shows a number of structural issues regarding the devices for the present invention.

As described, a number of embodiments of the present invention can be quite compact. FIG. 27 shows a number of structural issues 1500 regarding the devices for the present invention.

The circuits in a mobile device (e.g., a position sensing system, a position sensing device, a medical monitoring device, or a position tracking device) can be encapsulated or enclosed 1502 in a number of ways. For example, the circuits can be in a case or housing. The circuits can be enclosed by a molding compound. The molding compound can be epoxy, rubber, plastic or other materials. The enclosed circuits can become the housing of the device.

After the enclosing, the enclosed circuits of the mobile device can be attached 1504 to an object (e.g., a package) or a being (e.g., a person) in a number of ways. For example, the enclosed circuits can be in a module, with the module embedded as a unit into the object or being. A being can be a living being or a dead being, for example, a living person or a dead dog. The enclosed circuits can be attached (directly or indirectly) to the object or being through a clip and a pin. The enclosed circuits can be referred to as being wearable. Other attachment techniques include Velcro® and adhesive, either permanently, such as with a glue, or in a non-permanent manner, such as patches that are adhered to the body. The enclosed circuits can be attached with a band, such as an elastic band. The enclosed circuits can be attached by having a ring or a hook. The enclosed circuits can be worn as a necklace, bracelet or other types of fashionable item.

The enclosed circuits can be attached by a mechanism that is designed to be disposed or disposable. For example, the attachment can be through an adhesive tape that has an envelope or pocket. The enclosed circuits can be provided in the envelope, and the envelope can be closed such as by Velcro® or adhesive. The tape can be attached to an object. After finished using the circuits, a user can dispose of the tape, but keep the enclosed circuits.

One embodiment of the invention includes a solar panel. The solar panel can provide electrical power to, for example, a position-sensing device. The solar panel can thus charge a battery used to power the device and/or itself to power the device. When the device is affixed to an object (e.g., a package), the solar panel can remain at least partially exposed to the outside of the object so as to be able to receive light. The solar panel can be integrated with the housing of the device or can be separate and couple to the device via one or more wires (e.g., a cable). For example, the battery 1424 of the mobile device 1400 can be charged by a solar panel.

In one embodiment, a user can set permission levels. These levels can determine the identity of the person or system that can get information from different embodiments of the present invention, such as a position-computing device, a position-sensing device, a medical monitoring device, a mobile device and/or an auxiliary sensor. The permission levels can also include the time frame when a person or system can get the information. If the user desires, the user can even turn the device off. In that situation, no one has the permission to access information. This can be done, for example, through entering commands into or programming a position-computing device, a position-sensing device, a medical monitoring device, or a mobile device. In another embodiment, the permission can be set at a remote site that communicates with a position-computing device, a position-sensing device, a medical monitoring device or a mobile device.

In yet another embodiment, a position-sensing device or a position sensor is not active until a battery is inserted or a switch is turned on. The device might include a unique identifier, which can be a number. In another embodiment, the device is in a low power mode (e.g. sleep mode) but is programmed to wake up at certain times to listen for commands directed to it. For example, a position-computing device can transmit, through Bluetooth, to the device, a command and the unique identifier, which is used to identify the recipient device of the commands. Once the commands are received, the device becomes active.

Figure 28:
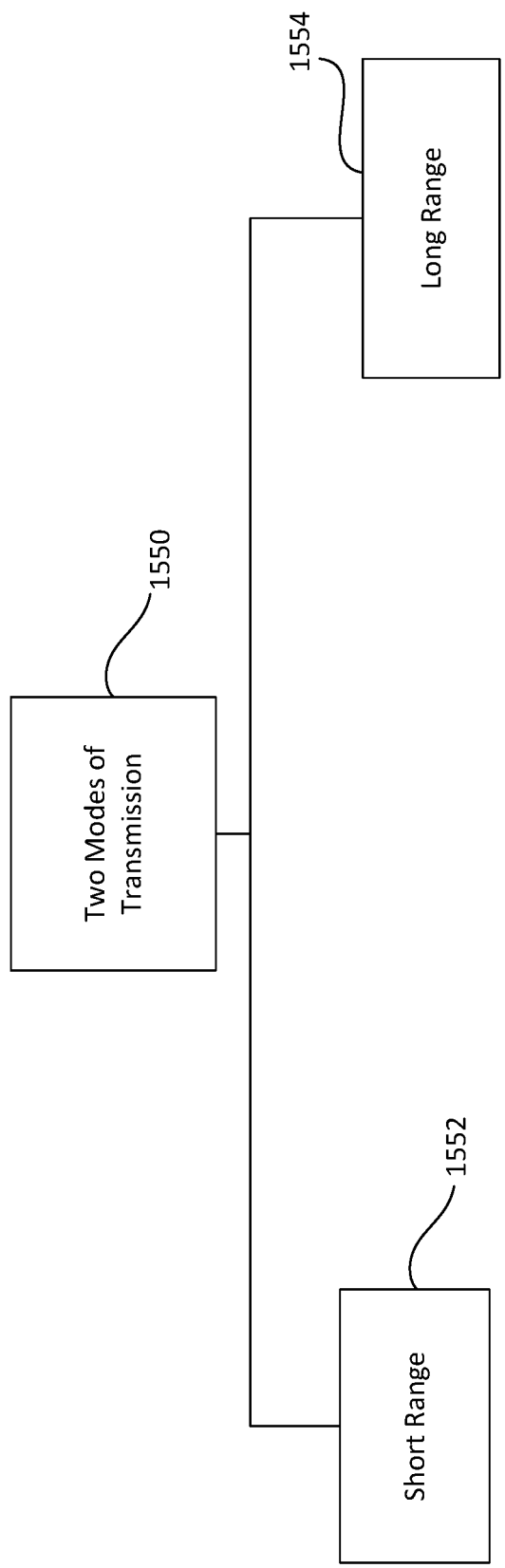
FIG. 28 shows one embodiment of the invention that includes two modes of transmissions.

In one embodiment, a position-sensing device includes two (2) modes of transmissions 1550, as illustrated in FIG. 28. Raw position data can be transmitted through either one of the two modes. One mode is short range 1552, and the other is long range 1554. The short-range transmission is to transmit, such as through Bluetooth, to a receiver in close proximity. Such transmission can be to a position-computing device in its vicinity (e.g., within 30 feet). The other mode is much longer range, such as to a Wi-Fi, cellular, or a pager network. This longer-range transmission consumes more power than the short range transmission. The destination for the long range transmission can be to a remote server. In another embodiment, the short-range transmission can be through Wi-Fi also, while the long-range transmission can be to a cellular or pager network.

In normal operation, the device prefers to transmit and receive signals using short-range communication. In one embodiment, after the position-sensing device has been activated, the position-sensing device starts in a short-range mode. If the position-sensing device is unable to communicate with a recipient or an intermediate system, the position-sensing device can switch to a long-range mode. For example, when the position-sensing device fails to receive either a signal requesting for position information or an acknowledgement to its transmitted signals after a preset duration of time, the position-sensing device will automatically switch to communicate in the long range mode with a recipient (e.g., a remote server). The position-sensing device can then periodically transmit its location to the remote server.

One application of the two modes of transmission is for theft prevention. Imagine a truck shipping a package that has a position-sensing device. During shipment, the position sensing device transmits its position information through short-range communication to a position-computing device attached to the truck. The position-computing device transmits the position of the package to the main office of the trucking company. Unbeknown to the driver, when he is having lunch at a restaurant, a thief breaks into his truck and steals the package. For the next hour, the position-sensing device never receives a signal requesting for location information or an acknowledgement to its transmitted signals. After the hour has elapsed, the position-sensing device can automatically send its unique identifier as a status signal, through a wireless (e.g., cellular) network, to the main office of the trucking company. If the signal is not received, the device can resend the signal every fifteen minutes. The office, after receiving the status signal, can request for the location of the package (i.e., the position-sensing device). The position-sensing device, getting the request, can transmit its location information through the wireless means to the office. Alternatively, the status signal could itself contain the location of the package. In either case, the office is notified of the location and thus is able to track the position of the stolen package.

In another embodiment, instead of transmitting through cellular means, the device transmits information using a Wi-Fi signal to tap into a Wi-Fi network. The Wi-Fi hub receiving the signal can direct it to a predetermined remote site, such as to the main office in the above example. The transmission of information from/to the position-sensing device can also be in a text message format (e.g., email or instant message). For example, the information can be transmitted over a SMS network or other pager type network.

A number of embodiments have been described where positions are identified based on GPS technologies. Other wireless technologies are also applicable, for example, using the techniques of triangulation. In one embodiment, the wireless technologies are based on a position-sensing device accessing or capturing television signals from such as three TV signal transmission towers. Triangulation techniques are then performed using synchronization codes in the TV signals to identify the location of that position-sensing device. In embodiments where positions are identified not based on GPS technologies, pseudo-ranges can become estimates of distances between position-sensing devices and locations whose known and well-defined co-ordinates can be broadcasted and captured by the position-sensing devices.

According to another aspect, embodiment of the present invention can enable companies to be aware of status information of its inventory in real time. The inventory can be within the company or with the company's partners. If there are adverse changes in the status information, the present invention can quickly identify them. Based on the identification, embodiment of the present invention can also recommend and/or implement changes to remedy the situation. Such operations can be performed in real time. For example, in one embodiment, these operations can recommend or implement changes when changes in the status information exceed preset thresholds. Based on different embodiments of the invention, companies can have intimate knowledge of their inventory and, if necessary, can quickly react. Such information and control can save companies significant costs, without sacrificing superb services to their customers.

Figure 29:
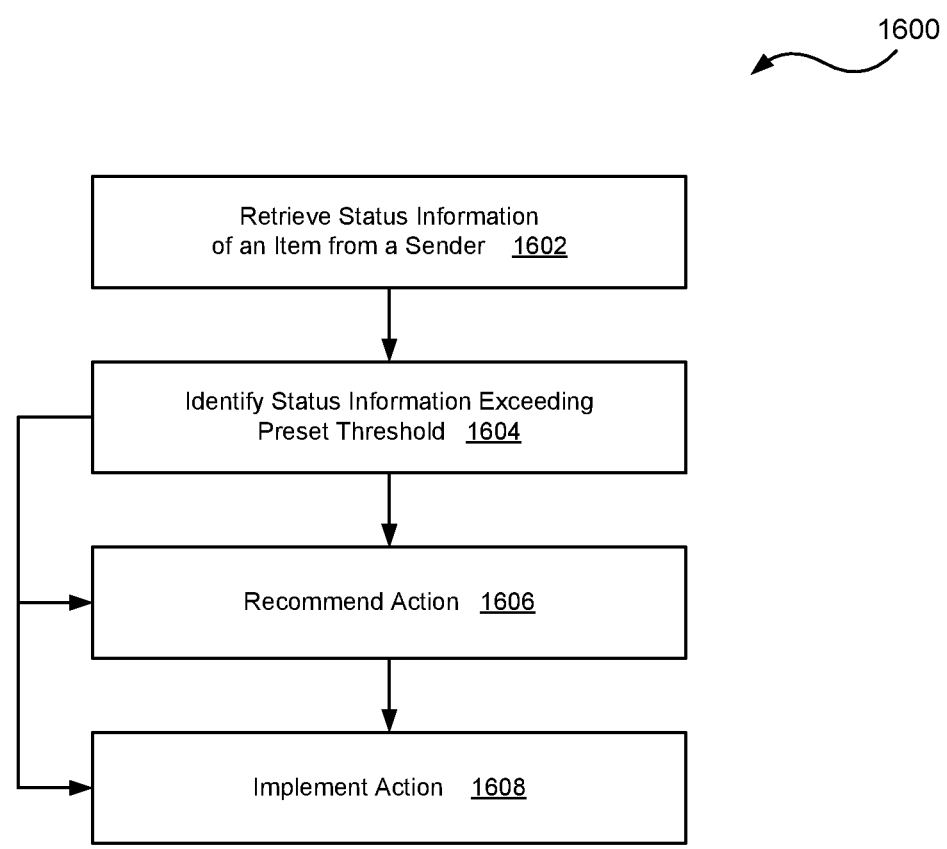
FIG. 29 shows one embodiment of the present invention.

FIG. 29 shows an inventory management process 1600 according to one embodiment of the present invention. A computing system of a company retrieves 1602 status information of an item from a sender. Based on the retrieved information, the computing system identifies 1604 that the status information has exceeded a preset threshold. Thereafter, the computing system can recommend 1606 and/or implement 1608 an action.

In general, the status information is obtained by a device. As an example, the status information is related to the position of an item. The position can be obtained by a position detector, such as a Global Positioning System (GPS) device. The position information can be longitudinal and latitudinal coordinates or it can be a label pertaining to the coordinates, such as a physical address, business establishment, landmark, etc. An item of the company is typically an inventory item of the company. An item can be a part or component, or a group of similar parts or components packaged as a unit.

Figure 30:
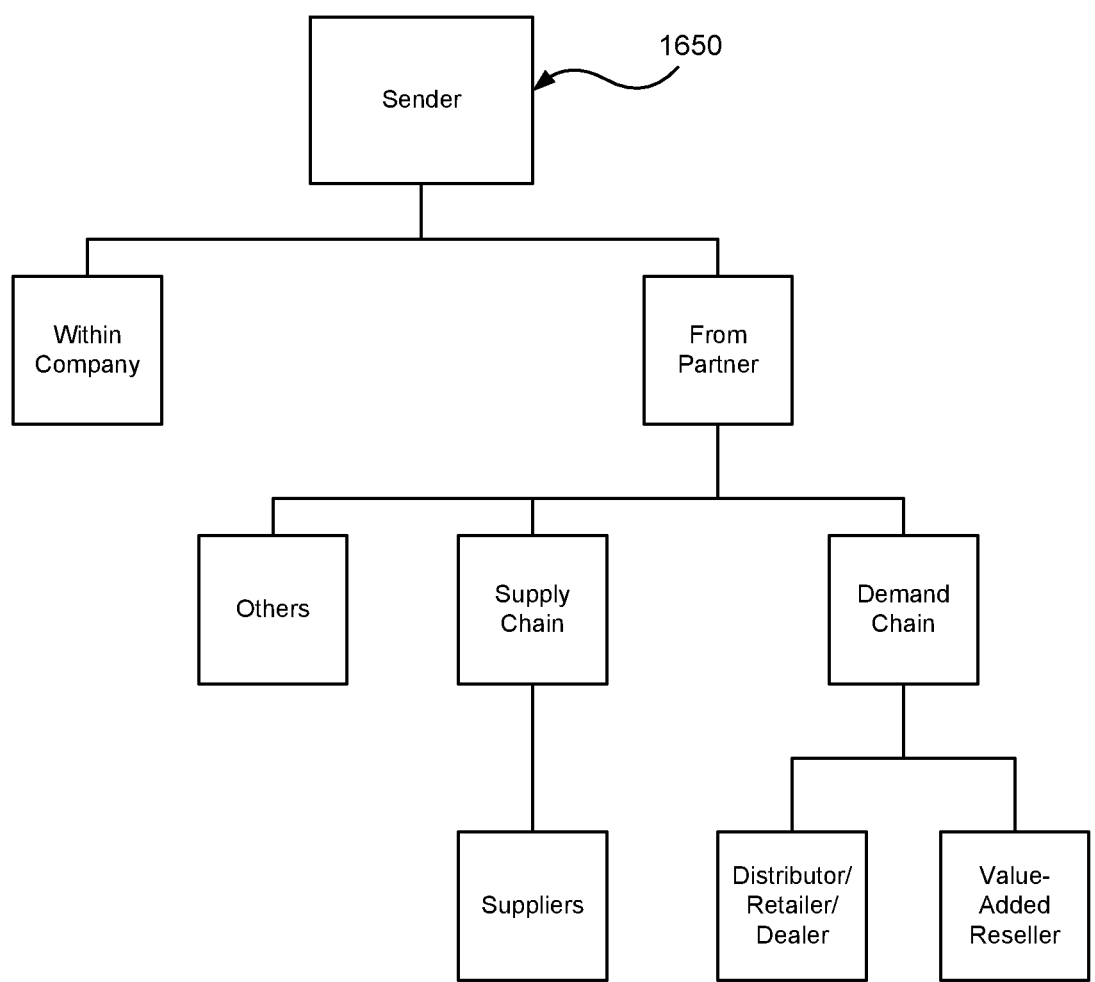
FIG. 30 shows examples of senders of position and/or status information in the present invention.

FIG. 30 shows examples of a sender 1650 of status information according to one embodiment of the present invention. The sender 1650 can be from within the company. The sender 1650 can be a computing system of or associated with the company, such as a computing system from another department within the company. For example, an item has arrived into a warehouse with a warehouse management application. That application automatically transmits the position of the item to a material requirement planning application at another site of the company.

In another embodiment, the sender 1650 is from a partner of the company. The partner can be a supply chain partner. It can be a supplier helping to supply an item to the company. The partner can also be a demand chain partner, helping to distribute an item, or an altered or modified version of the item to a customer of the company. The demand-chain partner can be a distributor, a retailer or a dealer. In another example, the demand-chain partner can be a value-added reseller. Typically, the sender 1650 is a computing system of or associated with the partner.

Figure 31A:
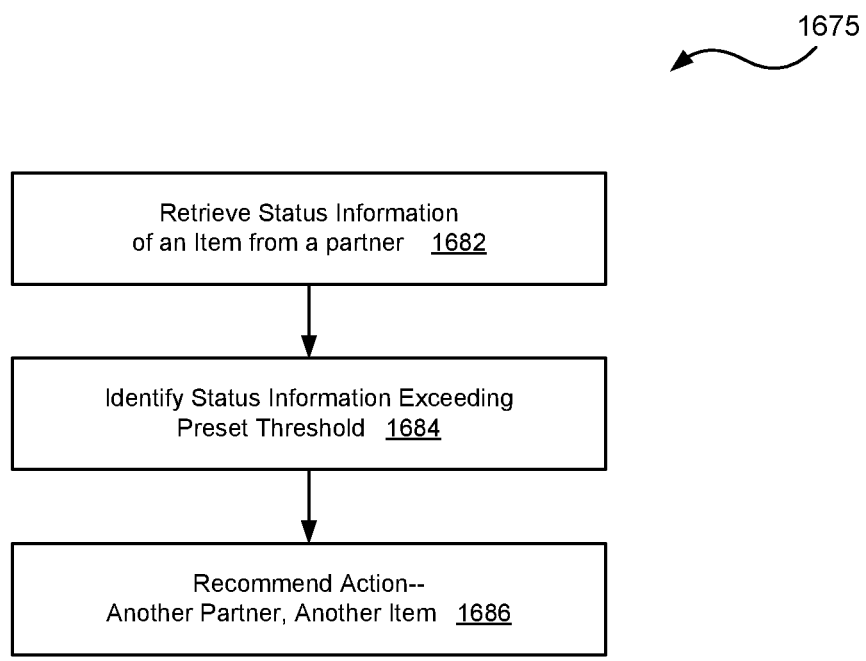
FIGS. 31A-31C shows an embodiment of the present invention regarding two partners.

FIG. 31A shows another embodiment of an inventory management process 1675 according to another embodiment of the present invention. In this embodiment, the company has at least two partners. A computing system of the company retrieves 1682 the position and another piece of status information of a first item from a first partner. This retrieval operation is achieved through a network. The network can include a wired network, a wireless network or both. The wireless network can be a data network. The wireless network can be a Short Message Service (SMS) network, a cellular network, a local wireless network (Bluetooth, Wi-Fi, etc.) or other wireless network. The network can include at least a portion of the Internet (i.e., a global computer network). In another embodiment, the network can be a local area network or a wide area network.

The computing system analyzes the retrieved information to determine 1684 whether any of the retrieved status information exceeds a preset threshold. Based on the identification, the computing system recommends 1686 an action. The action pertains to a second partner regarding a second item. Both the first and second items here can be related to a product of the company.

As an example, the first partner is shipping two hundred stainless steel plates to the company. After coating with a specific color, each plate will become a base-plate subassembly of a lamp. The company will then send them to a value-added reseller. Depending on what a customer wants, the reseller would package together the corresponding base-plate subassembly with a head lamp subassembly for the customer. The shipment of the stainless steel plates from the first partner takes about two weeks. During shipment, status information indicates that the temperature and humidity of the environment surrounding the plates are too high for the plates. At least 25% of the plates would probably be oxidized upon arrival. Such defect rate is too high. Consequently, the computing system of the company sends a message to the value-added reseller. The message recommends the value-added reseller to delay their order of the head lamp subassemblies. The company probably needs to replace this earlier shipment of steel plates and thus the necessary steel plates will be late to arrive.

Figure 31B:
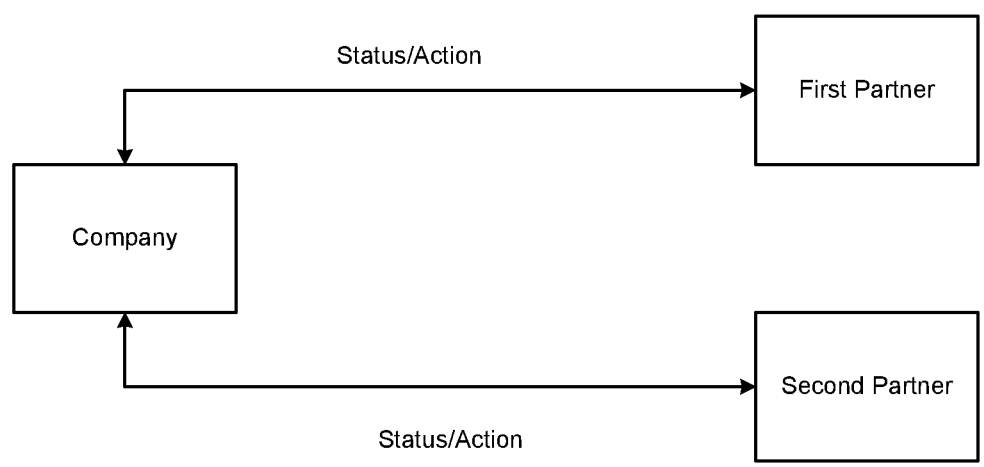

FIG. 31B illustrates one way for the flow of information among the company and its two partners. In this case, the company can receive status information from two of its partners, and can recommend or implement appropriate actions accordingly to both of them.

Figure 31C:
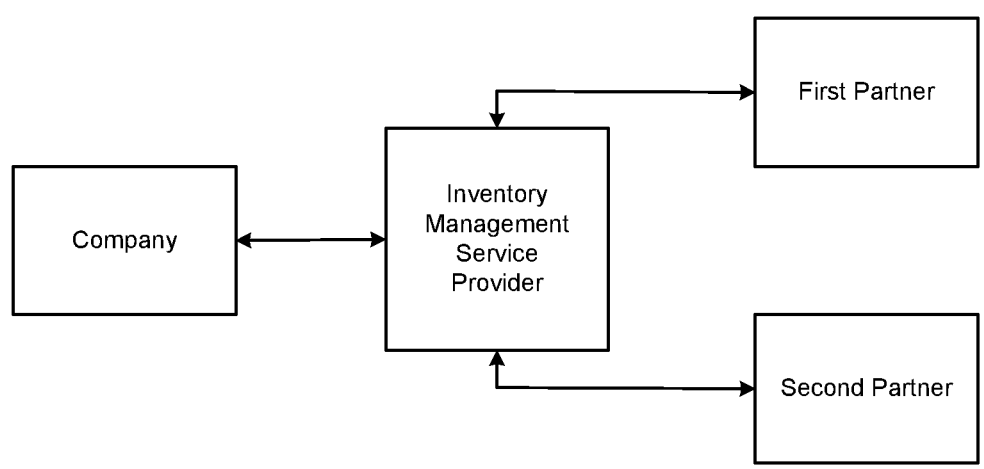

FIG. 31C illustrates another way for the flow of information among the company and its partners. In this case, there is a third party inventory management service provider. This provider can be responsible for monitoring the status of the different items and can also be responsible for their movement or delivery of the items. In one embodiment, this service provider is also a partner of the company.

Figure 32:
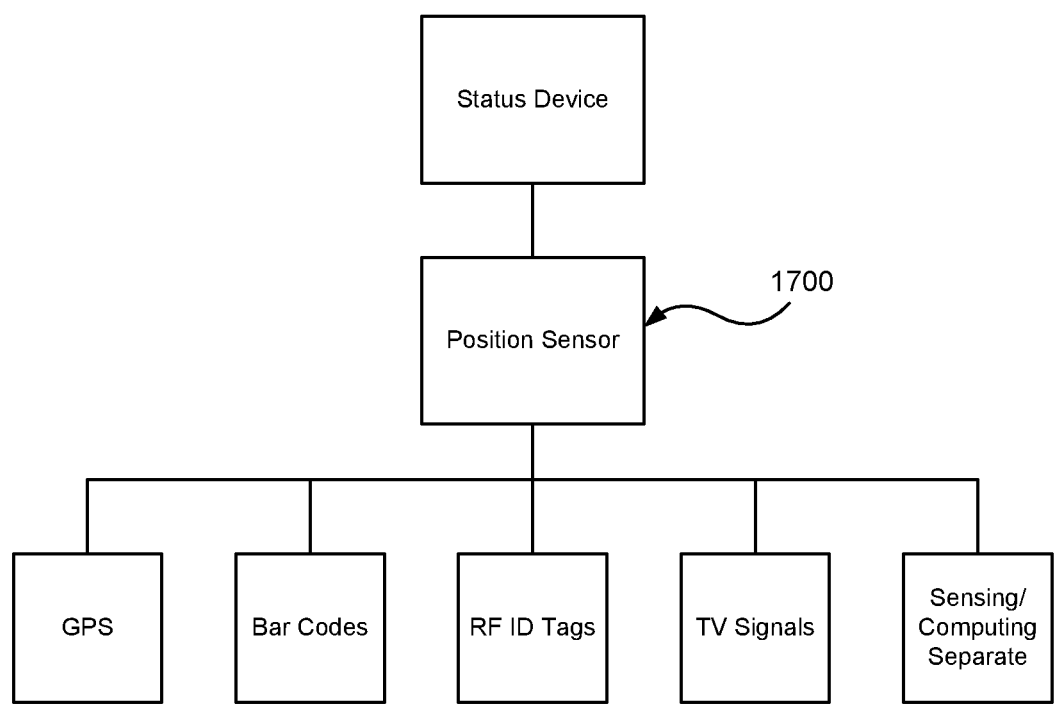
FIG. 32 shows examples of position sensors in the present invention.

The status information regarding an item can be obtained by a device attached to, in close proximity with or applicable to, the item. One type of status information is position information. FIG. 32 shows examples of position sensors 1700 in the present invention. The position sensor can be based on GPS, a piece of bar codes, a RF ID tag or TV signals. The position sensor can be separated into a sensing unit and a computing unit. Different embodiments of position sensors have been described in the patent application, entitled, "INEXPENSIVE POSITION SENSOR", filed concurrently herewith, which is hereby incorporated herein by reference.

Figure 33:
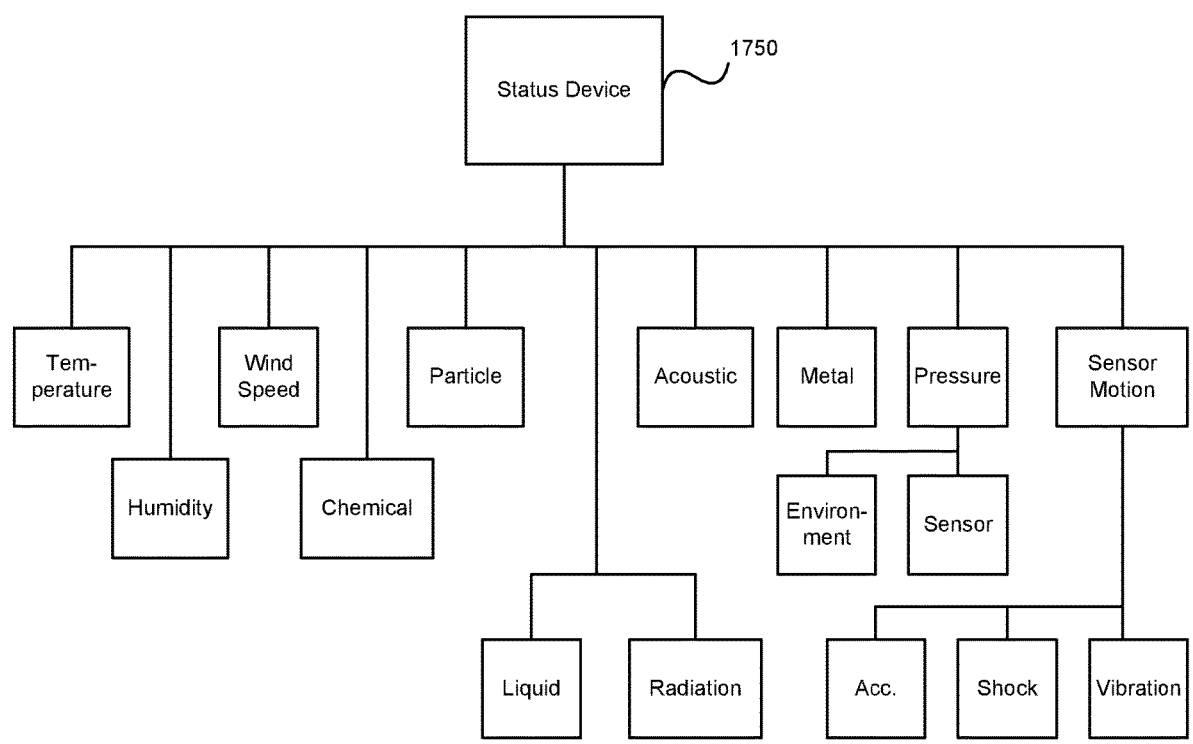
FIG. 33 shows examples of other types of status sensors in the present invention.

FIG. 33 shows examples of other types of status sensors 1750 (status devices) suitable for use with the present invention. The status device 1750 can be an environment sensor that captures information regarding the environment where the corresponding item (or a position sensor in close proximity to the item) is located. For example, the status device 1750 can be a sensor for temperature, humidity, wind speed, chemicals, particle, liquid, radiation, sound/acoustic, metal or pressure. When the status device 1750 is a chemical sensor, the sensor can, for example, sense oxygen level or carbon monoxide level. Similar to a chemical sensor, the status device 1750 can be an odor sensor. When the status device 1750 is a particle sensor, the sensor can, for example, be a smoke detector. When the status device 1750 is a radiation detector, the sensor can, for example, be a light sensor or an infrared detector. When the status device 1750 is a pressure sensor, the sensor can, for example, sense atmospheric pressure or tire pressure.

The status device 1750 can also capture information pertaining to an item or a position sensor. For example, the status device 1750 can sense information pertaining to the item itself (or the position sensor 1700), such as its motion or pressure asserted on it. The motion can be its acceleration, shock or vibration.

Again, different embodiments of status devices, and examples of communication approaches among each other and with remote sites have been described in the patent application entitled, "INEXPENSIVE POSITION SENSOR", filed concurrently herewith, which is hereby incorporated herein by reference.

Figure 34:
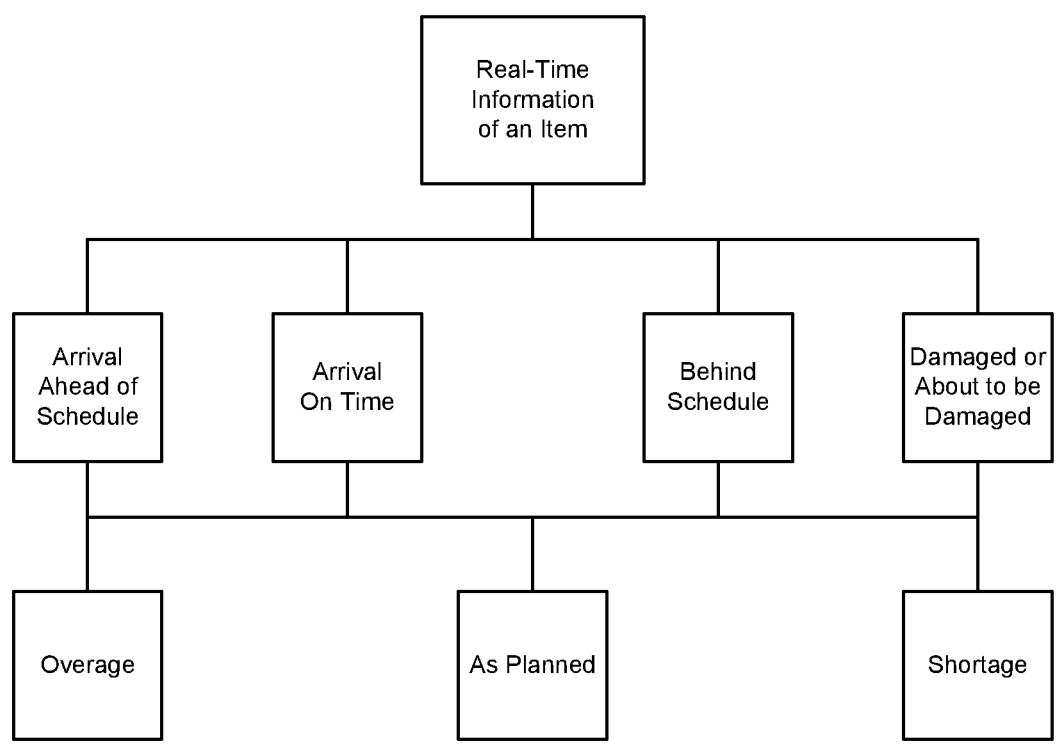
FIG. 34 shows examples of real-time information of an item in the present invention.

The information acquired from the position sensors and other types of status sensors can transmit in real time to the company. In other words, the company is aware of the position and other status information of the item in real time. FIG. 34 shows examples of real-time information of the item. Based on position information retrieved, the company can be aware of where the position of the item is. From that, the company is able to decide whether the item will be arriving ahead of schedule, on time or behind schedule. Based on other status information retrieved, the company can be aware that an item is damaged or is about to be damaged unless certain action is taken. Then, the company can determine whether there will be an overage or shortage of certain inventory, or whether the amount of inventory will be as planned.

Figure 35:
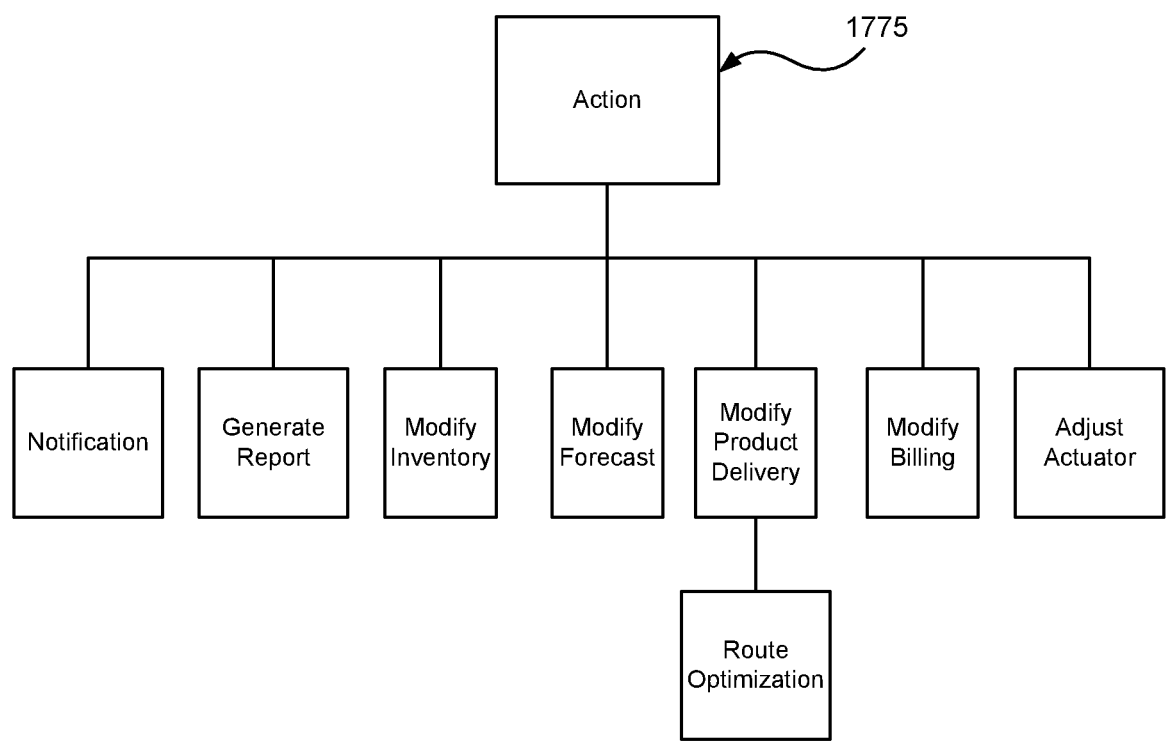
FIG. 35 shows examples of actions implemented by the present invention in view of certain status information.

Based on the status information, the company can take different actions. FIG. 35 shows examples of such actions 1775. One department of the company could have received the information. That department can notify other departments within the company, or the company's partners. For example, if the shipment is of certain hazardous materials, then the real-time notification can indicate that the shipment has deviated from its pre-approved routes or is traveling at unsafe speeds. This will allow management to intervene before a major problem develops.

Another action can be on generating reports.

In view of changes in the status information of an item, the company might have to adjust its inventory. For example, the company might have to write off inventory on its head lamp assemblies if the base plate assemblies are not arriving in time to meet competitors' new models.

The company might have to modify its forecast.

In another example, the company might have to modify its product delivery schedule. This can include route optimization. For example, a transportation partner is responsible for delivering different items to the company, and to the company's value-added reseller. In view of defective shipment of one item, the transportation partner should re-optimize the routes of other items. Route optimization typically allows the transportation partner to reduce empty miles and fuel costs, and increase effective loads being carried. This in turn can lead to higher revenue with fewer resources.

Based on the status information, the company might have to modify its billing to its customers and/or partners. Typically, billing is modified if delivery schedule has to be adjusted.

In yet another example, the company through its computing system can control an actuator so as to modify the status. For example, the temperature in the environment of an item is too high. The company can turn on a fan in the vicinity of the item to reduce the temperature.

In still another example, an insurance firm could use, or be notified of, the status information. For example, an insured 600 lb. Bluefin Tuna from Japan has gone bad while it is located at the California shipping dock. The wholesale price of the Tuna is more than $30,000.00 USD. The insurance firm identifies, through an investigation, that somewhere during the transportation the refrigeration of the tuna failed and thus the temperature for the Tuna was unacceptably high. To determine liability, it will be useful for the insurance firm not just to know where, but also when and for how long the temperature was too high.

Figure 36:
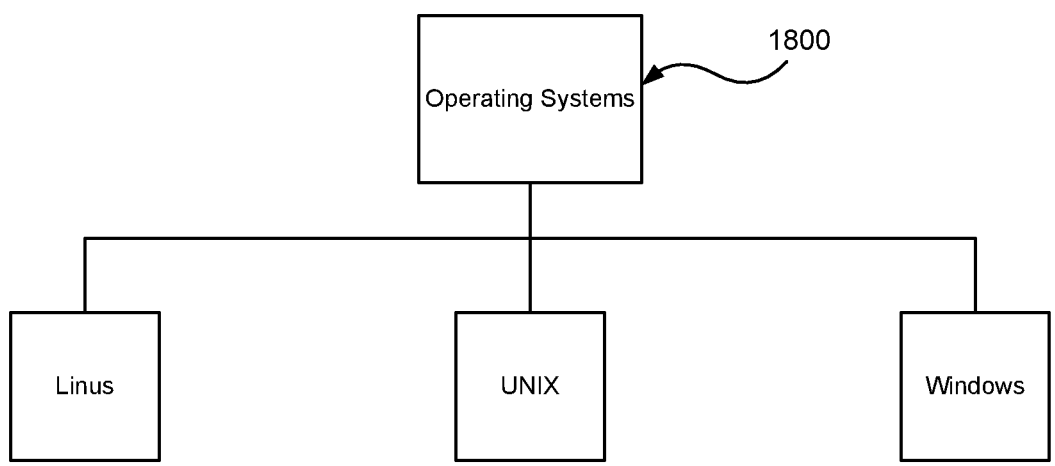
FIG. 36 shows examples of operating systems in the present invention.

The status information may be coming from different types of devices, such as handheld, portable or desk top computers, Internet kiosk or other Internet appliances. They may use different operating systems. FIG. 36 shows examples of operating systems 1800 in the present invention, such as Linux, UNIX and Windows. Different devices, with different operating systems, might have to plug-in and access information from the company and its partners or vice versa.

Figure 37:
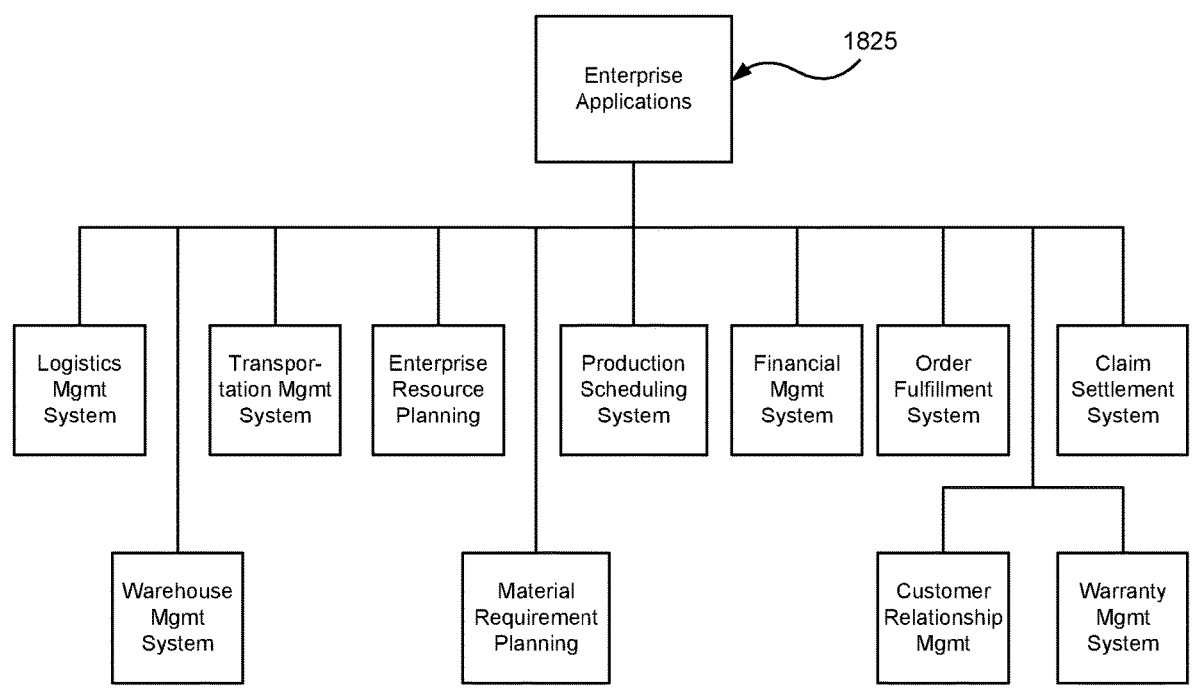
FIG. 37 shows examples of enterprise applications in the present invention.

The company can be interacting with different partners, or information can be coming from different departments within the company. FIG. 37 shows examples of enterprise applications 1825 accessing or using different status information according to one embodiment of the present invention.

The company might have a logistics management system that is responsible for the logistics of items. This company might also have a warehouse management system and a transportation management system. The warehouse management system is responsible for managing items in a warehouse. The transportation management system is responsible for managing items on the road.

The company might have an enterprise resource planning system that is responsible for planning the resources required by the company in, for example, producing a product. The company might have a material requirement planning system that is responsible for planning different materials required for the company's products. In another example, the company might have a production scheduling system that is responsible for scheduling the production of different products.

In yet another embodiment, the company might have a financial management system that is responsible for the financial planning of the company. This system might be responsible for handling loans to borrow money to finance building the products. This system can also be responsible for the billing of the company. There might be a separate order fulfillment system that is responsible for handling the company's orders. Shipment-to-order reconciliation might also be handled by the order fulfillment system.

The company might also have a customer relationship management system that is responsible for managing customer issues.

In another example, the company can have a warranty management system and may have a claim settlement system. The warranty management system is responsible for managing issues regarding warranties on the different items. The claim settlement system is responsible for managing claims if there are disputes arising from the items, such as changes in its delivery time or other status.

One or more of the different systems or enterprise applications described in FIG. 37 can be at a partner's site. For example, an insurance company, which can be considered a company's partner in one embodiment, might have a claim settlement system. In another example, one or more of the systems might reside at an inventory management service provider.

In many situations, the status information of an item should be available to the different enterprise applications, with examples shown in FIG. 37. To illustrate, in view of a piece of status information, the transportation management system determines that an item will be late in arrival by one week. This piece of information can affect parts movement in a warehouse (warehouse management system), resources in the company (enterprise resource planning), materials required to make a product (material requirement planning system), the corresponding product delivery schedule (production scheduling system), the billing of a customer (financial management system), the customer order fulfillment schedule (order fulfillment system), notifying the customer regarding the delayed shipment (customer relationship management system), and settling claims with the customer or an insurance carrier (claim settlement system). In one embodiment, the status information effectively flows among the different applications to allow data delivery to be immediately funneled into the different applications. Without requiring a personnel to key in data in data to the different applications, the company will reduce the possibility of data entry errors and the amount of paperwork. In turn, this will accelerate the billing cycle, increase revenue for the company, and improve customer satisfaction.

The above example illustrates the flow of status information among the different systems/applications. In one embodiment, only certain systems/applications with the appropriate permission level can have access to the status information. Or, only managers above a certain level will have the permission to access certain status information.

The company's computing system and its partner's computing system might be using different programming language for different enterprise applications in different operating systems. Different systems might rely on different communication and data exchange standards. Data from the partner can be in flat files, SQL database formats, spreadsheets, HTML, XML or other formats that can be different from that of the company. For two systems to interoperate, data from one system should be easily accessible by the other system.

Figure 38:
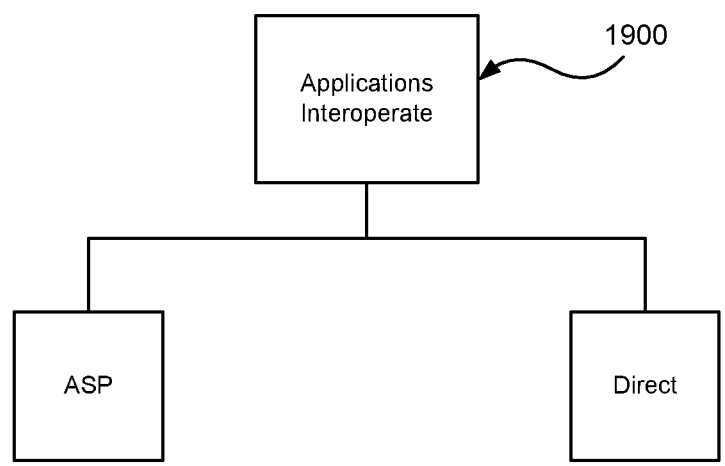
FIG. 38 shows examples of ways to allow different enterprise applications to interoperate in the present invention.

FIG. 38 shows examples of ways 1900 to allow different applications to interoperate. In one approach, instead of having applications in different departments within the company, or applications in different partners' sites to interoperate, an application service provider (ASP) serves as an intermediary to be responsible for this process. The ASP can send and receive status information to the different applications. In other words, the ASP can serve as a hub, with the different systems interacting with it.

In one embodiment, the ASP is also responsible for monitoring the status of an item. The ASP can also be responsible for placing corresponding sensor(s) or device(s) on or in the item. The ASP can wirelessly track the item. The company can set threshold values for the ASP. If certain threshold value has been exceeded, the ASP can transmit such information/message to different computing systems/enterprise applications designated by the company. It would be up to the ASP to modify the message to adapt to the attributes of the different designations. If specific actions are required to be performed, the company or its partners can send a request/message to the ASP. The request/message can be through specific computing systems/applications. The ASP could thereafter send messages to the appropriate recipients to initiate the actions. In yet another example, the ASP could also control actuators.

With such an ASP, the company and/or its partners can subscribe to its service by paying the ASP.

In another embodiment, different enterprise applications can interoperate with each other, instead of using a third-party (e.g., ASP).

Figure 39:
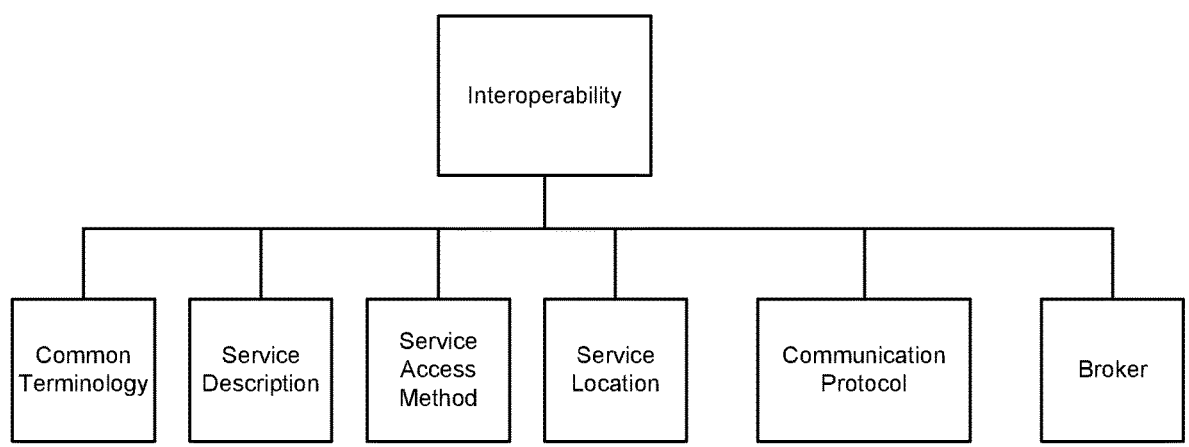
FIG. 39 shows examples of issues regarding interoperability in the present invention.

FIG. 39 shows examples of issues regarding interoperability or information accessibility. Information, such as in messages, can be sent from one system to be accessed by another system, or to be operated on by different systems for a service.

In one embodiment, the messages use common terminology that the recipient system and the transmitting system agree. For example, both systems understand the meaning of the term, dollar, is the U.S. dollar. The company's system and its partner's system understand a set of terms. These terms have meaning understood by the different systems.

There can be a description of the service in the message. The description indicates what type of service is being asked for by the message. For example, the message can be for buying an item from a supplier.

There can be a section in the message on how the service would be accessed. It can describe how a transaction or a service is represented. For example, if the message is for buying an item from a supplier, the message can include the name of the item, its price, the quantity, the delivery time, and the F.O.B. location.

There may also be a description in the message as to the location of the service. For example, there can be a URL indicating where to get the service regarding buying an item from a supplier.

In one embodiment, systems to interoperate also agree on the communication protocol, defining how the message will be transmitted.

In yet another embodiment, there can also be a broker providing information on the identities of the businesses and services they provide.

There can also be security protections. Depending on the potential threats of an attacker, to reduce risk to an acceptable level, different systems can apply specific security and technological countermeasures. HTTPS is an example of a standard for encrypted transport connections, and can provide a basic level of security protection.

To automate business processes, one embodiment uses Web services. It can provide interoperability among multiple operating systems, enterprise applications and programming languages. It can be implemented by an application service provider. In another embodiment, Web services can be exposed on the Web by Simple Object Access Protocol (SOAP), described by Web Services Description Language (WSDL) files and registered in Universal Description, Discovery and Integration (UDDI). SOAP can be the communications protocol for XML Web services to exchange information in a decentralized and distributed environment. A WSDL file can be an XML file describing a set of SOAP messages and how the messages should be exchanged. Typically, a WSDL file describes message contents or what a service does, such as the operations (methods) the service provides; how a service is accessed, such as the communication protocols used to talk to the service; and where a service is available, such as details of protocol-specific network addresses. UDDI can be an information database of Web services. A UDDI directory entry can be an XML file describing a company and the services it offers. Examples of such Web services are already defined or are in the process of being defined by such standard bodies as World Wide Web Consortium (W3C). In yet another embodiment, the Web services depend on either .NET or J2EE.

To illustrate how a number of the embodiments can be used, they are applied to the antifreeze challenge discussed in the background section. Each antifreeze package can have a RF ID tag. As the package moves through a point-of-sales system terminal, its sales is registered. Such an approach allows each supermarket to keep track of the amount of antifreeze getting out of their door. In addition, each supermarket has its temperature sensors to keep track of the temperatures around the supermarkets.

Web service messages including the sales of antifreeze and temperatures from the different supermarkets are sent to the antifreeze headquarters' logistics management system, such as every hour. Assume that each supermarket gets a shipment of antifreeze every seven days, and each supermarket needs to have at least a threshold level of antifreeze in their inventory. Since the logistics management system gets rate of change of the inventory level of antifreeze every hour, the system can automatically determine that if the rate of sales of antifreeze stays the same, the amount of antifreeze in their San Francisco supermarkets will go below their threshold level in five days. Based on the temperature data, the logistics management system also automatically forecasts that the rate of sales of antifreeze in San Francisco supermarkets will not go down.

Similarly, the headquarters is receiving position information of antifreeze and temperature information from its New York supermarkets. The logistics management system is aware that New York supermarkets are holding more than three weeks of inventories of antifreeze in their stores. Also, the antifreeze in the New York stores is not moving out of the stores fast enough. The rate of sales has actually gone down and will stay down due to the exceptionally high temperature in New York.

In real time, the logistics management system automatically decides to ship two-week worth of antifreeze inventories from New York supermarkets to San Francisco supermarkets. This decision can be emailed to a manager to get approval. If approved, the system would send a message to the transport management system of a delivery service partner. The message requests the partner to dispatch trucks to transport the antifreeze from New York supermarkets to San Francisco supermarkets on the same day. Moreover, the logistics management system can also email the manager for approval to produce more antifreeze to anticipate for increase demand. If approved, the logistics management system would send a message to its production scheduling system to have more antifreeze produced. Such fast responses based on real-time status information help companies satisfy customers, while reduce excess inventory.

The above-described systems, devices, methods and processes can be used together with other aspects of an object tracking system, including the various aspects described in: (i) U.S. Provisional Patent Application No. 60/444,198, filed Jan. 30, 2003, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (ii) U.S. Provisional Patent Application No. 60/418,491, filed Oct. 15, 2002, and entitled "SYSTEM, METHOD AND APPARATUS FOR ACQUIRING, PRESENTING, MONITORING, DELIVERING, MANAGING AND USING STATUS INFORMATION," which is hereby incorporated herein by reference; (iii) U.S. Provisional Patent Application No. 60/404,645, filed Aug. 19, 2002, and entitled "SYSTEM, METHOD AND APPARATUS FOR ACQUIRING, PRESENTING, MONITORING, DELIVERING, MANAGING AND USING POSITION AND OTHER INFORMATION," which is hereby incorporated herein by reference; and (iv) U.S. Provisional Patent Application No. 60/375,998, filed Apr. 24, 2002, and entitled "SYSTEM, METHOD AND APPARATUS FOR ACQUIRING, PRESENTING, MANAGING AND USING POSITION INFORMATION," which is hereby incorporated herein by reference.

The various embodiments, implementations and features of the invention noted above can be combined in various ways or used separately. Those skilled in the art will understand from the description that the invention can be equally applied to or used in other various different settings with respect to various combinations, embodiments, implementations or features provided in the description herein.

The invention can be implemented in software, hardware or a combination of hardware and software. The invention can also be embodied as computer readable code on a computer readable medium. The computer readable medium is any data storage device that can store data which can thereafter be read by a computer system. Examples of the computer readable medium include read-only memory, random-access memory, CD-ROMs, magnetic tape, optical data storage devices, and carrier waves. The computer readable medium can also be distributed over network-coupled computer systems so that the computer readable code is stored and executed in a distributed fashion.

The advantages of the invention are numerous. Different embodiments or implementations may yield different advantages.

One advantage of the invention is that interested persons can track and/or be notified as to status of an object. Another advantage of the invention is that status of an object can be monitored such that not only position information but also shipping conditions information are able to be monitored during shipment. Still another advantage of the invention is that status information of an object being transported can be obtained by an interested party (e.g., shipper, recipient or third-party) through notifications or through access to a website (e.g., tracking server).

From the foregoing it will be appreciated that a number of embodiments of the present invention help companies manage their inventories across their organizations and their partners. Based on the present invention, it becomes possible for companies, in real time, to be aware of the status information of numerous inventory items, and to have the agility to modify their internal execution plans, and their partners'. Thus, companies can modify, in real time, their own and affect their partners' inventory plans, production plans, and order fulfillment due to missed, delayed, changed or defective shipments thousands of miles away.

The present invention has described one or more GPS devices as to identify a position. However, the present invention is not limited to using GPS devices. In certain situations, other wireless or mobile devices can also serve as position-designating devices, such as devices based on GSM technologies or Wi-Fi technologies. Through the techniques of triangulation, these devices can also designate a position. Such triangulation techniques should be known to those skilled in the art.

The many features and advantages of the present invention are apparent from the written description and, thus, it is intended by the appended claims to cover all such features and advantages of the invention. Further, since numerous modifications and changes will readily occur to those skilled in the art, it is not desired to limit the invention to the exact construction and operation as illustrated and described. Hence, all suitable modifications and equivalents may be resorted to as falling within the scope of the invention.

What is claimed is:

1. A system for tracking and monitoring a plurality of assets, comprising:

a portable electronic apparatus physically coupled to or within a particular asset of the plurality of assets, the portable electronic apparatus including at least a location detection circuitry, a wireless communication circuitry, a circuit board, and at least one antenna, the location detection circuitry configured to acquire data pertaining to location of the portable electronic apparatus, the wireless communication circuitry supporting a plurality of wireless communication networks, including a first wireless network and a second wireless network, the portable electronic apparatus including shared frequency synthesizing circuitry including a crystal oscillator, the location detection circuitry being operatively connected to the shared frequency synthesizing circuitry, and the wireless communication circuitry being operatively connected to the shared frequency synthesizing circuitry, the crystal oscillator configured to produce a temperature-compensated oscillating signal, the temperature-compensated oscillating signal being shared by the location detection circuitry and the wireless communication circuitry;

a sensor device configured to wirelessly couple to the portable electronic apparatus via the first wireless network, the sensor device being configured to sense a condition at, in or proximate to the particular asset, and wirelessly transmit via the first wireless network, to the portable electronic apparatus, data pertaining to the condition being sensed by the sensor device; and a tracking and monitoring computing apparatus configured to receive at least (i) location data based on the data pertaining to location of the portable electronic apparatus and (ii) condition data based on data pertaining to the condition being sensed by the sensor device, transmitted from the portable electronic apparatus via at least the second wireless network, and the tracking and monitoring computing apparatus configured to analyze at least the location data and the condition data related to the particular asset being tracked and monitored, determine whether an electronic notification is to be provided based on at least the location data and/or the condition data, and initiate transmission of the electronic notification to at least an interested party if it is determined that the electronic notification is to be provided.

2. The system as recited in claim 1, wherein the electronic notification is wirelessly transmitted to a wireless device associated with the interested party.

3. The system as recited in claim 1, wherein the electronic notification is determined to be provided based on at least comparison of the condition data with one or more predetermined levels.

4. The system as recited in claim 3, wherein the electronic notification provided to the interested party alerts the interested party that a monitored condition of the particular asset has exceeded a predetermined level.

5. The system as recited in claim 1,
wherein the portable electronic apparatus includes a first substrate for supporting at least one integrated circuit, and a second substrate, with at least a portion of the at least one antenna on the second substrate, the second substrate being separate from the first substrate, and
wherein the second wireless network is different than the first wireless network.

6. The system as recited in claim 5, wherein the first wireless network is a local area network, and the second wireless network is a wide area network.

7. The system as recited in claim 5, wherein the first wireless network is a short-range wireless network, and the second wireless network is a cellular network.

8. The system as recited in claim 1, wherein the portable electronic apparatus is battery powered.

9. The system as recited in claim 8,
wherein the portable electronic apparatus includes a first substrate for supporting at least one integrated circuit, and a second substrate, with at least a portion of the at least one antenna on the second substrate, the second substrate being separate from the first substrate, and
wherein the second wireless network is being different than the first wireless network.

10. The system as recited in claim 1, wherein the at least one antenna includes a shared antenna for use with both the first wireless network and the second wireless network.

11. The system as recited in claim 10,
wherein the wireless communication circuitry includes a first wireless communication circuit supporting wireless communications over the first wireless network, and a second wireless communication circuit supporting wireless communications over the second wireless network, and
wherein the first wireless communication circuit and the second wireless communication circuit are electrically and physically coupled to the circuit board.

12. The system as recited in claim 1, wherein the at least one antenna is configured to be used with the first wireless network and the second wireless network, and wherein at least a portion of the at least one antenna is provided on the circuit board.

13. The system as recited in claim 1, wherein the location detection circuitry comprising global positioning system circuitry.

14. The system as recited in claim 1, wherein the particular asset is being shipped from a shipper to a recipient, and
wherein the tracking and monitoring computing apparatus is configured to enable a user to interact with a web interface to configure the electronic notification to the interested party regarding shipment of the particular asset to the recipient.

15. The system as recited in claim 1, wherein the particular asset is to be shipped from a requestor to a recipient, and
wherein the system further comprises a web interface that is configured to enable the requestor or the recipient to configure the electronic notification regarding shipment of the particular asset to the recipient.

16. A system for tracking and monitoring a plurality of assets, comprising:
an electronic controller configured to:
retrieve at least location data and condition data from a portable electronic apparatus coupled to or within a particular asset of the plurality of the assets;
analyze at least the location data and the condition data related to the particular asset being tracked and monitored; and
enable a wireless notification to be transmitted to at least a wireless device associated with an interested party to alert the interested party concerning the particular asset,
wherein the portable electronic apparatus is configured to wirelessly couple to at least one electronic sensor,
wherein the portable electronic apparatus receives data from the at least one electronic sensor regarding the condition data, at least a portion of the condition data pertaining to an attribute of an environment proximate to the at least one electronic sensor,
wherein the portable electronic apparatus includes wireless communication circuitry, a circuit board and an antenna, and includes or couples to a location acquisition device that is configured to acquire data regarding the location data, the wireless communication circuitry supporting wireless communication over a first wireless network and a second wireless network, the portable electronic apparatus including shared frequency synthesizing circuitry including a crystal oscillator, the location acquisition device being operatively connected to the shared frequency synthesizing circuitry, and the wireless communication circuitry being operatively connected to the shared frequency synthesizing circuitry,
wherein the crystal oscillator that produces a temperature-compensated oscillating signal, the temperature-compensated oscillating signal being shared by the location acquisition device and the wireless communication circuitry, and
wherein the location data and the condition data are related to the particular asset being tracked and monitored by the system.

17. The system as recited in claim 16,
wherein the wireless communication circuitry includes a first wireless communication circuit supporting wireless communications over the first wireless network, and a second wireless communication circuit supporting wireless communications over the second wireless network, wherein the first wireless communication circuit and the second wireless communication circuit are electrically and physically coupled to the circuit board, and wherein the antenna is configured for use with both the first wireless network and the second wireless network.

18. The system as recited in claim 17, wherein the antenna includes a shared antenna for use with both the first wireless network and the second wireless network.

19. A system for tracking and monitoring a plurality of assets, comprising:
a portable electronic apparatus physically coupled to or within a particular asset of the plurality of assets, the portable electronic apparatus including at least a location detection circuitry, a wireless communication circuitry, a circuit board, and an antenna, the location detection circuitry configured to acquire data pertaining to location of the portable electronic apparatus, the wireless communication circuitry supporting a plurality of wireless communication networks, including a first wireless network and a second wireless network, the portable electronic apparatus including shared frequency synthesizing circuitry including a crystal oscillator, the location detection circuitry being operatively connected to the shared frequency synthesizing circuitry, and the wireless communication circuitry being operatively connected to the shared frequency synthesizing circuitry;
a plurality of sensor devices configured to wirelessly couple to the portable electronic apparatus via the first wireless network, the plurality of sensor devices being configured to sense one or more conditions at, in or proximate to the particular asset, and wirelessly transmit via the first wireless network, to the portable electronic apparatus, data pertaining to the one or more conditions being sensed by the plurality of sensor devices; and
a tracking and monitoring computing apparatus configured to receive (i) location data based on the data pertaining to location of the portable electronic apparatus and (ii) condition data based on data pertaining to the one or more conditions being sensed by the plurality of sensor devices, transmitted from the portable electronic apparatus via at least the second wireless network, and the tracking and monitoring computing apparatus configured to analyze at least the location data and the condition data related to the particular asset being tracked and monitored, determine whether an electronic notification is to be provided based on at least the location data and/or the condition data, and initiate transmission of the electronic notification to at least an interested party if it is determined that the electronic notification is to be provided, wherein the wireless communication circuitry includes a first wireless communication circuit supporting wireless communications over the first wireless network, and a second wireless communication circuit supporting wireless communications over the second wireless network, and wherein the includes crystal oscillator is configured to produce a temperature-compensated oscillating signal, the temperature-compensated oscillating signal being shared by the first wireless communication circuit and the second wireless communication circuit.

20. The system as recited in claim 19,
wherein the first wireless communication circuit and the second wireless communication circuit are electrically and physically coupled to the circuit board, and
wherein the antenna is configured for use with both the first wireless network and the second wireless network.

21. The system as recited in claim 19, wherein the antenna is configured to be used with the first wireless network and the second wireless network, and wherein at least a portion of the at least one antenna is provided on the circuit board.

22. The system as recited in claim 19, wherein the plurality of sensor devices comprises:
a light sensor configured to obtain information regarding light as a portion of the condition information; and
an acceleration sensor configured to obtain information regarding acceleration as a portion of the condition information.

23. The system as recited in claim 22, wherein the plurality of sensor devices further comprises two or more of the following sensors:
a temperature sensor configured to obtain information regarding temperature as a portion of the condition information; and
a humidity sensor configured to obtain information regarding humidity as a portion of the condition information; and
a pressure sensor configured to obtain information regarding pressure as a portion of the condition information.

24. The system as recited in claim 19, wherein the plurality of sensor devices comprises:
a temperature sensor configured to obtain information regarding temperature as a portion of the condition information; and
a humidity sensor configured to obtain information regarding humidity as a portion of the condition information.

25. The system as recited in claim 19, wherein the plurality of sensor devices comprises:
a temperature sensor configured to obtain information regarding temperature as a portion of the condition information; and
a pressure sensor configured to obtain information regarding pressure as a portion of the condition information.

* * * * *